(12) United States Patent
Valentin et al.

(10) Patent No.: US 7,868,228 B2
(45) Date of Patent: Jan. 11, 2011

(54) PHOSPHOPANTETHEINYL TRANSFERASES FROM BACTERIA

(75) Inventors: Henry Valentin, Davis, CA (US); Jiexin Peng, St. Louis, MO (US); Steven Screen, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 886 days.

(21) Appl. No.: 11/668,354

(22) Filed: Jan. 29, 2007

(65) Prior Publication Data

US 2008/0050505 A1 Feb. 28, 2008

Related U.S. Application Data

(66) Substitute for application No. 60/763,644, filed on Jan. 31, 2006.

(51) Int. Cl.
*A01H 5/00* (2006.01)
*C12N 15/82* (2006.01)
*C12N 5/10* (2006.01)
*C12N 1/20* (2006.01)
*C07H 21/04* (2006.01)

(52) U.S. Cl. ............... 800/298; 800/281; 536/23.2; 435/419; 435/252.3

(58) Field of Classification Search .............. None
See application file for complete search history.

(56) References Cited

U.S. PATENT DOCUMENTS

| 5,880,275 | A | 3/1999 | Fischhoff et al. ......... 536/12.71 |
| 6,140,486 | A | 10/2000 | Facciotti et al. ............ 536/23.2 |
| 6,200,624 | B1 * | 3/2001 | Mazer et al. ................ 426/590 |
| 6,319,698 | B1 | 11/2001 | Barclay ...................... 435/134 |
| 6,451,567 | B1 | 9/2002 | Barclay ...................... 435/134 |
| 6,459,018 | B1 | 10/2002 | Knutzon ................... 800/320.3 |
| 2004/0235127 | A1 | 11/2004 | Metz et al. .................. 435/183 |

FOREIGN PATENT DOCUMENTS

| WO | WO 2004/071467 | 8/2004 |
| WO | WO 2005/103253 | 11/2005 |

OTHER PUBLICATIONS

Daraselia et al., "Reannotation of *Shewanella oneidensis* genome,"*J. of Integrative Biology*, 7(2):171-175, 2003.
GenBank Accession No. AB262366, Aug. 12, 2006.
GenPept Accession No. BAF02836, Aug. 12, 2006.
GenPept Accession No. NP_717216, Jan. 25, 2008.
GenPept Accession No. YP_269804, Nov. 30, 2007.
Heidelberg et al., "Genome sequence of the dissimilatory metal ion-reducing bacterium *Shewanella oneidensis*," *Nature Biotechnology*, 20:1118-1123, 2002.
Methe et al., "The psychrophilic lifestyle as revealed by the genome sequence of *Colwellia psychrerythraea* 34H through genomic and proteomic analyses," *Proc. Natl. Acad. Sci. USA*, 102(31):10913-10918, 2005.
Orikasa et al., "A phosphopantetheinyl transferase gene essential for biosynthesis of n-3 polyunsaturated fatty acids from *Moritella marina* strain MP-1," *FEBS Letters*, 580:4423-4429, 2006.
Allen et al., "Structure and regulation of the omega-3 polyunsaturated fatty acid synthase genes from the deep-sea bacterium *Photobacterium profundum* strain SS9," *Microbiology*, 148:1903-1913, 2002.
Metz et al., "Production of polyunsaturated fatty acids by polydetide synthases in both prokaryotes and eukaryotes," *Sciene*, 293:290-293, 2001.
Orikasa et al., "Characterization of the eicosapentaenoic acid biosynthesis gene cluster from *Shewanella* sp. strain SCRC-2738," *Cellular and Molecular Biology*, 50(5):625-630, 2004.
European Office Action regarding Application No. 07710401.6-2405, dated Mar. 31, 2010.
Genbank Database Accession No. AF208013, Nov. 14, 2000.
Genbank Database Accession No. AF396670, Aug. 5, 2001.
Joshi et al., "Context sequences of translation initiation codon in plants," *Plant Mol. Biol.*, 35(6):993-101, 1997.
Metz et al., "Production of polyunsaturated fatty acids by polyketide synthases in both prokaryotes and eukaryotes," *Science*, 293(5528):290-293, 2001.
Flugel et al., "Holo-(Acyl Carrier Protein) Synthase and Phosphopantetheinyl Transferase in *Escherichia coli*," *J. Biol. Chem.* 275(2):959-968, 2000.
Lambalot et al., "A new enzyme superfamily—the phosphopantetheinyl transferases," *Chemistry & Biology* 3:923-936, 1996.
Office action dated Oct. 14, 2010, in Israeli Patent Application No. 193130.
Partial English translation of Israeli office action dated Oct. 14, 2010.

* cited by examiner

*Primary Examiner*—Elizabeth F McElwain
(74) *Attorney, Agent, or Firm*—Byron V. Olsen, Esq.; SNR Denton US LLP

(57) ABSTRACT

The invention relates generally to phosphopantetheinyl transferases that are required for activation of a polyketide synthase complex to synthesize long chain poly-unsaturated fatty acids (LC-PUFA's) such as docosahexaenoic acid and eicosapentaenoic acid. In particular, the invention relates to bacterial phosphopantetheinyl transferases, DNA constructs for their expression in host cells, and seed, oil and meal when the host cells comprise a plant. Also provided is a method for making a plant oil containing docosahexaenoic acid and/or eicosapentaenoic acid.

25 Claims, 9 Drawing Sheets

PHOSPHOPANTETHEINYL TRANSFERASES FROM BACTERIA

This application claims the priority of U.S. Provisional Patent Application 60/763,644, filed Jan. 31, 2006, the disclosure of which is incorporated herein by reference in its entirety.

BACKGROUND OF THE INVENTION

1. Field of the Invention

The invention relates generally to phosphopantetheinyl transferases that are involved in the activation of a polyketide synthase to synthesize long chain polyunsaturated fatty acids (such as docosahexaenoic acid and eicosapentaenoic acid.

2. Description of the Related Art

The primary products of fatty acid biosynthesis in most organisms are 16- and 18-carbon compounds. The relative ratio of chain lengths and degree of unsaturation of these fatty acids vary widely among species. Mammals, for example, produce primarily saturated and monounsaturated fatty acids, while most higher plants produce fatty acids with one, two, or three double bonds, the latter two comprising polyunsaturated fatty acids (PUFA's). Very long chain PUFAs such docosahexaenoic acid (DHA, 22:6) and eicosapentaenoic acid (EPA, 20:5) have been reported from several species of marine bacteria, including *Moritella* (*Vibrio*) *marina* and *Shewanella* sp. (U.S. Pat. No. 6,140,486) and from marine algae such as *Schizochytrium* sp. and *Thraustochytrium* sp. (US Patent Publication 20040235127).

Two main families of PUFAs are the omega-3 fatty acids (also represented as "n-3" fatty acids), exemplified by docosahexaenoic acid and the omega-6 fatty acids (also represented as "n-6" fatty acids), exemplified by arachidonic acid (ARA, 20:4). PUFAs are important components of the plasma membrane of the cell and adipose tissue, where they may be found in phospholipids and triglycerides, respectively. PUFAs are necessary for proper development in mammals, particularly in the developing infant brain, and for tissue formation and repair.

Several disorders respond to treatment with PUFAs. Supplementation with PUFAs has been shown to reduce the rate of restenosis after angioplasty. The health benefits of certain dietary omega-3 fatty acids for cardiovascular disease and rheumatoid arthritis also have been well documented (Simopoulos, 1997; James et al., 2000). Further, PUFAs have been suggested for use in treatments for asthma and psoriasis. Evidence indicates that PUFAs may be involved in calcium metabolism, suggesting that PUFAs may be useful in the treatment or prevention of osteoporosis and of kidney or urinary tract stones.

The majority of evidence for health benefits applies to the long chain omega-3 fats, EPA and DHA, which are in fish and fish oil. With this base of evidence, health authorities and nutritionists in Canada (Scientific Review Committee, 1990, Nutrition Recommendations, Minister of National Health and Welfare, Canada, Ottowa), Europe (de Deckerer et al, 1998), the United Kingdom (The British Nutrition Foundation, 1992, Unsaturated fatty-acids—nutritional and physiological significance: The report of the British Nutrition Foundation's Task Force, Chapman and Hall, London), and the United States (Simopoulos et al., 1999) have recommended increased dietary consumption of these PUFAs.

Major long chain PUFAs of importance include DHA and EPA, which are primarily found in different types of fish oil, and ARA, found in filamentous fungi such as *Mortierella*. For DHA, a number of sources exist for commercial production including a variety of marine organisms, oils obtained from cold water marine fish, and egg yolk fractions. However, there are several disadvantages associated with commercial production of PUFAs from natural sources. Natural sources of PUFAs, such as animals and fungi, tend to have highly heterogeneous oil compositions. The oils obtained from these sources therefore can require extensive purification to separate out one or more desired PUFAs or to produce an oil which is enriched in one or more PUFAs.

Natural sources of PUFAs also are subject to uncontrollable fluctuations in availability. Fish stocks may undergo natural variation or may be depleted by overfishing. In addition, even with overwhelming evidence of their therapeutic benefits, dietary recommendations regarding omega-3 fatty acids are not heeded. Fish oils have unpleasant tastes and odors, which may be impossible to economically separate from the desired product, and can render such products unacceptable as food supplements. Animal oils, and particularly fish oils, can accumulate environmental pollutants. Foods may be enriched with fish oils, but again, such enrichment is problematic because of cost and declining fish stocks worldwide. This problem is also an impediment to consumption and intake of whole fish. Nonetheless, if the health messages to increase fish intake were embraced by communities, there would likely be a problem in meeting demand for fish. Furthermore, there are problems with sustainability of this industry, which relies heavily on wild fish stocks for aquaculture feed (Naylor et al., 2000).

Other natural limitations favor a novel approach for the production of omega-3 fatty acids. Weather and disease can cause fluctuation in yields from fish. Large scale fermentation of organisms such as *Mortierella* is expensive. Natural animal tissues contain low amounts of ARA and are difficult to process. Microorganisms such as *Porphyridium* and *Mortierella* are difficult to cultivate on a commercial scale.

A number of marine microorganisms produce very long-chain PUFAs such as DHA and EPA by a polyketide synthase (PKS) mechanism. PKSs are enzyme complexes composed of multifunctional polypeptides that catalyze the synthesis of complex molecules from simple substrates in an iterative fashion. PKSs are well known in the art and numerous examples of such sequences can be found in the literature. In *Moritella marina*, a PKS synthesizes DHA from malonyl-CoA and acetyl-CoA. To activate this PKS, a phosphopantetheinyl transferase is required.

Phosphopantetheinyl transferases (Ppts) catalyze the post-translational activation of carrier proteins, fatty acid synthases, polyketide synthases, and non-ribosomal polypeptide synthetases by the covalent attachment of the 4'-phosphopantetheine moiety of coenzyme A to a conserved serine residue, a reaction required for the biosynthesis of natural products including fatty acids, polyketides, and nonribosomal peptides. Ppts have been classified according to their carrier protein specificity. In organisms containing multiple phosphopantetheine-requiring pathways, it has been suggested that each pathway has its own Ppt. While the *M. marina* PKS has been cloned (U.S. Pat. No. 6,140,486 (Facciotti et al.)), the Ppt was not found. Allen and Bartlett (2002) stated that they were unable to clone a Ppt gene from *Moritella*.

A number of approaches have been attempted for production of DHA and EPA in plants (WO05103253A1 (Singh et al), WO04071467A2 (Kinney et al)). These approaches had in common the use of desaturases/elongases in a stepwise fashion. This approach has the disadvantage of using 6-8 genes and leads to the accumulation of intermediates, a potentially undesirable outcome. Using a PKS/Ppt approach, the number of transgenes required would be smaller (4-5) and the accumulation of intermediates is not expected.

Therefore, it would be advantageous to obtain genetic material involved in long-chain PUFA biosynthesis and to express the isolated material in a plant system, in particular, a land-based terrestrial crop plant system, which can be manipulated to provide production of commercial quantities of one or more PUFA's. There is also a need to increase omega-3 fatty acid intake in humans and animals. Thus there is a need to provide a wide range of omega 3-enriched foods and food supplements so that subjects can choose feed, feed ingredients, food and food ingredients which suit their usual dietary habits. Particularly advantageous would be seed oils with increased DHA or EPA.

Currently there is only one omega-3 fatty acid, ALA, available in vegetable oils. However, there is poor conversion of ingested ALA to the longer-chain omega-3 fatty acids such as EPA and DHA. It has been demonstrated in copending U.S. Publication. No. 20040039058 for "Treatment And Prevention Of Inflammatory Disorders," that elevating ALA intake from the community average of 1 g/day to 14 g/day by use of flaxseed oil only modestly increased plasma phospholipid EPA levels. A 14-fold increase in ALA intake resulted in a 2-fold increase in plasma phospholipid EPA (Manzioris et al., 1994). Thus, to that end, there is a need for efficient and commercially viable production of PUFAs using a polyketide synthesis complex and the Ppts that activate the complex, genes encoding the Ppt, and recombinant methods of producing them. A need also exists for oils containing higher relative proportions of DHA or EPA, and food compositions and supplements containing them. A need also exists for reliable and economical methods of producing specific PUFA's. Oils derived from oilseed crops such as canola, soybean, corn, sunflower, or flax, that express a bacterial PKS complex are enriched in a long chain PUFA, DHA or EPA. Such oils can be utilized to produce foods and food supplements enriched in omega-3 fatty acids and consumption of such foods effectively increases tissue levels of EPA and DHA. Foods and foodstuffs, such as milk, margarine and sausages, all made or prepared with omega-3 enriched oils, will result in therapeutic benefits. Thus, there exists a strong need for novel nucleic acids of phosphopantetheinyl transferases capable of activating PKS for use in transgenic crop plants with oils enriched in PUFAs, as well as the improved oils produced thereby.

SUMMARY OF THE INVENTION

In one aspect, the invention provides isolated nucleic acids encoding a polypeptide with phosphopantetheinyl transferase activity. These may be used to transform cells or modify the fatty acid composition of a plant or the oil produced by a plant. One embodiment of the invention is an isolated polynucleotide sequence selected from the group consisting of (a) a polynucleotide hybridizing to SEQ ID NO:6 or SEQ ID NO:8, or a complement thereof, under conditions of 5×SSC, 50% formamide and 42° C.; (b) a polynucleotide encoding the polypeptide sequence of SEQ ID NO:5 or SEQ ID NO:7; and (c) a polynucleotide encoding a polypeptide with at least 75% sequence identity to a polypeptide sequence of SEQ ID NO:5 or SEQ ID NO:7. In certain further embodiments of the invention, the polynucleotides encode a polypeptide having at least 80%, 85% or 90% sequence identity to the polypeptide sequence of SEQ ID NO:5 or SEQ ID NO:7, including at least about 82%, 87%, 89%,92%, 95%, 98% and 99% identity to these sequences. Those of skill in the art will recognize that, as these sequences are related, a given polypeptide may simultaneously share 90% or greater homology to more than one of these polypeptide sequences. In a further embodiment, the encoded polypeptide has phosphopantetheinyl transferase activity.

In yet another aspect, the invention provides a DNA construct comprising a heterologous promoter operably linked to a DNA molecule encoding a polypeptide having phosphopantetheinyl transferase activity, wherein the DNA molecule is selected from the group consisting of: (a) a polynucleotide encoding the polypeptide sequence of SEQ ID NO:5 or SEQ ID NO:7; (b) a polynucleotide hybridizing to SEQ ID NO:6 or SEQ ID NO:8, or a complement thereof, under conditions of 5×SSC, 50% formamide and 42° C.; and (c) a polynucleotide encoding a polypeptide with at least 75% sequence identity to a polypeptide sequence of SEQ ID NO:5 or SEQ ID NO:7. In other embodiments, the promoter is functional in a prokaryotic cell or a eukaryotic cell. In certain embodiments, the eukaryotic cell in which the promoter is functional is a plant cell. In a further embodiment, the promoter is a seed-enhanced promoter.

In still yet another aspect, the invention provides a host cell transformed with a DNA construct comprising a heterologous promoter operably linked to a DNA molecule encoding a polypeptide having phosphopantetheinyl transferase activity provided by the invention. In another embodiment, the host cell further comprises a heterologous promoter operably linked to a DNA molecule encoding a polyketide synthase polypeptide comprising a phosphopantetheine attachment site. In a further embodiment, the DNA molecule encoding a polyketide synthase polypeptide comprising a phospopantetheine attachment site is from *Moritella marina*. In yet another embodiment, the DNA molecule encodes a polyketide synthase polypeptide with at least 70% sequence identity to SEQ ID NO:19, or any known polyketide synthase as described herein below. The host cell may be a plant, fungal or bacterial cell.

In still yet another aspect, the invention provides a plant and its progeny comprised of the host cells transformed with a DNA construct comprising a heterologous promoter operably linked to a DNA molecule encoding a polypeptide having phosphopantetheinyl transferase activity provided herein. Such a plant may be defined as comprising altered fatty acid metabolism relative to a plant of the same genotype lacking the DNA construct. In one embodiment, the plant is selected from the group consisting of canola, Brassica campestris, oilseed rape, rapeseed, soybean, crambe, mustard, castor bean, peanut, sesame, cottonseed, linseed, safflower, oil palm, flax, sunflower, corn, rice, barley, millet, rye, wheat, oat, alfalfa and sorghum. The invention also provides seed, oil and meal produced from the plant, which is defined as comprising a detectable DNA molecule or polypeptide provided by the invention. Additionally, the invention provides animal feed and human food compositions.

In still yet another aspect, the invention provides a method of making a plant oil containing docosahexaenoic acid and/or eicosapentaenoic acid comprising the steps of (a) growing a plant comprising the host cell of the invention further comprising a polyketide synthase; (b) producing seed; (c) and processing the seed to obtain oil.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
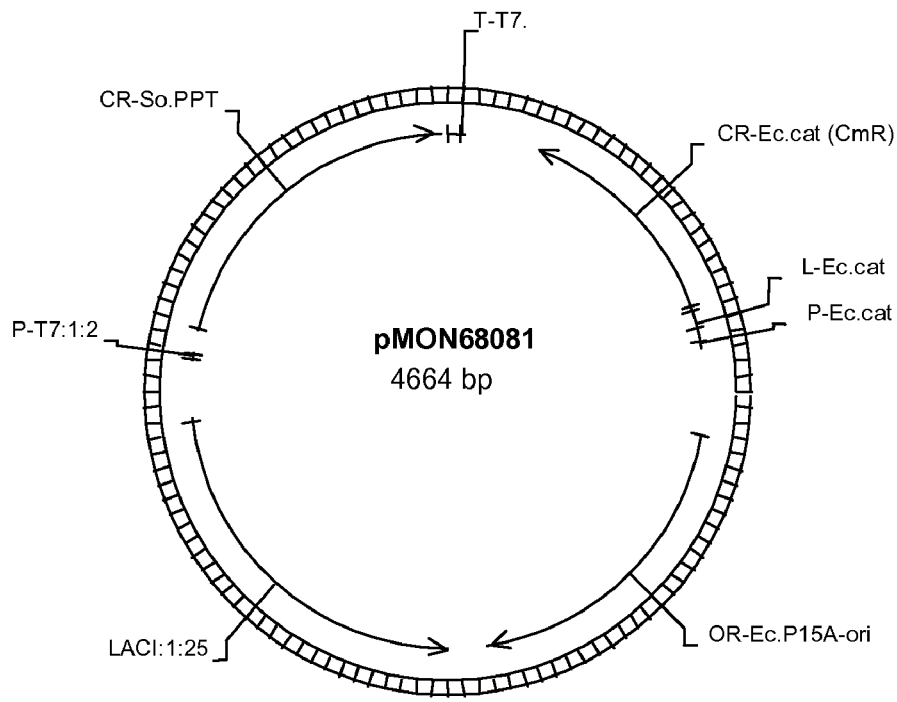
FIG. 1 shows a map of vector pMON68081.

The invention overcomes the limitations of the prior art by providing methods and compositions for creation of plants with improved DHA and/or EPA content. The modification of fatty acid content of an organism such as a plant presents many advantages, including improved nutrition and health benefits. Modification of fatty acid content can be used to achieve beneficial levels of DHA and/or EPA in plants, plant parts, and plant products, including plant seed oils as well as bacteria and fungi. For example, when DHA is produced in the seed tissue of a plant, the oil may be isolated from the seeds, typically resulting in an oil containing DHA, which may in turn be used to provide beneficial characteristics in foodstuffs and other products.

Various aspects of the invention include methods and compositions for modification of PUFA content of a cell, for example, modification of the PUFA content of a plant cell(s). Compositions related to the invention include novel isolated polynucleotide sequences, DNA constructs and plants and/or plant parts transformed by polynucleotides of the invention. Host cells may be manipulated to express a polynucleotide encoding a phosphopanteteheinyl transferase polypeptide which catalyzes the pantetheinylation of a phosphopantetheine attachment site of another polypeptide.

The following definitions are provided as an aid to understanding this invention. The phrases "DNA sequence," "nucleic acid sequence," "nucleic acid molecule," and "nucleic acid segment" refer to a physical structure comprising an orderly arrangement of nucleotides. The DNA segment, sequence, or nucleotide sequence may be contained within a larger nucleotide molecule, vector, or the like. In addition, the orderly arrangement of nucleic acids in these sequences may be depicted in the form of a sequence listing, figure, table, electronic medium, or the like.

The phrases "coding sequence," "coding region," "structural sequence," and "structural nucleic acid sequence" refer to all or a segment of a DNA sequence, nucleic acid sequence, nucleic acid molecule in which the nucleotides are arranged in a series of triplets that each form a codon. Each codon encodes a specific amino acid. Thus, the coding sequence, coding region, structural sequence, and structural nucleic acid sequence encode a series of amino acids forming a protein, polypeptide, or peptide sequence. The coding sequence, coding region, structural sequence, and structural nucleic acid sequence may be contained within a larger nucleic acid molecule, vector, or the like. In addition, the arrangement of nucleotides in these sequences may be depicted in the form of a sequence listing, figure, table, electronic medium, or the like.

The term "cDNA" refers to a double-stranded DNA that is complementary to and derived from mRNA.

"Expression" refers to the process by which a gene's coded information is converted into structures present and operating in the cell. Expressed genes include those that are transcribed into RNA and then translated into protein and those that are transcribed into RNA but not translated into protein (e.g., transfer RNA and ribosomal RNA).

As used herein, "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. An "exogenous" gene or "transgene" refer to a gene that has been introduced into the genome by a transformation procedure. A transgene includes genomic DNA introduced by a transformation procedure (e.g., a genomic DNA linked to its active promoter).

"Heterologous" refers to the relationship between 2 or more nucleic acid or protein sequences that are derived from different sources. For example, a promoter is heterologous with respect to a coding sequence if such a combination is not normally found in nature. In addition, a particular nucleic acid sequence may be "heterologous" with respect to a cell or organism into which it is inserted if it does not naturally occur in that particular cell or organism.

"Sequence homology" refers to the level of similarity between 2 or more nucleic acid or amino acid sequences in terms of percent of positional identity. The term homology is also used to refer to the concept of similar functional properties among different nucleic acids or proteins.

"Hybridization" refers to the ability of a first strand of nucleic acid to join with a second strand via hydrogen bond base pairing when the nucleic acid strands have sufficient sequence complementarity. As used herein, a nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Thus 2 nucleic acid strands are said to have sufficient complementarity when they can hybridize to one another with sufficient stability to permit them to remain annealed to one another under appropriate conditions.

As used herein, the term "homology" refers to the level of similarity or percent identity between polynucleotide sequences in terms of percent nucleotide positional identity, i.e., sequence similarity or identity. As used herein, the term homology also refers to the concept of similar functional properties among different polynucleotide molecules. Polynucleotide molecules are homologous when under certain conditions they specifically hybridize to form a duplex molecule. Under these conditions, referred to as stringency conditions, one polynucleotide molecule can be used as a probe or primer to identify other polynucleotide molecules that share homology. The phrase "stringent conditions" is functionally defined with regard to the hybridization of a nucleic-acid probe to a target nucleic acid (i.e., to a particular nucleic-acid sequence of interest) by the specific hybridization procedure, for example, discussed in Molecular Cloning: A Laboratory Manual, 3rd edition Volumes 1, 2, and 3. J. F. Sambrook, D. W. Russell, and N. Irwin, Cold Spring Harbor Laboratory Press, 2000 (Sambrook et al.). Accordingly, nucleotide sequences provided by the invention may be used for their ability to selectively form duplex molecules with complementary stretches of polynucleotide molecule fragments. Depending on the application envisioned one would desire to employ varying conditions of hybridization to achieve varying degrees of selectivity of probe towards target sequence. For applications requiring high selectivity, one will typically desire to employ relatively high stringent conditions to form the hybrids, e.g., one will select relatively low salt and/or high temperature conditions, such as provided by about 0.02 M to about 0. 15 M NaCl at temperatures of about 50° C. to about 70° C. A high stringent condition, for example, is to wash the hybridization filter at least twice with high-stringency wash buffer (0.2×SSC, 0.1% SDS, 65° C.). Additionally, formamide may be used to increase stringency. High stringency conditions therefore also include 5×SSC, 50% formamide and 42° C. Detection of polynucleotide molecules via hybridization is well known to those of skill in the art, and the teachings of U.S. Pat. Nos. 4,965,188 and 5,176, 995 are exemplary of the methods of hybridization analyses.

The phrase "isolated" means having been removed from its natural environment, regardless of its eventual disposition. For example, a nucleic acid sequence "isolated" from rice, such as by cloning from a rice cell, remains "isolated" when it is inserted into the genome of a corn cell.

The phrase "operably linked" refers to the spatial arrangement of two or more nucleic acid regions or nucleic acid sequences so that they exert their appropriate effects with respect to each other. For example, a promoter region may be positioned relative to a nucleic acid sequence such that transcription of the nucleic acid sequence is directed by the promoter region. The promoter region and the nucleic acid sequence are "operably linked."

The term "phosphopantetheinyl transferase or PPT" refers to an enzyme that catalyzes the post-translational activation of carrier proteins, for example, a polypeptide of a polyketide synthase, by the covalent attachment of the 4'-phosphopantetheine moiety of coenzyme A to a conserved serine residue.

The term "polyketide synthase" refers to an enzyme complex composed of multifunctional polypeptides that catalyze the synthesis of complex molecules from simple substrates in an iterative fashion. In *Moritella marina*, a PKS complex synthesizes DHA from malonyl-CoA and acetyl-CoA). For example, in *M. marina*, the PKS contains 4 polypeptides encoded by the open reading frames Orf5, Orf6, Orf7 and Orf8 (Metz et al, 2001), which are described as Orf6, Orf7, Orf8, and Orf9 in U.S. Pat. No. 6,140,486, respectively. To activate this complex, a phosphopantetheinyl transferase is required to pantethenylate the polypeptide encoded by Orf5. The PKS complex of *Shewanella* sp. SCRC2738 synthesizes EPA (Metz et al, 2001).

"Upstream" and "downstream" are positional terms used with reference to the location of a nucleotide sequence and the direction of transcription or translation of coding sequences, which normally proceeds in the 5' to 3' direction.

The terms "promoter" or "promoter region" refer to a nucleic acid sequence, usually found upstream (5') to a coding sequence, capable of directing transcription of a nucleic acid sequence into an RNA molecule. The promoter or promoter region typically provides a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, and the like. The activity or strength of a promoter may be measured in terms of the amounts of RNA it produces, or the amount of protein accumulation in a cell or tissue, relative to a second promoter that is similarly measured.

The phrase "3' non-coding sequences" refers to nucleotide sequences located downstream of a coding sequence and include polyadenylation recognition sequences and other sequences encoding regulatory signals capable of affecting mRNA processing or gene expression. These are commonly referred to as 3'-untranslated regions or 3'-UTRs. The polyadenylation signal is usually characterized by affecting the addition of polyadenylic acid tracts to the 3' end of the mRNA precursor. The use of different 3' non-coding sequences is exemplified by Ingelbrecht et al (1989).

"Translation leader sequence" or "5'-untranslated region" or "5'-UTR" all refer to a nucleotide sequence located between the promoter sequence of a gene and the coding sequence. The 5'-UTR is present in the fully processed mRNA upstream of the translation start sequence. The 5'-UTR may affect processing of the primary transcript to mRNA, mRNA stability or translation efficiency. Examples of translation leader sequences have been described (Turner and Foster, 1995).

"RNA transcript" refers to the product resulting from RNA polymerase-catalyzed transcription of a DNA sequence. When the RNA transcript is a perfect complementary copy of the DNA sequence, it is referred to as the primary transcript. An RNA sequence derived from posttranscriptional processing of the primary transcript is referred to as the mature RNA. "Messenger RNA" (mRNA) refers to the RNA that is without introns and that can be translated into polypeptide by the cell.

"DNA construct" refers to the heterologous genetic elements operably linked to each other making up a recombinant DNA molecule and may comprise elements that provide expression of a DNA polynucleotide molecule in a host cell and elements that provide maintenance of the construct. A plant expression cassette comprises the operable linkage of genetic elements that when transferred into a plant cell provides expression of a desirable gene product.

"Recombinant vector" refers to any agent by or in which a nucleic acid of interest is amplified, expressed, or stored, such as a plasmid, cosmid, virus, autonomously replicating sequence, phage, or linear single-stranded, circular single-stranded, linear double-stranded, or circular double-stranded DNA or RNA nucleotide sequence. The recombinant vector may be synthesized or derived from any source and is capable of genomic integration or autonomous replication.

"Regulatory sequence" refers to a nucleotide sequence located upstream (5'), within, or downstream (3') with respect to a coding sequence, or an intron, whose presence or absence affects transcription and expression of the coding sequence "Substantially homologous" refers to two sequences that are at least about 90% identical in sequence, as measured by the CLUSTAL W algorithm in, for example DNAStar (Madison, Wis.).

"Substantially purified" refers to a molecule separated from substantially all other molecules normally associated with it in its native state. More preferably, a substantially purified molecule is the predominant species present in a preparation. A substantially purified molecule may be greater than about 60% free, preferably about 75% free, more preferably about 90% free, and most preferably about 95% free from the other molecules (exclusive of solvent) present in the natural mixture. The phrase "substantially purified" is not intended to encompass molecules present in their native state. Preferably, the nucleic acid molecules and polypeptides of this invention are substantially purified.

The term "transformation" refers to the introduction of nucleic acid into a recipient host. The term "host" refers to bacteria cells, fungi, animals or animal cells, plants or seeds, or any plant parts or tissues including plant cells, protoplasts, calli, roots, tubers, seeds, stems, leaves, seedlings, embryos, and pollen.

As used herein, a "transgenic plant" is a plant having stably introduced into its genome, for example, the nuclear or plastid genomes, an exogenous nucleic acid.

The term "isogenic" as a comparative term between plants or plant lines having or lacking a transgene means plants or lines having the same or similar genetic backgrounds, with the exception of the transgene in question. For example, so-called sister lines representing phenotypically similar or identical selections from the same parent F2 population are considered to be "isogenic." When the progeny of a stable transformant plant are crossed and backcrossed with the plants of the untransformed parent line for 3 to 6 generations (or more) using the untransformed parent as the recurrent parent while selecting for type (genotype by molecular marker analysis, phenotype by field observation, or both) and for the transgene, the resulting transgenic line is considered to be highly "isogenic" to its untransformed parent line.

The terms "seeds" "kernels" and "grain" are understood to be equivalent in meaning. The term kernel is frequently used in describing the seed of a corn or rice plant. In all plants the seed is the mature ovule consisting of a seed coat, embryo, aleurone, and an endosperm.

Nucleic Acids Encoding Phosphopantetheinyl Transferase

The invention provides, in one embodiment, novel nucleic acids encoding phosphopantetheinyl transferases from *Moritella marina*. In certain embodiments, the nucleic acids comprise SEQ ID NOs:2, 4, 6 or 8. The invention also provides methods of using such nucleic acids, including SEQ ID NOs: 2, 4, 6 and 8. In one embodiment, these nucleic acid molecules are used in the context of this invention for altering the oil composition of a seed from a plant.

Such nucleic acid can be amplified using cDNA, mRNA or genomic DNA as a template and appropriate oligonucleotide primers according to standard PCR™ amplification techniques. Alternatively, they can be synthesized using standard synthetic techniques, such as an automated DNA synthesizer. Polynucleotides encoding desired phosphopantetheinyl transferases can be identified in a variety of ways. As an example, a source of the desired phosphopantetheinyl transferase, for example a library from *Moritella*, is screened with detectable enzymatically- or chemically-synthesized probes, which can be made from DNA, RNA, or non-naturally occurring nucleotides, or mixtures thereof. Probes may be enzymatically synthesized from polynucleotides of known phosphopantetheinyl transferases for normal or reduced-stringency hybridization methods. Oligonucleotide probes also can be used to screen sources and can be based on sequences of known phosphopantetheinyl transferases, including sequences conserved among known phosphopantetheinyl transferases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR™ from reverse transcribed mRNA from a known or suspected source; the PCR™ product can be the full length cDNA or can be used to generate a probe to obtain the desired full length cDNA.

Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA also can be employed.

If desired, the sequences of nucleic acids that code for phosphopantetheinyl transferases can be modified without changing the resulting amino acid sequence of the expressed protein so that the sequences are more amenable to expression in plant hosts. A coding sequence can be an artificial DNA. An artificial DNA, as used herein means a DNA polynucleotide molecule that is non-naturally occurring. Artificial DNA molecules can be designed by a variety of methods, such as, methods known in the art that are based upon substituting the codon(s) of a first polynucleotide to create an equivalent, or even an improved, second-generation artificial polynucleotide, where this new artificial polynucleotide is useful for enhanced expression in transgenic plants. The design aspect often employs a codon usage table produced by compiling the frequency of occurrence of codons in a collection of coding sequences isolated from a plant, plant type, family or genus. Other design aspects include reducing the occurrence of polyadenylation signals, intron splice sites, or long AT or GC stretches of sequence (U.S. Pat. No. 5,500,365). Full length coding sequences or fragments thereof can be made of artificial DNA using methods known to those skilled in the art. Modifications of the nucleotide sequences or regulatory elements disclosed herein which maintain the functions contemplated herein are within the scope of this invention. Such modifications include insertions, substitutions and deletions, and specifically substitutions which reflect the degeneracy of the genetic code.

The inventors have isolated DNA sequences from *Moritella marina* that produce polypeptides with phosphopantetheinyl transferase activity. The sequences encoding the phosphopantetheinyl transferases may be expressed in transgenic plants, microorganisms or animals to effect activation of a polyketide synthase. Other polynucleotides which are substantially identical to the phosphopantetheinyl transferase polynucleotides provided herein, or which encode polypeptides which are substantially identical to the phosphopantetheinyl transferase polypeptides, also can be used. "Substantially identical" refers to an amino acid sequence or nucleic acid sequence exhibiting in order of increasing preference at least 75%, 80%, 85%, 90%, 95%, 98 or 99% identity to the phosphopantetheinyl transferase polypeptide sequence in SEQ ID NO:5, SEQ ID NO:7 or sequences encoding these polypeptides. Polypeptide or polynucleotide comparisons may be carried out using sequence analysis software, for example, the Sequence Analysis software package of the GCG Wisconsin Package (Accelrys, San Diego, Calif.) and MEGAlign (DNAStar, Inc., 1228 S. Park St., Madison, Wis. 53715). Such software matches similar sequences by assigning degrees of similarity or identity.

DNA Constructs

The invention provides DNA constructs comprising a heterologous promoter operably linked to a nucleic acid described herein. The selection of promoters, e.g., promoters that may be described as strongly expressed, weakly expressed, inducibly expressed, tissue-enhanced expressed (i.e., specifically or preferentially expressed in a tissue), organ-enhanced expressed (i.e., specifically or preferentially expressed in an organ) and developmentally-enhanced expressed (i.e., specifically or preferentially expressed during a particular stage(s) of development), is within the skill in the art. Similarly, the combining of a nucleic acid molecule as described above with a promoter is also within the skill in the art (see, e.g., Sambrook et al., 1989).

Promoters for use with the invention include, but are not limited to, promoters that function in bacteria, bacteriophages, fungi or plant cells. Useful promoters for bacterial expression are the lacZ, Sp6, T7, T5 or *E. coli* glgC promoters. Useful promoters for fungi include *Saccharomyces cerevisiae* Gall (West, et al. (1984)), *Saccharomyces pombe* nmt1 (Maundrell, K. (1990)), *Neurospora crassa* ccg-1 (Freitag M and Selker E U (2005)) and *Pichia methanolica* AUG1 (Invitrogen). Useful promoters for plants cells include the gamma zein Z27 promoter (see, for example, Lopes et al. (1995), L3 oleosin promoter (U.S. Pat. No. 6,433,252), barley PER1 promoter (Stacey et al., 1996), CaMV 35S promoter (Odell et al., 1985), the CaMV 19S (Lawton et al., 1987), nos (Ebert et al., 1987), Adh (Walker et al., 1987), sucrose synthase (Yang et al., 1990), actin (Wang et al., 1992), cab (Sullivan et al., 1989), PEPCase promoter (Hudspeth et al., 1989), or those associated with the R gene complex (Chandler et al., 1989). The Figwort Mosaic Virus (FMV) promoter (Richins et al., 1987), arcelin, tomato E8, patatin, ubiquitin, mannopine synthase (mas) and tubulin promoters are other examples of useful promoters.

There are a wide variety of plant promoter sequences which may be used to drive tissue-specific expression of polynucleotides encoding phosphopantetheinyl transferases in transgenic plants. Indeed, in particular embodiments of the invention, the promoter used is a seed specific promoter. Examples of such promoters include the 5' regulatory regions from such genes as napin (Kridl et al., 1991), phaseolin (Bustos, et al., 1989), soybean trypsin inhibitor (Riggs, et al., 1989), ACP (Baerson et al., 1993), stearoyl-ACP desaturase (Slocombe et al., 1994), soybean a' subunit of β-conglycinin (P-Gm7S alpha', see for example, Chen et al., 1986), *Vicia faba* USP (P-Vf.Usp, see for example, SEQ ID NO:1, 2, and 3, U.S. patent application Ser. No. 10/429,516), the globulin promoter (see for example Belanger and Kriz, (1991), soybean alpha subunit of P-conglycinin (7S alpha) (U.S. patent application Ser. No. 10/235,618, incorporated by reference) and *Zea mays* L3 oleosin promoter (P-Zm.L3, see, for example, Hong et al., 1997).

Promoters expressed in maize include promoters from genes encoding zeins, which are a group of storage proteins found in maize endosperm. Genomic clones for zein genes have been isolated (Pedersen et al., 1982; Russell et al., 1997) and the promoters from these clones, including the 15 kD, 16 kD, 19 kD, 22 kD and 27 kD genes, can be used. Other seed-expression enhanced promoters known to function in maize and in other plants include the promoters for the following genes: Waxy (granule bound starch synthase), Brittle and Shrunken 2 (ADP glucose pyrophosphorylase), Shrunken 1 (sucrose synthase), branching enzymes I and II, starch synthases, debranching enzymes, oleosins, glutelins, and BetlI (basal endosperm transfer layer). Other promoters useful in the practice of the invention that are known by one of skill in the art are also contemplated by the invention.

Moreover, transcription enhancers or duplications of enhancers can be used to increase expression from a particular promoter. Examples of such enhancers include, but are not limited to the Adh intron1 (Callis et al., 1987), a rice actin intron (McElroy et al., 1991; U.S. Pat. No. 5,641,876), sucrose synthase intron (Vasil et al., 1989), a maize HSP70 intron (also referred to as Zm.DnaK) (U.S. Pat. No. 5,424,412, Brown et al.) a TMV omega element (Gallie et al., 1999), the CaMV 35S enhancer (U.S. Pat. Nos. 5,359,142 & 5,196,525, McPherson et al.) or an octopine synthase enhancer (U.S. Pat. No. 5,290,924, Last et al.). As the DNA sequence between the transcription initiation site and the start of the coding sequence, i.e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, 1987). The choice of such sequences is at the discretion of those of skill in the art.

DNA constructs of the invention may include a sequence near the 3' end of the cassette that acts as a signal to terminate transcription from a heterologous nucleic acid and that directs polyadenylation of the resultant mRNA. These are commonly referred to as 3' untranslated regions or 3' UTRs. Some 3' elements that can act as transcription termination signals include those from the nopaline synthase gene (nos) of *Agrobacterium tumefaciens* (Bevan et al., 1983), a napin 3' untranslated region (Kridl et al., 1991), a globulin 3' untranslated region (Belanger and Kriz, 1991), 3' untranslated region from the Adr12 gene of soybean (auxin down regulated) (Wang et al., PCT Publication WO200250295) or one from a zein gene, such as Z27 (Lopes et al., 1995). Other 3' regulatory elements known to the art also can be used in the vectors of the invention.

A nucleic acid molecule as described herein can be cloned into any suitable vector and can be used to transform or transfect any suitable host. The selection of vectors and methods to construct them are commonly known to the art and are described in general technical references (see, in general, "Recombinant DNA Part D" (1987)). The vector will preferably comprise regulatory sequences, such as transcription and translation initiation and termination codons, which are specific to the type of host (e.g., bacterium, fungus, or plant) into which the vector is to be introduced, as appropriate and taking into consideration whether the vector is DNA or RNA.

Vectors that are circular or linear can be prepared to contain an entire nucleic acid sequence as described above or a portion thereof ligated to a replication system functional in a prokaryotic or eukaryotic host cell. Replication systems can be derived from ColE1, 2 mµ plasmid, λ phage, fl filamentous phage, *Agrobacterium* species (e.g., A. tumefaciens and A. rhizogenes), and the like.

In addition to the replication system and the inserted nucleic acid sequence, the vector can include one or more marker genes that allow for selection of transformed or transfected hosts. Marker genes include biocide resistance, such as resistance to antibiotics, heavy metals, herbicides, etc., complementation in an auxotrophic host to provide prototrophy, and the like.

The invention provides host cells comprising a nucleic acid molecule described herein, optionally in the form of a vector. Suitable hosts include plant, bacterial and fungal cells, including *Escherichia coli, Bacillus subtilis, Agrobacterium tumefaciens, Saccharomyces cerevisiae* and *Neurospora crassa. E. coli* hosts include TB-1, TG-2, DH5α, XL-Blue MRF' (Stratagene, Austin, Tex.), SA2821, Y1090 and TG02. Plant cells include, but not limited to, soybean, *Brassica campestris*, canola, oilseed rape, rapeseed, crambe, mustard, castor bean, peanut, sesame, cottonseed, linseed, safflower, oil palm, flax, sunflower, alfalfa, corn, wheat, barley, oats, rye, millet, sorghum, and rice.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Expression in a host cell may involve fermentation techniques known to one skilled in the art. The fermented host cell may be a prokaryote, such as *Escherichia coli*, or a eukaryote, such as the yeast *Saccharomyces cerevisiae*, or *Neurospora crassa*, a filamentous fungi. Examples of production of PUFA by fermentation include *Mortierella* (U.S. Pat. No. 6,319,698) and *Thraustochytriales* (U.S. Pat. No. 6,451,567).

It is contemplated that more than one gene may be introduced and propagated in a host cell through the use of episomal or integrated expression vectors. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced polynucleotides are expressed at the necessary levels to provide for synthesis of the desired products.

Polypeptides

The invention provides phosphopantetheinyl transferases encoded by nucleic acid molecules described herein. Polyketide synthases are enzyme complexes composed of multifunctional polypeptides that catalyze the synthesis of complex molecules from simple substrates in an iterative fashion. In *Moritella marina*, a PKS complex synthesizes DHA from malonyl-CoA and acetyl-CoA. To activate this complex, a phosphopantetheinyl transferase is required. The polypeptide preferably comprises an amino end and a carboxyl end. The polypeptide can comprise D-amino acids, L-amino acids or a mixture of D- and L-amino acids.

Alterations of the native amino acid sequence to produce variant polypeptides can be prepared by a variety of means known to those ordinarily skilled in the art. For instance, amino acid substitutions can be conveniently introduced into the polypeptides by changing the sequence of the nucleic acid molecule at the time of synthesis. Site-specific mutations can also be introduced by ligating into an expression vector a synthesized oligonucleotide comprising the modified sequence. Alternately, oligonucleotide-directed, site-specific mutagenesis procedures can be used, such as disclosed in Walder et al. (1986); Bauer et al. (1985); and U.S. Pat. Nos. 4,518,584 and 4,737,462.

It is within the skill of the ordinary artisan to select synthetic and naturally-occurring amino acids that effect conservative or neutral substitutions for any particular naturally-occurring amino acids. The ordinarily skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids is relatively hydrophobic when incorporated into a polypeptide, but glycines lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine and, optionally, tyrosine. Additionally, the ordinarily skilled artisan can readily group synthetic amino acids with naturally-occurring amino acids.

If desired, the polypeptides can be modified, for instance, by glycosylation, amidation, carboxylation, or phosphorylation, or by the creation of acid addition salts, amides, esters, in particular C-terminal esters, and N-acyl derivatives of the polypeptides of the invention. The polypeptides also can be modified to create protein derivatives by forming covalent or noncovalent complexes with other moieties in accordance with methods known in the art. Covalently-bound complexes can be prepared by linking the chemical moieties to functional groups on the side chains of amino acids comprising the polypeptides, or at the N— or C-terminus. Desirably, such modifications and conjugations do not adversely affect the activity of the polypeptides (and variants thereof). While such modifications and conjugations can have greater or lesser activity, the activity desirably is not negated and is characteristic of the unaltered polypeptide.

The polypeptides (and fragments, variants and fusion proteins) can be prepared by any of a number of conventional techniques. The polypeptide can be isolated or substantially purified from a naturally occurring source or from a recombinant source. For instance, in the case of recombinant proteins, a DNA fragment encoding a desired protein can be subcloned into an appropriate vector using well-known molecular genetic techniques (see, e.g., Maniatis et al., 1989) and other references cited herein under "EXAMPLES"). The fragment can be transcribed and the protein subsequently translated in vitro. Commercially available kits also can be employed (e.g., such as manufactured by Clontech, Mountain View, Calif.; Amersham Life Sciences, Inc., Arlington Heights, Ill.; Invitrogen, Carlsbad, Calif. and the like). The polymerase chain reaction optionally can be employed in the manipulation of nucleic acids.

Polypeptides can be synthesized using an automated peptide synthesizer in accordance with methods known in the art. Alternately, the polypeptide (and fragments, variants, and fusion proteins) can be synthesized using standard peptide synthesizing techniques well-known to those of ordinary skill in the art (e.g., as summarized in Bodanszky (1984)). In particular, the polypeptide can be synthesized using the procedure of solid-phase synthesis (see, e.g., Merrifield, 1963; Barany et al., 1987; and U.S. Pat. No. 5,424,398). If desired, this can be done using an automated peptide synthesizer. Removal of the t-butyloxycarbonyl (t-BOC) or 9-fluorenyl-methyloxycarbonyl (Fmoc) amino acid blocking groups and separation of the protein from the resin can be accomplished by, for example, acid treatment at reduced temperature. The polypeptide-containing mixture then can be extracted, for instance, with diethyl ether, to remove non-peptidic organic compounds, and the synthesized protein can be extracted from the resin powder (e.g., with about 25% w/v acetic acid). Following the synthesis of the polypeptide, further purification (e.g., using HPLC) optionally can be done in order to eliminate any incomplete proteins, polypeptides, peptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation, or through genetic means known to the art. In this regard, this invention also provides a fusion protein comprising the polypeptide (or fragment thereof) or variant thereof and one or more other polypeptides/protein(s) having any desired properties or effector functions.

Assays for the production and identification of specific proteins are based on various physical-chemical., structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches can be used to achieve even greater specificity such as western blotting in which antibodies are used to locate individual gene products that have been separated by electrophoretic techniques. Additional techniques can be used to absolutely confirm the identity of the product of interest such as evaluation by amino acid sequencing following purification. Although these are among the most common, other procedures can also be used.

Assay procedures can identify the expression of proteins by their functionality, particularly where the expressed protein is an enzyme capable of catalyzing chemical reactions involving specific substrates and products. For example, in plant extracts these reactions can be measured by providing and quantifying the loss of substrates or the generation of products of the reactions by physical and/or chemical procedures.

In many cases, the expression of a gene product is determined by evaluating the phenotypic results of its expression. Such evaluations may be simply as visual observations, or may involve assays. Such assays can take many forms, such as analyzing changes in the chemical composition, morphology, or physiological properties of the plant. Chemical composition may be altered by expression of genes encoding enzymes or storage proteins that change amino acid composition and these changes can be detected by amino acid analysis, or by enzymes that change starch quantity, which can be analyzed by near infrared reflectance spectrometry or by enzymes that change oil composition, which can be detected by gas chromatography. Morphological changes may include greater stature or thicker stalks.

The nucleic acid molecules, DNA constructs and polypeptides of this invention can be used in agricultural methods and various screening assays. For example, a nucleic acid molecule can be used to express phosphopantetheinyl transferase via a vector in a host cell, to detect mRNA transcripts encoding phosphopantetheinyl transferase in a biological sample, to detect a genetic alteration in a gene encoding phosphopantetheinyl transferase via a Southern blot, to suppress phosphopantetheinyl transferase, or to up-regulate phosphopantetheinyl transferase. The polypeptides can be used to compensate for deficiencies in phosphopantetheinyl transferase or for the presence of a mutated phosphopantetheinyl transferase having reduced or no activity in a plant, or to treat excessive levels of substrates, whether direct or indirect, for phosphopantetheinyl transferase in a plant. Alternatively, the polypeptides can be used to screen agents for the ability to modulate their activity. The antibodies can be used to detect and isolate the respective polypeptides as well as decrease the availability of such polypeptides in vivo.

Plant Transformation

In a preferred embodiment of the invention, a transgenic plant expressing the desired protein or proteins is produced. Various methods for the introduction of a desired polynucleotide sequence encoding the desired protein into plant cells are known to the art, including: (1) physical methods such as microinjection, electroporation, and microparticle-mediated delivery (biolistics or gene gun technology); (2) virus-mediated delivery; and (3) *Agrobacterium*-mediated transformation.

The most commonly used methods for transformation of plant cells are the *Agrobacterium*-mediated DNA transfer process and the biolistics or microprojectile microparticle bombardment mediated process. Typically, nuclear transformation is desired but where it is desirable to specifically transform plastids, such as chloroplasts or amyloplasts, plant plastids may be transformed utilizing a microparticle-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species, as further elaborated, for example, in U.S. Pat. No. 6,265,638 to Bidney et al., the disclosures of which are hereby incorporated herein by reference.

*Agrobacterium*-mediated genetic transformation of plants involves several steps. The first step, in which the virulent *Agrobacterium* and plant cells are first brought into contact with each other, is generally called "inoculation". Inoculation is preferably accompanied by some method of injury to some of the plant cells, which releases plant cellular constituents, such as coumaryl alcohol, sinapinate (which is reduced to acetosyringone), sinapyl alcohol, and coniferyl alcohol, that activate virulence factors in the *Agrobacterium*. Following the inoculation, the *Agrobacterium* and plant cells/tissues are permitted to grow together for a period of several hours to several days or more under conditions suitable for growth and T-DNA transfer. This step is termed "co-culture". Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microparticle bombardment (U.S. Pat. No. 5,550,318 (Adams et al.); U.S. Pat. No. 5,538,880 (Lundquist et. al.), U.S. Pat. No. 5,610,042 (Chang et al.); and PCT WO 95/06128 (Adams et al.); each of which is specifically incorporated herein by reference in its entirety), microscopic particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microparticle bombardment techniques are widely applicable, and may be used to transform virtually any plant species. Examples of species that have been transformed by microparticle bombardment include monocot species such as maize (International Publication No. WO 95/06128 (Adams et al.)), barley, wheat (U.S. Pat. No. 5,563,055 (Townsend et al.) incorporated herein by reference in its entirety), rice, oat, rye, sugarcane, and sorghum; as well as a number of dicots including tobacco, soybean (U.S. Pat. No. 5,322,783 (Tomes et al.), incorporated herein by reference in its entirety), sunflower, peanut, cotton, tomato, and legumes in general (U.S. Pat. No. 5,563,055 (Townsend et al.) incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to β-glucuronidase (GUS), green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061 (Barry, et al.), U.S. Pat. No. 5,633,435 (Barry, et al.), and U.S. Pat. No. 6,040,497 (Spencer, et al.) and aroA described in U.S. Pat. No. 5,094,945 (Comai) for glyphosate tolerance; a polynucleotide molecule encoding bromoxynil nitrilase (Bxn) described in U.S. Pat. No. 4,810,648 (Duerrschnabel, et al.) for Bromoxynil tolerance; a polynucleotide molecule encoding phytoene desaturase (CertI) described in Misawa et al., (1993); Misawa et al. (1994) for norflurazon tolerance; a polynucleotide molecule encoding acetohydroxyacid synthase (AHAS, aka ALS) described in Sathasiivan et al. (1990) for tolerance to sulfonylurea herbicides; and both the pat gene described in Wohlleben, et al., (1988) and bar gene described in DeBlock, et al. (1987), each of which provides glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

This invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves. The Tomes et al. '783 patent, cited above, describes a method of treatment with a cytokinin followed by incubation for a period sufficient to permit undifferentiated cells in cotyledonary node tissue to differentiate into meristematic cells and to permit the cells to enter the phases between the GI and division phases of development, which is stated to improve susceptibility for transformation.

Any suitable plant culture medium can be used. Suitable media include but are not limited to MS-based media (Murashige and Skoog, 1962) or N6-based media (Chu et al., 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

After a DNA construct is stably incorporated in transgenic plants and confirmed to be operable, it can be introduced into other plants of the same or another sexually compatible species by sexual crossing. Any of a number of standard breeding techniques can be used, depending upon the species to be crossed. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

Backcrossing is herein defined as the process including the steps of: (a) crossing a plant of a first genotype containing a desired gene, DNA sequence or element to a plant of a second genotype lacking said desired gene, DNA sequence or element; (b) selecting one or more progeny plant containing the desired gene, DNA sequence or element; (c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

Seeds, Meal, Oil and Products Comprising Seeds, Meal and Oil

This invention also provides a container of over about 1000, more preferably about 20,000, and even more preferably about 40,000 seeds where over about 10%, more preferably about 25%, more preferably about 50%, and even more preferably about 75% or more preferably about 90% of the seeds are seeds derived from a plant of this invention.

This invention also provides a container of over about 10 kg, more preferably about 25 kg, and even more preferably about 50 kg seeds where over about 10%, more preferably about 25%, more preferably about 50%, and even more preferably about 75% or more preferably about 90% of the seeds are seeds derived from a plant of this invention.

Any of the plants or parts thereof of this invention may be harvested and, optionally, processed to produce a feed, meal, or oil preparation. A particularly preferred plant part for this purpose is harvested grain, but other plant parts can be harvested and used for stover or silage. Methods to produce feed, meal, and oil preparations are known in the art. See, for example, U.S. Pat. Nos. 4,957,748; 5,100,679; 5,219,596; 5,936,069; 6,005,076; 6,146,669; and 6,156,227. The grain or meal of this invention may be blended with other grains or meals.

Methods

The present invention provides a method for providing transgenic plants with an increased content of DHA or EPA. This method may include, for example, introducing DNA encoding phosphopantetheinyl transferase as well as a PKS complex into plant cells and regenerating plants with increased DHA or EPA content from the transgenic cells.

More specifically, the invention provides a method of making a plant oil containing DHA or EPA comprising the steps of (a) growing a plant comprising the host cell transformed with a DNA construct comprising a heterologous promoter operably linked to a DNA molecule encoding a polypeptide having phosphopantetheinyl transferase activity, wherein the DNA molecule is selected from the group consisting of: a polynucleotide hybridizing to SEQ ID NO:6 or SEQ ID NO:8, or a complement thereof, under conditions of 5×SSC, 50% formamide and 42° C.; a polynucleotide encoding the polypeptide sequence of SEQ ID NO:5 or SEQ ID NO:7; a polynucleotide encoding a polypeptide with at least 75% sequence identity to a polypeptide sequence of SEQ ID NO:5 or SEQ ID NO:7; a polynucleotide encoding the polypeptide of SEQ ID NO: 1; and a polynucleotide encoding the polypeptide of SEQ ID NO:3 wherein the host cell further comprises a polyketide synthase; (b) producing seed; and (c) processing the seed to obtain oil.

The present invention further provides a method for providing transgenic plants which may contain elevated levels of DHA or EPA, wherein said elevated levels are greater than levels found in non-transformed plants.

For dietary supplementation, the purified PUFAs, transformed plants or plant parts, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

As used herein, "edible composition" is defined as compositions which may be ingested by a mammal such as foodstuffs, nutritional substances and pharmaceutical compositions. As used herein "foodstuffs" refer to substances that can be used or prepared for use as food for a mammal and include substances that may be used in the preparation of food (such as frying oils) or food additives. For example, foodstuffs include animals used for human consumption or any product therefrom, such as, for example, eggs. Typical foodstuffs include but are not limited to beverages, (e.g., soft drinks, carbonated beverages, ready to mix beverages), infused foods (e.g. fruits and vegetables), sauces, condiments, salad dressings, fruit juices, syrups, desserts (e.g., puddings, gelatin, icings and fillings, baked goods and frozen desserts such as ice creams and sherbets), soft frozen products (e.g., soft frozen creams, soft frozen ice creams and yogurts, soft frozen toppings such as dairy or non-dairy whipped toppings), oils and emulsified products (e.g., shortening, margarine, mayonnaise, butter, cooking oil, and salad dressings) and intermediate moisture foods (e.g., rice and dog foods).

Furthermore, edible compositions described herein can also be ingested as an additive or supplement contained in foods and drinks. These can be formulated together with a nutritional substance such as various vitamins and minerals and incorporated into substantially liquid compositions such as nutrient drinks, soymilks and soups; substantially solid compositions; and gelatins or used in the form of a powder to be incorporated into various foods. The content of the effective ingredient in such a functional or health food can be similar to the dose contained in a typical pharmaceutical agent.

The purified PUFAs, transformed plants or plant parts may also be incorporated into animal, particularly livestock, feed. In this way, the animals themselves may benefit from a PUFA rich diet, while human consumers of food products produced from such livestock may benefit as well.

For pharmaceutical use (human or veterinary), the compositions may generally be administered orally but can be administered by any route by which they may be successfully absorbed, e.g., parenterally (i.e. subcutaneously, intramuscularly or intravenously), rectally, vaginally or topically, for example, as a skin ointment or lotion. The PUFAs, transformed plants or plant parts of the present invention may be administered alone or in combination with a pharmaceutically acceptable carrier or excipient. Where available, gelatin capsules are the preferred form of oral administration. Dietary supplementation as set forth above can also provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, found in PCT publication WO 96/33155. The preferred esters are the ethyl esters. As solid salts, the PUFAs also can be administered in tablet form. For intravenous administration, the PUFAs or derivatives thereof may be incorporated into commercial formulations such as Intralipids.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Cloning of Phosphopantetheinyl Transferase Sequences

Three bacterial phosphopantetheinyl transferases were cloned. The amino acid sequence of the phosphopantetheinyl transferase (Ppt) from *Shewanella* SCRC-2738 (SEQ ID NO:17) was used to search public databases for novel ppts that function in EPA or DHA biosynthesis. This search yielded putative ppts from *Shewanella oneidensis* MR-1 (SEQ ID NO:1) (So-ppt) and *Colwellia psychrerythraea* (SEQ ID NO:3) (Cp-ppt). The nucleic acid sequences of ppts from *Shewanella oneidensis* MR-1 (SEQ ID NO:2) and *Colwellia psychrerythraea* (SEQ ID NO:4) were cloned using the Expand High Fidelity PCR system (Roche, Applied Science, Indianapolis, Ind.) with the following primer pairs:

```
Shew new
                                        (SEQ ID NO: 9)
5': tcgagctcgcatatgaagattgagcttttttttatacc Shew
                                        (SEQ ID NO: 10)
3': tcttaattaattagtcagccaaactagccgc Colwe new
                                        (SEQ ID NO: 11)
5': tcgagctcgcatatgacttcttttctcaatctg Colwe
                                        (SEQ ID NO: 12)
3': tcttaattaattagatttcctgataaccaagtag.
```

Figure 2:
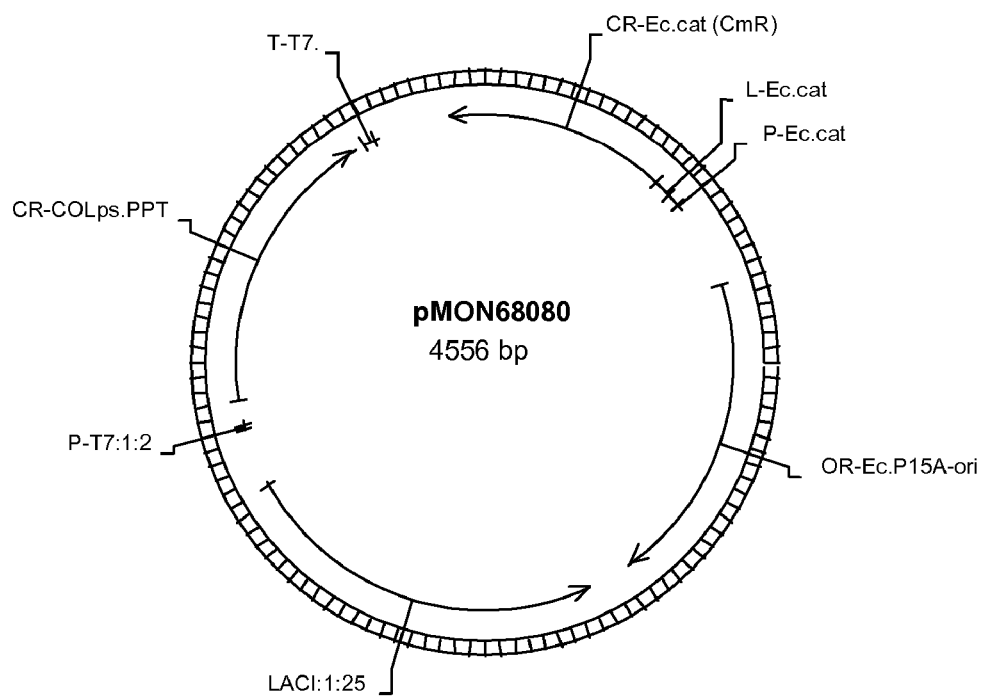
FIG. 2 shows a map of vector pMON68080.

The genes were amplified for 25 cycles with the melting temperature set at 55° C. and 52° C. for the *Shewanella* and *Colwellia* ppts, respectively. The PCR products were digested with NdeI and PacI and ligated into NdeI- and PacI-digested Novagen pACYC-Duet-1 (EMD Biosciences, Darmstadt, Germany) resulting in the formation of pMON68081 (FIG. 1) and pMON68080 (FIG. 2) respectively.

To clone the *Moritella marina* phosphopantetheinyl transferase (Mm-ppt), the nucleotide sequences of the *Shewanella* SCRC-2738 ppt (SEQ ID NO:18), the *C. psychrerythraea* ppt, and the *S. oneidensis* MR-1 ppt were aligned to identify the most conserved region of these sequences. A region of conserved nucleotide sequence in So-ppt (bps 425-635 of SEQ ID NO: 2) and Cp-ppt (bps 389-596 of SEQ ID NO: 4) was identified by this alignment and sequence in this region was chosen to generate probes using genomic DNA from *C. psychrerythraea* and *S. oneidensis* MR-1 as template DNAs and the primers below:

```
Shewanella F1
taggtgtcgatattgagcggg      (SEQ ID NO: 13)

Shewanella R1
tcaaaggcaaaggattttaac      (SEQ ID NO: 14)

Colwellia F1
tcggttgtgatgttgaaaatac     (SEQ ID NO: 15)

Colwellia R1
ttaaaactaaaatcagcgagt.     (SEQ ID NO: 16)
```

Digoxigenin-labeled probes were generated using PCR DIG Probe Synthesis Kit (Roche) according to the manufacturers protocol for 30 cycles of 30 s each at 94° C., 55 ° C., and 65° C. followed by a 7 min incubation at 65° C. and subsequent incubation at 4° C. The digoxigenin-labeled probes were used in a Southern hybridization to probe for homologous sequences in *M. marina* total genomic DNA with *S. oneidensis* MR-1 and *C. psychrerythraea* as positive controls. The hybridization was performed at 30° C. using DIG Easy Hyb (Roche) according to the manufacturer's protocol. The filter was washed twice using 0.5×SSC, 0.1% SDS at room temperature. Dig-labeled probes were visualized using the Anti-Digoxigenin-AP, Fab fragments and Dig Wash and Block Buffer Set (Roche) according to the manufacturers protocol.

The strongest signals from the *M. marina* DNA were obtained using the *Colwellia* probe. In some cases these signals coincided with weak signals obtained from *M. marina* DNA using the *Shewanella* probe.

Based on the Southern hybridization experiment, BglII- and PstI-digests of *M. marina* DNA were chosen to clone the hybridizing fragments. Total genomic DNA was digested with BglII or PstI, size-fractionated on an agarose gel and the appropriately sized fragment excised. The DNA fragments were purified using the Qiagen Gel Extraction kit (Qiagen, Valencia, Calif.). Aliquots of fractionated DNA were run on an agarose gel and blotted onto a nylon membrane (Roche, Mannheim, Germany) using a Turboblotter (Schleicher & Schuell, Keene, N. H.), according to the manufacturers protocol. The target fragment was identified by a Southern hybridization using the *Colwellia* probe.

The BglII fraction 5 and PstI fraction 4 were chosen to generate a partial library in pSP72 (Promega, Madison, Wis.). These libraries were transformed into *Escherichia coli* DH5α and pools of clones were aliquoted into the wells of a 96-well plate for over night growth. Culture aliquots were spun down, the supernatant was discarded, and the cell pellets were resuspended in 10 µl 10% SDS solution. The cell pellets were heated for 1 min to 100° C. and spotted on nylon membranes (Roche). DNA was denatured by 5 min incubation in 0.5 M NaOH, containing 1.5 M NaCl, neutralized by 5 min incubation in 0.5 M Tris/HCl, pH 7.6 containing 1.5 M NaCl, washed for 5 min in 2×SSC, and fixed by 1 min UV incubation in a Stratagene UV-Stratalinker 2400 (Stratagene, La Jolla, Calif.) according to the manufacturers protocol. The blot was probed with the *Colwellia* ppt probe. Positive signals were traced back to the well of origin and an aliquot from those wells was plated in order to obtain single colonies. Those single colonies were inoculated into 250 µl LB containing 100 mg/l carbampicillin. Cells were grown and the hybridization procedure described above was repeated to identify wells containing single positive clones. Positive clones were grown and plasmid DNA was isolated and digested with BglII, PvuII, PstI, or SalI. These digests were used in a Southern hybridization to confirm positive clones. At this point all remaining clones were found to be positive.

Three of the final clones (two BglII clones and one PstI clone) were chosen for DNA sequence analysis. Bioinformatics analysis of the complete sequence revealed that the PstI clone contained only a partial Mm-ppt, while the BglII clones contained the complete open reading frame. The complete DNA sequence of all three clones was assembled in one contig. One BglII clone was chosen for further cloning experiments (pMON96400). The putative amino acid sequence of the Mm-ppt is shown in SEQ ID NO:5 if the start codon is TTG (referred to as Mm-ppt long). An alternative start codon using Met is found at amino acid 43 of SEQ ID NO:5 (yielding a polypeptide referred to as Mm-ppt short SEQ ID NO:7). The nucleic acid sequence of Mm-ppt long is SEQ ID NO:6. The nucleic acid sequence of Mm-ppt short is shown in SEQ ID NO:8. A comparison of the amino acid relatedness of the Ppts of the invention is shown in Table 1.

TABLE 1

Amino acid sequence identity of phosphopantetheinyl transferases

| | *Colwellia psychrerythraea* | *Shewanella* SCRC 2738 | *Schewanella oneidensis* MRI |
|---|---|---|---|
| *Moritella marina* (long) | 60.9% | 31.5% | 30.0% |
| *Colwellia psychrerythraea* | | 32.4% | 33.5% |
| *Shewanella* SCRC 2738 | | | 46.6% |

Example 2

Expression of Phosphopantetheinyl Transferase Sequences in *Escherichia coli*

Figure 3:
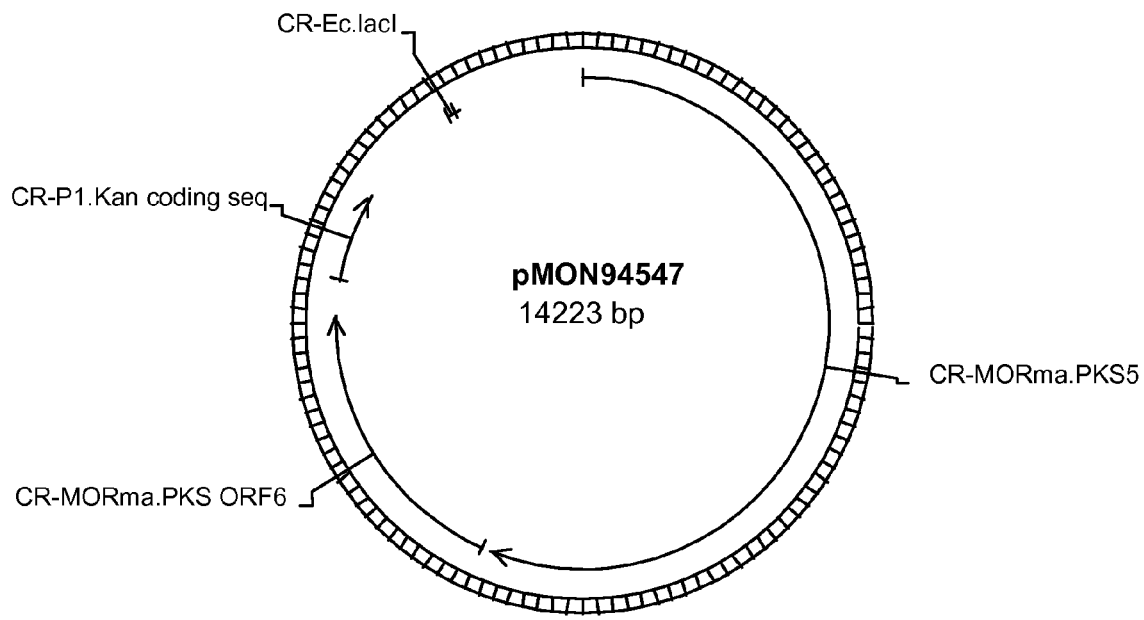
FIG. 3 shows a map of vector pMON94547.
Figure 4:
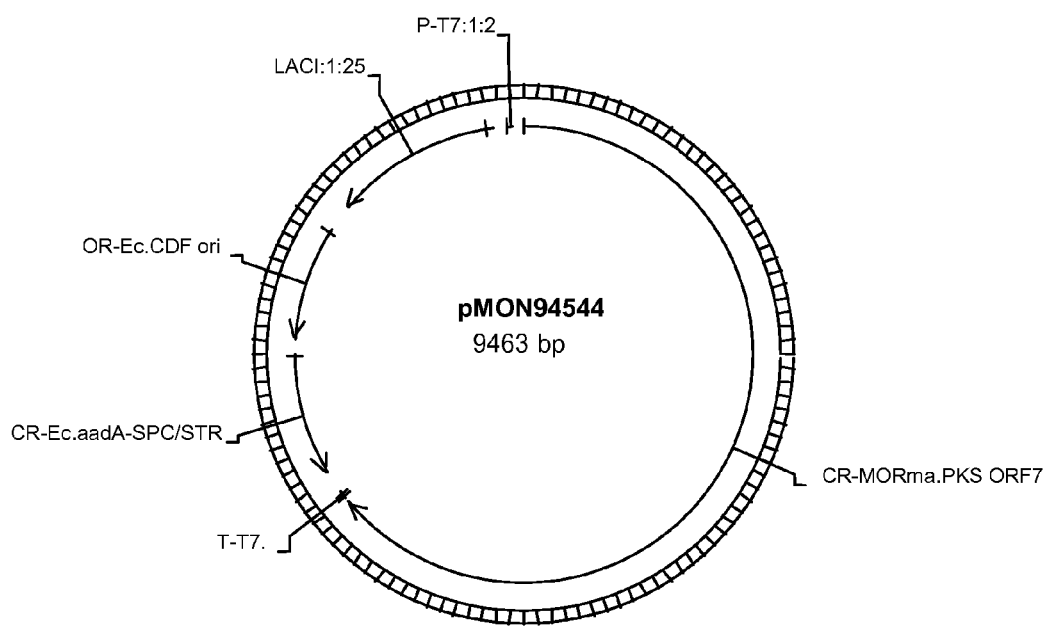
FIG. 4 shows a map of vector pMON94544.
Figure 5:
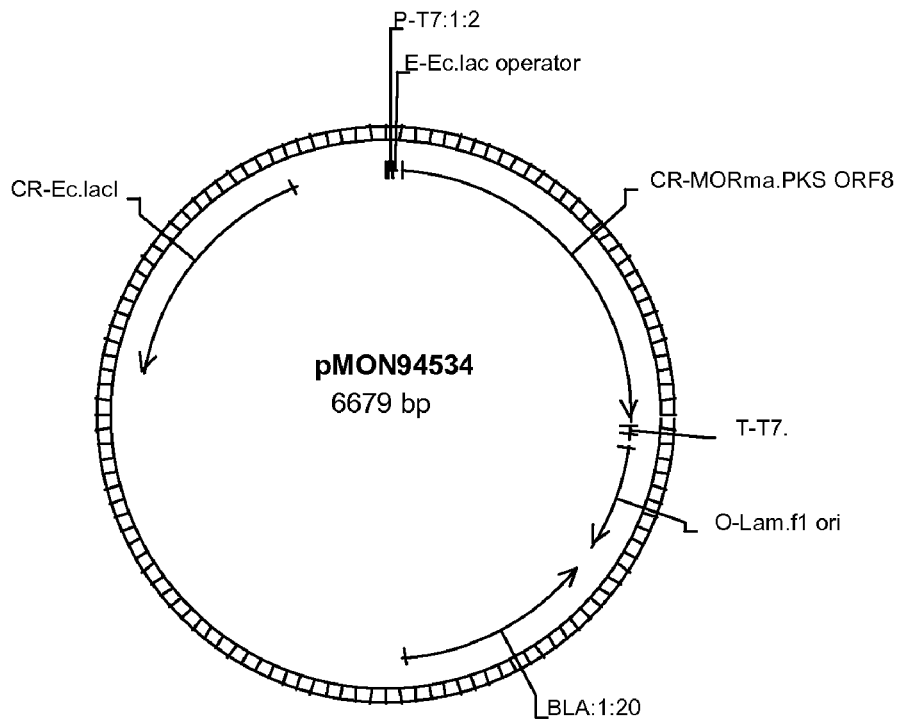
FIG. 5 shows a map of vector pMON94534.

To demonstrate functionality of the ppts described in Example 1, the *Moritella marina* polyketide synthase (PKS) genes were cloned into the Novagen pDUET vectors (EMD, Biosciences, Darmstadt, Germany), a set of 4 compatible *E. coli* expression vectors. This PKS consists of 4 polypeptides encoded by the nucleic acids orf5 (SEQ ID NO:20), orf6 (SEQ ID NO:22), orf7 (SEQ ID NO:24) and orf8 (SEQ ID NO:26), which are described as orf6, orf7, orf8, and orf9 in U.S. Pat. No. 6,140,486, respectively. The expression vectors pMON94547 (Orf5 and Orf6) (FIG. 3), pMON94544 (Orf7) (FIG. 4) and pMON94534 (Orf8) (FIG. 5) were constructed using 3 of the pDUET vectors. The fourth pDUET vector was used for ppt expression.

Figure 6:
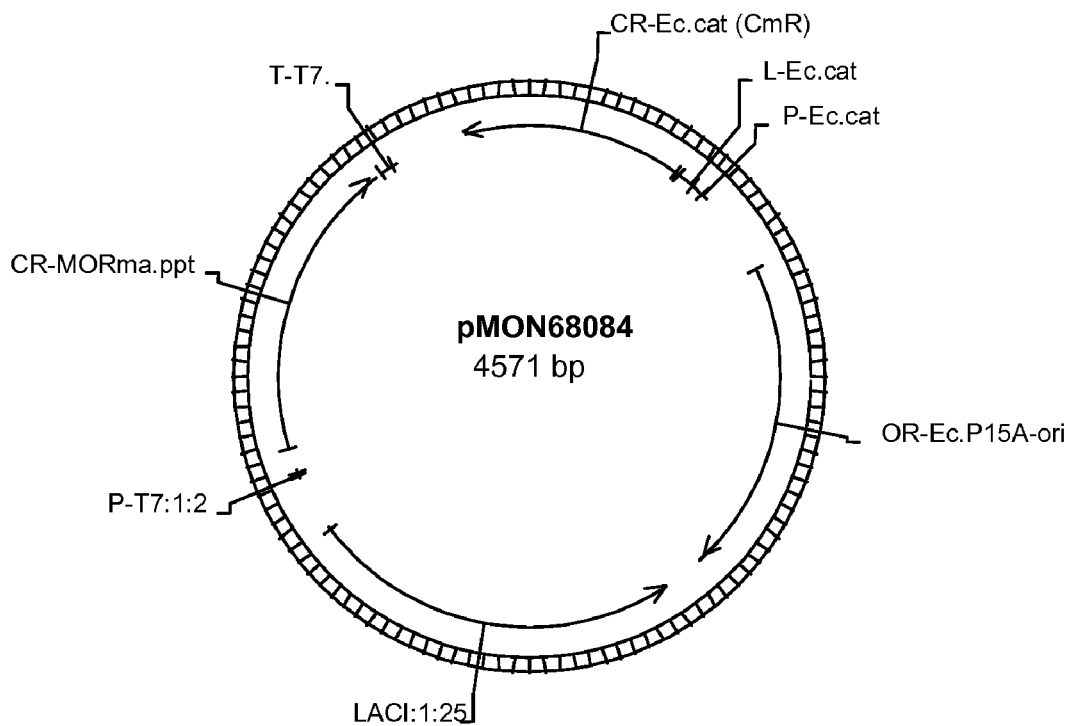
FIG. 6 shows a map of vector pMON68084.
Figure 7:
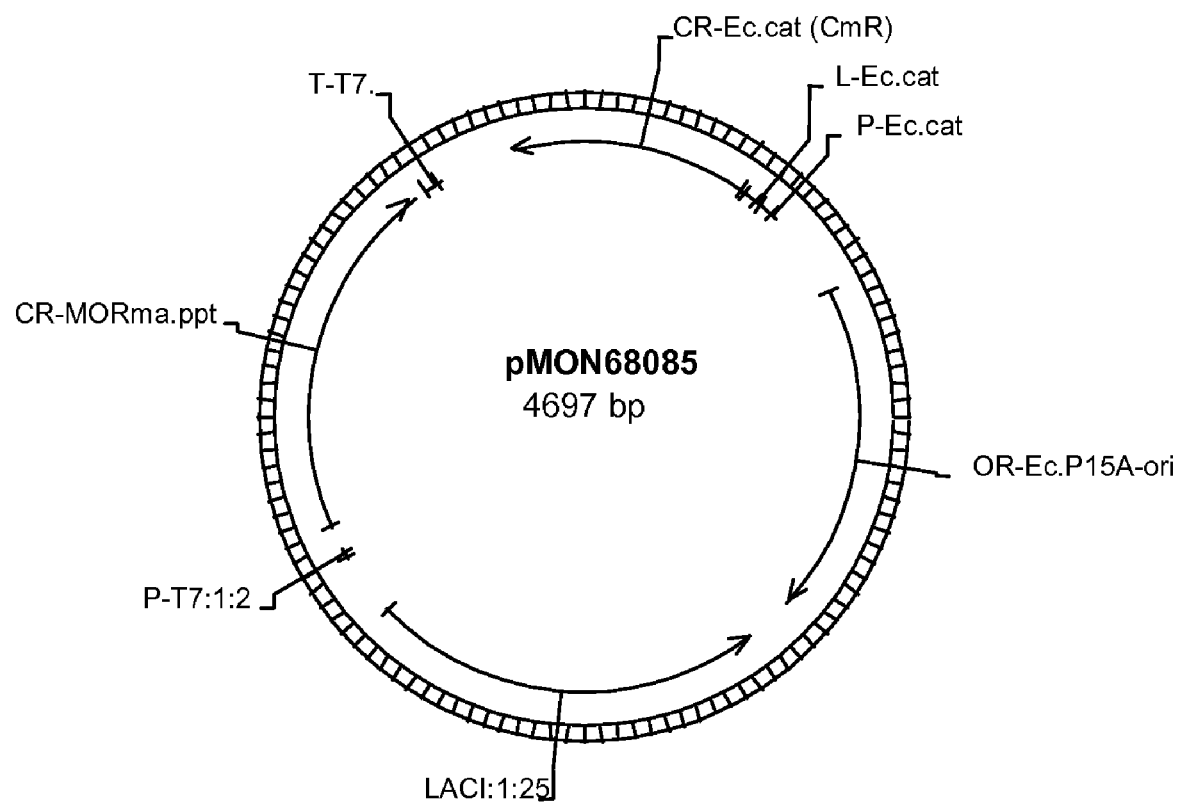
FIG. 7 shows a map of vector pMON68085.

To obtain an enzymatically active PKS, the Orf5 expression product requires pantethenylation, which is catalyzed by the Ppt. Each of the bacterial ppts was cloned into pACYC-DUET-1. The construction of pMON68081 and pMON68080 is described in Example 1. Similarly the two different putative *M. marina* ppts, Mm-ppt short or Mm-ppt long, were cloned into the same base vector as the *Colwellia* and the *Shewanella* ppts to yield pMON68084 (FIG. 6) and pMON68085 (FIG. 7), respectively. The Mm-ppt long PCR™ primer (SEQ ID NO:27) changed the putative TTG start to an ATG. Each ppt is then expressed together with the *M. marina* PKS genes in *E. coli*, incubated for 24 h, and the lyophilized *E. coli* cells are methylated directly with sulfuric acid/methanol, and the fatty acid methyl esters are analyzed for EPA and DHA content by gas chromatography. The results are shown below in Table 2.

TABLE 2

| Gene combination | DHA Produced |
|---|---|
| PKS only | No |
| PKS + Mm-ppt long | Yes |
| PKS + Mm-ppt short | Yes |
| PKS + So-ppt | Yes |
| PKS + Cp-ppt | Yes |
| PKS − Orf8 + Cp-ppt | No |

Co-expression of the complete *Moritella marina* PKS with any of the tested phosphopantetheinyl transferases in *E. coli* resulted in the accumulation of DHA, while expression of the *M. marina* PKS without co-expression of a Ppt did not result in DHA accumulation. Coexpression of the Cp-ppt with an incomplete PKS (missing Orf8) also did not result in DHA accumulation. These results demonstrate that all PPTs tested pantothenylated the *M. marina* PKS resulting in the formation of an active multi enzyme complex.

It has been demonstrated that Orf7 (Orf8 in U.S. Pat. No. 6,140,486) controls the chain length in the final product of PUFA-producing PKSs. The PKS of *Shewanella putrefaciens* produces EPA. In experiments in *E. coli* containing the *S. putrefaciens* PKS cluster, an orf7 deletion mutant produced DHA when complemented with *Moritella marina* orf7. The Ppt used to activate the PKS does not change the product, therefore the Ppts of this invention are used to produce EPA when combined with an EPA-producing PKS and DHA when combined with a DHA-producing PKS.

Example 3

Expression of Phosphopantetheinyl Transferase Sequences in Plants

To demonstrate the ability of the *M. marina* PKS, including the *M. marina* ppt, to synthesize DHA in plants, several plant expression cassettes were generated. The genes for orf5-8 were modified for expression in dicotyledonous plants. It is known that non-endogenous protein-encoding sequences may not express well in plants (U.S. Pat. No. 5,880,275, herein incorporated by reference). Therefore, using the native PKS polypeptide sequences for Orfs5-8 (SEQ ID NOs: 19, 21, 23, and 25), artificial protein-encoding polynucleotide sequences were designed and constructed by 1) using a codon usage bias similar to that of highly expressed soybean proteins, and by 2) removal of RNA destabilizing elements previously characterized and known to affect mRNA stability in planta (U.S. Pat. No. 5,880,275) and by introducing a Kozak sequence prior to the ATG start codon (Joshi et al., 1997). The resulting modified polynucleotide sequences encode polypeptides identical in sequence to the native polypeptides.

Figure 8:
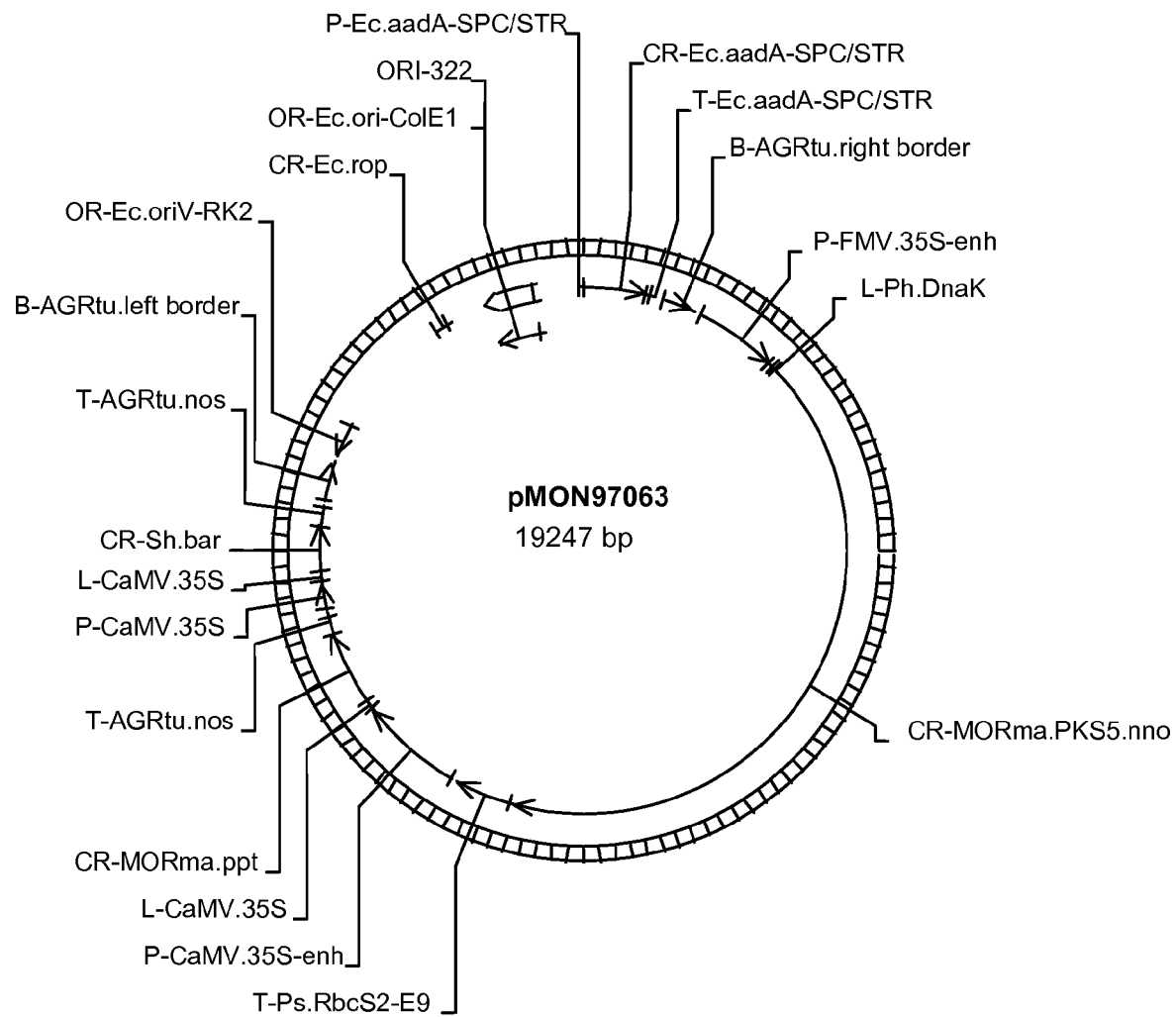
FIG. 8 shows a map of vector pMON97063.
Figure 9:
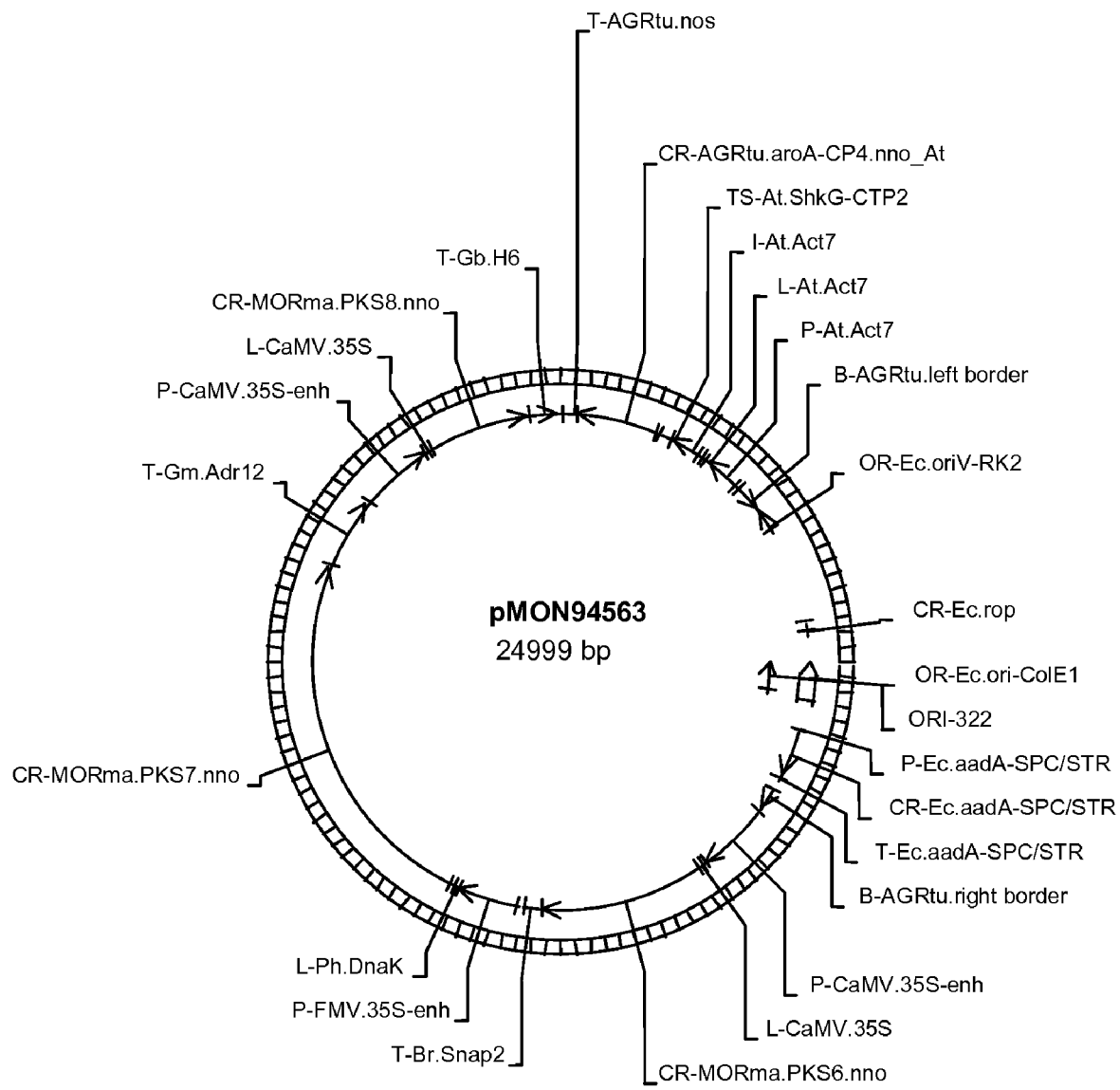
FIG. 9 shows a map of vector pMON94563.
Figure 10:
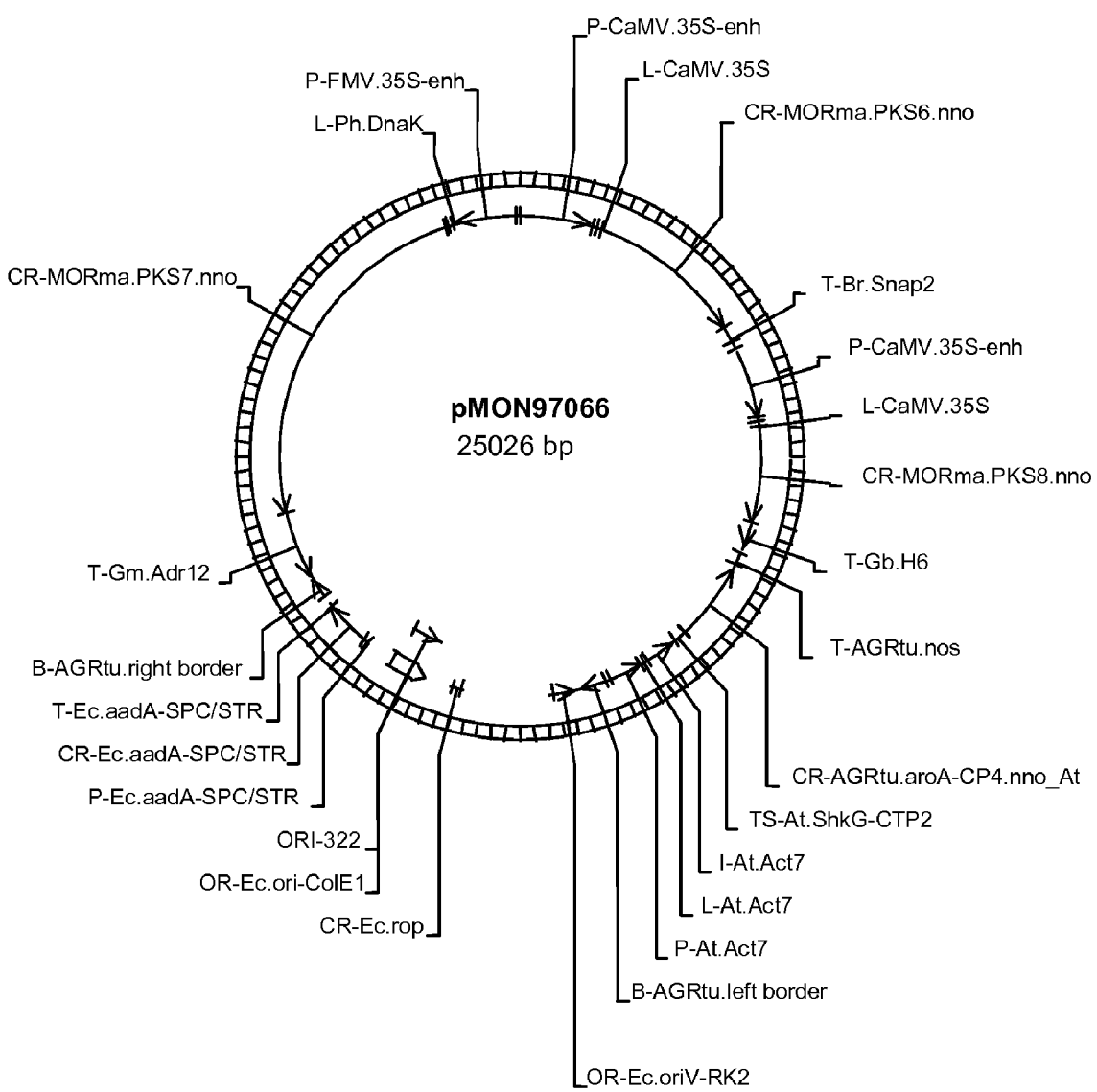
FIG. 10 shows a map of vector pMON97066.

The binary vector pMON97063 (FIG. 8) contains the expression cassettes for orf5 (codon-modified, SEQ ID NO:28) (under the control of the FMV.35S-enh promoter with the L-Ph.DnaK leader) and Mm-ppt short (SEQ ID NO:8) (under the control of the CaMV35S-enh promoter and the L-CaMV35S leader). This vector carries the Bar gene as selectable marker. The binary vector pMON94563 (FIG. 9) was generated by cloning of the expression cassettes for orf6 (codon-modified, SEQ ID NO:29) (under the control of the CaMV35S-enh promoter with the L-CaMV35S leader) orf7 (codon-modified, SEQ ID NO:30) (under the control of the FMV35S-enh promoter with the L-Ph.DnaK leader), and orf8 (codon-modified, SEQ ID NO:31) (under the control of the CaMV35S-enh promoter with the L-CaMV35S leader). pMON94563 carries the CP4 marker which provides glyphosate resistance. The binary vector pMON97066 (FIG. 10) contains the same expression cassettes as pMON94563, but with the orf7 cassette preceding the orf6 cassette instead of following it. All constructs were sequence verified by DNA sequencing.

The binary vector pairs pMON97063 and pMON94563 or pMON97063 and pMON97066 are cotransformed into *Arabidopsis thaliana* using *Agrobacterium*-mediated transformation. Plants are regenerated and leaf material of the transformed R1 *Arabidopsis* plants and R2 seed of these plants is analyzed for fatty acid content and composition.

Figure 11:
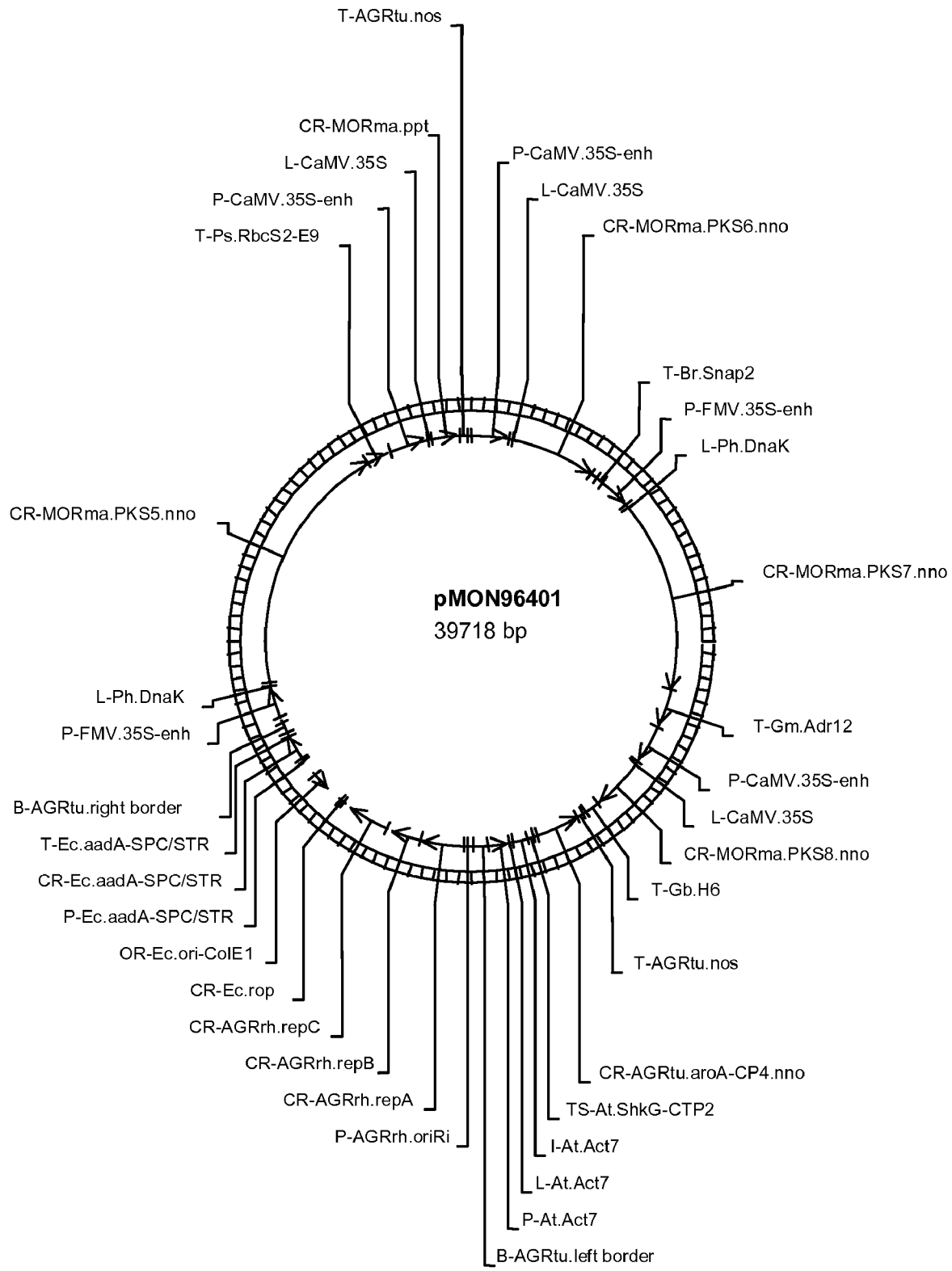
FIG. 11 shows a map of vector pMON96401.

To generate a single multi gene binary vector harboring all 4 PKS genes and the ppt the low copy number binary vector pMON83934 was digested with HindIII and NotI and ligated with a polylinker consisting of the DNA oligomers MCS-3 (SEQ ID NO:32) and MCS-4 (SEQ ID NO:33). The resulting vector was designated pMON68091. The expression cassettes for orf6, orf7, orf8 and the CP4 selectable marker were excised by HindIII /BsiWI digest from pMON94563 and ligated into HindIII/BsiWI-digested pMON68091. The resulting binary vector is digested with AscI and BsiWI and ligated with the expression cassettes containing orf5 and Mm-ppt from pMON97063 excised by BsiWI/AscI digest. The resulting binary vector, pMON96401 (FIG. 11), is transformed via *Agrobacterium*-mediated transformation into *Arabidopsis thaliana* and soybean. Plants are regenerated and leaf and seed material from these plants are analyzed for fatty acid content and composition.

48 R1 events containing pMON96401 were generated in *Arabidopsis*. Mature R2 seed from this study was analyzed by gas chromatography. 9 of the 48 events analyzed produced DHA (Table 3).

TABLE 3

DHA content of pMON96401-containing seed

| Event | Construct | Generation | DHA |
|---|---|---|---|
| AT_G3764 | pMON96401 | R2 | 0.07 |
| AT_G3756 | pMON96401 | R2 | 0.05 |
| AT_G3732 | pMON96401 | R2 | 0.04 |
| AT_G3737 | pMON96401 | R2 | 0.03 |
| AT_G3730 | pMON96401 | R2 | 0.03 |
| AT_G3740 | pMON96401 | R2 | 0.03 |
| AT_G3728 | pMON96401 | R2 | 0.02 |
| AT_G3750 | pMON96401 | R2 | 0.02 |
| AT_G3748 | pMON96401 | R2 | 0.02 |
| Control |  | VARIETY | 0 |

Molecular characterization of 4 DHA-containing events of R2 *Arabidopsis* transformed with pMON96401 seed are represented in Table 4. The data demonstrates that events that produced DHA were positive for the presence of the 5 transgenes as determined by TaqMan ® (Applied Biosystems, Foster City, Calif.) endpoint assay.

TABLE 4

*Arabidopsis* pMON96401 gene presence

| Sample | DHA | PKS5 | PKS-Ppt | PKS6 | PKS7 | PKS8 |
|---|---|---|---|---|---|---|
| Control | 0 | neg | neg | neg | neg | neg |
| At_G3748 | 0.02 | POS | POS | POS | POS | POS |
| At_G3756 | 0.04 | POS | POS | POS | POS | POS |
| At_G3764 | 0.04 | POS | POS | POS | POS | POS |
| At_G3764 | 0.07 | POS | POS | POS | POS | POS |

In the R3 generation of pMON96401 *Arabidopsis* seed, the phenotype persisted with a range of 0.025-0.1% DHA by gas chromatography. The gas chromatography peak was confirmed as DHA by gas chromatography/time of flight mass spectrometry with fish oil as a standard.

For seed-specific expression of the *Moritella marina* PKS, the native or codon-modified genes are cloned as single gene expression cassettes using seed-specific promoters such as p7Sa, p7Sa', Arcelin-5, USP88, pNapin, pFAE or pOleosin. Subsequently these expression cassettes are assembled to combine all five genes in a single binary vector using a low copy number binary vector such as pMON83934 as base vector. The resulting five-gene vectors (each of them harboring all four PKS genes plus the ppt expression cassette) may contain the expression cassettes in varying order or orientation relative to each other. These vectors are transformed into soybean and the resulting soybean seed are analyzed for fatty acid content and composition.

Figure 12:
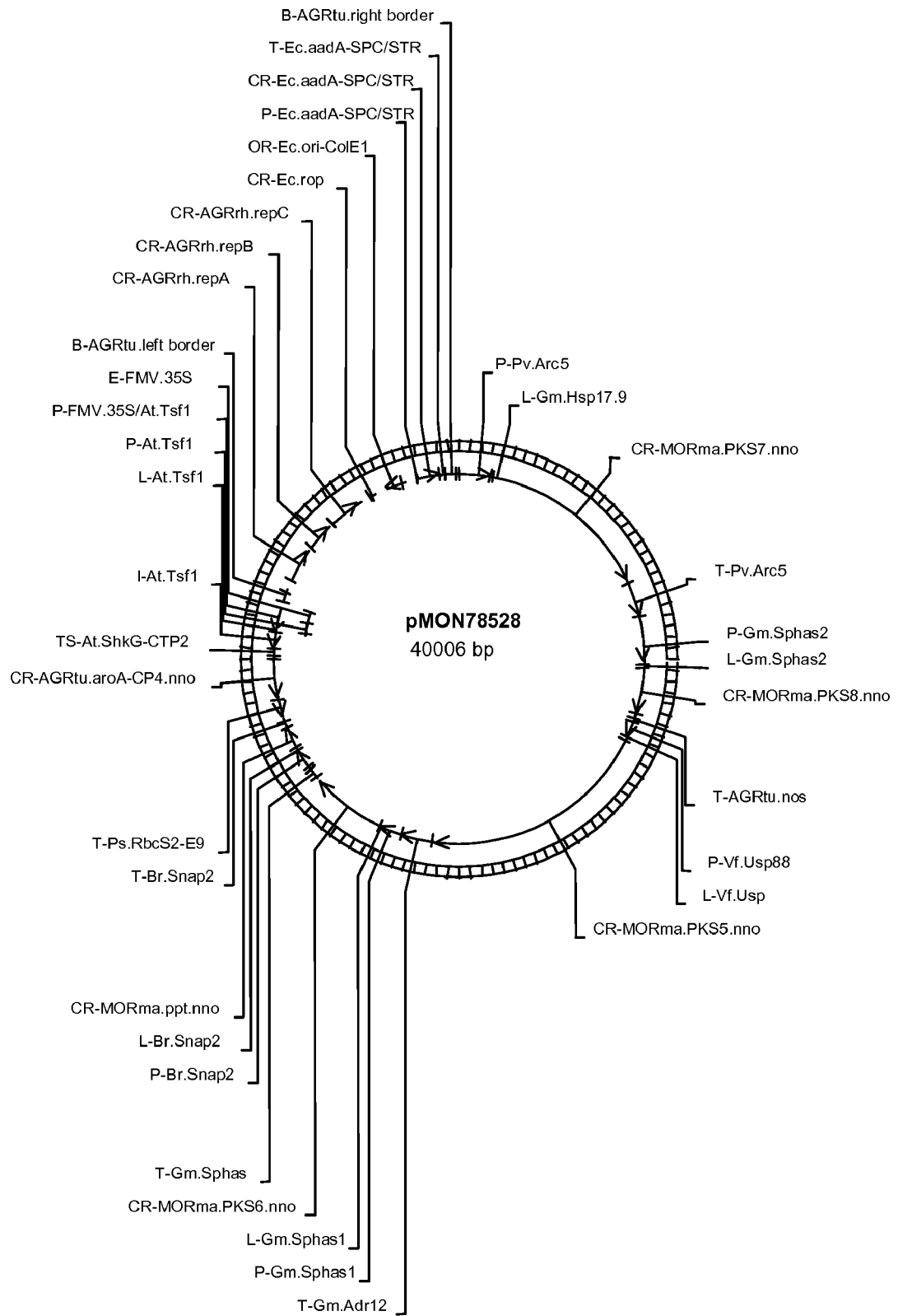
FIG. 12 shows a map of vector pMON78528.

An example of a multi-gene vector for seed-specific expression of the *M. marina* PKS and *M. marina* ppt follows. Expression cassettes for seed-specific expression of the dicot codon-enhanced PKS and ppt genes are assembled as described in Table 5. The expression cassettes are assembled in the head to tail orientation resulting in the formation of pMON78528 (FIG. 12). This binary vector is transformed into soybean and *Arabidopsis* using *Agrobacterium*-mediated transformation and the resulting seed are analyzed for fatty acid content and composition.

TABLE 5

Seed-specific expression cassettes for *M. marina* PKS.

| PROMOTER | GOI | 3' UTR |
|---|---|---|
| napin (SEQ ID NO: 35) | Mm-ppt short (SEQ ID NO: 34) | napin 3' (SEQ ID NO: 36) |
| Arcelin 5 | Orf7 (SEQ ID NO: 30) | Arcelin 5 3' |
| 7Sa' | Orf6 (SEQ ID NO: 29) | 7Sa' 3' |
| 7Sa | Orf8 (SEQ ID NO: 31) | nos 3' |
| USP88 | Orf5 (SEQ ID NO: 28) | Adr12 |

To demonstrate the ability of the *M. marina* PKS, together with the *M. marina* ppt, to synthesize DHA in corn, several plant expression cassettes are generated. The genes for orfs 5-8 and a ppt are modified for expression in monocotyledonous plants. It is known that non-endogenous protein-encoding sequences may not express well in plants (U.S. Pat. No. 5,880,275, herein incorporated by reference). Therefore, using the native Orf and Ppt polypeptide sequences previously described, artificial protein-encoding polynucleotide sequences are designed and constructed by 1) using a codon usage bias similar to that of highly expressed corn proteins, and by 2) removal of RNA destabilizing elements previously characterized and known to affect mRNA stability in planta (U.S. Pat. No. 5,880,275). The resulting modified polynucleotide sequences encode polypeptides identical in sequence to the native polypeptides. Transformed explants are obtained through *Agrobacterium tumefaciens*-mediated transformation for vectors containing the modified polynucleotide sequences. Plants are regenerated from transformed tissue. The greenhouse-grown plants are then analyzed for gene of interest expression levels as well as oil composition, including DHA or EPA.

Example 4

Cloning of Polyketide Synthase Sequences

Eight candidate polyketide synthase genes were cloned from 2 species. The deduced amino acid sequences of *M. marina* PKS genes (SEQ ID NOs: 19, 21, 23 and 25) were used to search available databases for novel polyketide synthase genes in *Shewanella oneidensis* (ATCC # 700550) and *Colwellia psychrerythraea* (ATCC # BAA-681). *S. oneidensis* accumulates EPA while *C. psychrerythraea* accumulates DHA. Based on this, it was believed that the PUFA production in these bacteria would result from a PKS mechanism. The search yielded a set of 4 candidate PKS genes from each bacterium. Using PCR cloning techniques, these genes were cloned into TOPO cloning vectors, the sequence-verified, and subcloned in Duet expression vectors (see Table 6). Expression of the *S. oneidensis* orf5 together with the *M. marina* orf6, orf7, orf8, and ppt in *E. coli* was found to result in the formation of up to 0.2% DHA as determined by gas chromatography, confirming the predicted function of the *S. oneidensis* orf5. Similarly, the function of each gene listed in Table 6 is confirmed by expression with the *M. marina* PKS genes in *E. coli* or by expression of the complete PKS gene from *Shewanella* or *Colwellia* or a combination of the two species in *E. coli*. Alternatively the function is demonstrated in plants.

TABLE 6

*E. coli* expression vectors for *Shewanella* and *Colwellia* PKS genes.

| Source organism | Gene designation | *E. coli* expression vector |
|---|---|---|
| *Shewanella oneidensis* | orf5 SEQ ID NO: 37 | pMON108255 |
| *Shewanella oneidensis* | orf6 SEQ ID NO: 38 | pMON108256 |
| *Shewanella oneidensis* | orf7 SEQ ID NO: 39 | pMON108258 |
| *Shewanella oneidensis* | orf8 SEQ ID NO: 40 | pMON108259 |
| *Moritella marina* | orf6 SEQ ID NO: 22 | pMON108252 |
| *Shewanella oneidensis* | orf5 SEQ ID NO: 37 | |
| *Colwellia psychrerythraea* | orf5 SEQ ID NO: 41 | pMON108267 |
| *Colwellia psychrerythraea* | orf7 SEQ ID NO: 43 | pMON108269 |
| *Colwellia psychrerythraea* | orf8 SEQ ID NO: 44 | pMON108270 |
| *Colwellia psychrerythraea* | orf5 SEQ ID NO: 41 orf6 SEQ ID NO: 42 | pMON108268 |

REFERENCES

The references listed below are incorporated herein by reference to the extent that they supplement, explain, provide a background for, or teach methodology, techniques, and/or compositions employed herein.

U.S. Pat. Nos. 4,518,584, 4,737,462, 4,810,648, 4,957,748, 4,965,188, 5,094,945, 5,100,679, 5,176,995, 5,196,525, 5,219,596, 5,290,924, 5,322,783, 5,359,142, 5,424,398, 5,424,412, 5,500,365, 5,538,880, 5,550,318, 5,563,055, 5,610,042, 5,627,061, 5,633,435, 5,641,876, 5,880,275, 5,936,069, 6,005,076, 6,040,497, 6,140,486, 6,140,486, 6,140,486, 6,140,486, 6,146,669, 6,156,227, 6,265,638, 6,319,698, 6,433,252, 6,451,567, U.S. application Ser. Nos. 10/235,618, 10/429,516, U.S. Publn. 20040039058, U.S. Publn. 20040235127

Allen and Bartlett, *Microbiology*, 148(Pt 6):1903-1913, 2002.
Baerson et al., *Plant Mol Biol.*, 22(2):255-267, 1993.
Barany et al., *Int. J. Peptide Protein Res.*, 30:705-739, 1987.
Bauer et al., *Gene*, 37:73, 1985.
Belanger and Kriz, *Genet.*, 129:863-872, 1991.
Bevan et al., *Nucleic Acids Res.*, 11(2):369-385, 1983.
Bodanszky, In: *Principles of Peptide Synthesis*, Springer-Verlag, Heidelberg, 1984.
Bustos, et al., *Plant Cell*, 1(9):839-853, 1989.
Callis et al., *Genes Dev.*, 1:1183-1200, 1987.
Chandler et al., *Plant Cell*, 1: 1175-1183, 1989.
Chen et al., *Proc. Natl. Acad. Sci. USA*, 83:8560-8564, 1986.
Chu et al., *Scientia Sinica*, 18:659-668, 1975.
De Deckerer, *Eur. J. Clin. Nutr.*, 52:749, 1998.
DeBlock et al., *EMBO J.*, 6:2513-2519, 1987.
Ebert et al., *Proc. Natl. Acad. Sci. USA*, 84:5745-5749, 1987.
Freitag and Selker, *Curr. Opin. Genet. Dev.*, 15(2):191-199, 2005.
Gallie et al., *The Plant Cell*, 1:301, 1999.
Hong et al., *Plant Mol. Biol.*, 34(3):549-555, 1997.
Hudspeth and Grula, *Plant Mol Biol*, 12:579-589, 1989.
Ingelbrecht et al., *Plant Cell*, 1:671-680, 1989.
James et al., *Semin. Arthritis Rheum.*, 28:85, 2000.
Joshi et al., *Plant Mol Biol*, 35(6):993-1001 1997.
Joshi, *Nucleic Acids Res.*, 15:6643-6653, 1987.
Kridl et al., *Seed Sci. Res.*, 1:209:219, 1991.
Kridl et al., *Seed Sci. Res.*, 1:209-219, 1991.
Lawton et al., *Plant Mol. Biol* 9:315-324, 1987.
Lopes et al., *Mol. Gen. Genet.*, 247:603-613, 1995.
Maniatis, et al., Molecular Cloning, A Laboratory Manual, Cold Spring Harbor Press, Cold Spring Harbor, N.Y., 1989.
Manzioris et al., *Am. J. Clin. Nutr.*, 59:1304, 1994.

Maundrell, *J. Biol. Chem.*, 265(19):10857-10864, 1990.
McElroy et al., *Mol. Gen. Genet.*, 231(1):150-160, 1991.
Merrifield, *J. Am. Chem. Soc.*, 85:2149-2154, 1963.
Metz et al., *Science*, 293(5528):290-293, 2001.
Misawa et al., *Plant J.*, 4:833-840, 1993.
Misawa et al., *Plant J.*, 6:481-489, 1994.
Murashige and Skoog, *Physiol Plant*, 15:473-497, 1962.
Naylor et al., *Nature*, 405:1017, 2000.
PCT Appln. WO 04071467A2
PCT Appln. WO 05103253A1
PCT Appln. WO 2002/50295
PCT Appln. WO 95/06128
PCT Appln. WO 96/33155
Pedersen et al., *Cell*, 29:1015-1026, 1982.
Recombinant DNA Part D, Methods in Enzymology, Vol. 153, Wu and Grossman, eds., Academic Press, 1987.
Richins et al., *Nucleic Acids Res.*, 20:8451, 1987.
Riggs, et al., *Plant Cell*, 1(6):609-621, 1989.
Russell et al., *Transgenic Res.*, 6(2):157-168, 1997.
Sambrook et al., *In: Molecular cloning: a laboratory manual*, 2$^{nd}$ Ed., Cold Spring Harbor Laboratory Press, Cold Spring Harbor, N.Y., 1989.
Sathasiivan et al., *Nucl. Acids Res.*, 18:2188-2193, 1990.
Simopoulos et al., *Am. Coll. Nutr.*, 18:487, 1999.
Simopoulos, *Can. J. Physiol Pharmacol* 75:234-239, 1997
Slocombe et al., *Plant Physiol*, 104(4): 167-176, 1994.
Stacey et al., *Plant Mol Biol*, 31:1205-1216, 1996.
Sullivan et al., *Mol Gen. Genet.*, 215(3):431-440, 1989.
Turner and Foster, *Molecular Biotech.*, 3:225, 1995.
Vasil et al., *Plant Physiol.*, 91:1575-1579, 1989.
Walder et al., *Gene*, 42:133, 1986.
Walker et al., *Proc. Natl. Acad. Sci. USA*, 84:6624, 1987.
Wang et al., *Molec. Cell Biol.*, 12(8):3399-3406, 1992.
Wohlleben et al., *Gene*, 70:25-37, 1988.
Yang et al., *Proc. Natl. Acad. Sci. USA*, 87:9568-9572, 1990.

---

What is claimed is:

1. An isolated polynucleotide comprising a sequence selected from the group consisting of:
    (a) a polynucleotide hybridizing to SEQ ID NO:6 or SEQ ID NO:8, or a complement thereof, under conditions of 5×SSC, 50% formamide and 42° C., wherein the polynucleotide encodes polypeptide with phosphopantetheinyl transferase activity;
    (b) a polynucleotide encoding the polypeptide sequence of SEQ ID NO:5 or SEQ ID NO:7; and
    (c) a polynucleotide encoding a polypeptide with phosphopantetheinyl transferase activity and having at least 90% sequence identity to a polypeptide sequence of SEQ ID NO:5 or SEQ ID NO:7.

2. The isolated polynucleotide of claim 1, further defined as operably linked to a heterologous promoter.

3. A DNA construct comprising a heterologous promoter operably linked to a polynucleotide comprising a sequence selected from the group consisting of:
    (a) a polynucleotide hybridizing to SEQ ID NO:6 or SEQ ID NO:8, or a complement thereof, under conditions of 5×SSC, 50% formamide and 42° C., wherein the polynucleotide encodes polypeptide with phosphopantetheinyl transferase activity;
    (b) a polynucleotide encoding the polypeptide sequence of SEQ ID NO:5 or SEQ ID NO:7; and
    (c) a polynucleotide encoding a polypeptide with phosphopantetheinyl transferase activity and having at least 90% sequence identity to a polypeptide sequence of SEQ ID NO:5 or SEQ ID NO:7.

4. The DNA construct of claim 3, wherein the promoter is functional in a prokaryotic cell.

5. The DNA construct of claim 3, wherein the promoter is functional in a eukaryotic cell.

6. The DNA construct of claim 5, wherein the promoter is functional in a plant cell.

7. The DNA construct of claim 6, wherein the promoter is a seed-enhanced promoter.

8. A host cell transformed with the construct of claim 3.

9. The host cell of claim 8, wherein the host cell further comprises a DNA molecule encoding a polyketide synthase polypeptide comprising a phosphopantetheine attachment site, wherein the DNA molecule encoding a polyketide synthase polypeptide is operably linked to a heterologous promoter.

10. The host cell of claim 9, wherein the polyketide synthase polypeptide comprises a phosphopantetheine attachment site from *Moritella marina*.

11. The host cell of claim 9, wherein the host cell further comprises a DNA molecule encoding a polyketide synthase polypeptide having at least 75% sequence identity to the polypeptide sequence of SEQ ID NO:19.

12. The host cell of claim 8, wherein the host cell is a plant cell.

13. The host cell of claim 8, wherein the host cell is a fungal or bacterial cell.

14. The host cell of claim 8, defined as exhibiting altered fatty acid biosynthesis relative to a cell of the same genotype as said host cell but lacking the DNA molecule.

15. A transgenic plant transformed with the construct of claim 3.

16. The plant of claim 15 wherein the plant is selected from the group consisting of canola, *Brassica campestris*, oilseed rape, rapeseed, soybean, crambe, mustard, castor bean, peanut, sesame, cottonseed, linseed, safflower, oil palm, flax, sunflower, corn, rice, barley, millet, rye, wheat, oat, alfalfa and sorghum.

17. The plant of claim 15, further defined as comprising a DNA molecule encoding polyketide synthase.

18. A seed of the transgenic plant of claim 15, wherein the seed comprises the comprising a DNA molecule.

19. A method of producing food or feed, comprising the steps of:
    (a) obtaining the transgenic plant of claim 15 or a part thereof; and
    (b) producing said food or feed therefrom.

20. The method of claim 19, wherein the food or feed is oil, silage, meal, grain, starch, flour, or protein.

21. A food or feed composition produced by the method of claim 19 and comprising a detectable nucleic acid molecule comprising the isolated polynucleotide of claim 1.

22. A food or feed composition produced by the method of claim 19, wherein the food or feed composition comprises said contruct.

23. The food or feed composition of claim 21, wherein the plant is of a species that does not produce docosahexaenoic acid or eicosapentaenoic acid when the plant lacks said DNA molecule encoding polyketide synthase and DNA molecule encoding a polypeptide having phosphopantetheinyl transferase activity.

24. A method of producing docosahexaenoic acid or eicosapentaenoic acid comprising the steps of:
    (a) expressing in the seeds of a plant the construct of claim 3 to produce docosahexaenoic acid or eicosapentaenoic acid; and
    (b) obtaining the docosahexaenoic acid or eicosapentaenoic acid from said seed.

25. A food or feed composition produced from a plant prepared according to claim 24, comprising docosahexaenoic acid or eicosapentaenoic acid.

\* \* \* \* \*

UNITED STATES PATENT AND TRADEMARK OFFICE
CERTIFICATE OF CORRECTION

PATENT NO. : 7,868,228 B2  Page 1 of 1
APPLICATION NO. : 11/668354
DATED : January 11, 2011
INVENTOR(S) : Valentin et al.

It is certified that error appears in the above-identified patent and that said Letters Patent is hereby corrected as shown below:

On the cover page, item (66), delete "substitute for application" and insert
--Provisional application--.

Signed and Sealed this
Fourth Day of September, 2012

David J. Kappos
*Director of the United States Patent and Trademark Office*

SEQUENCE LISTING

<160> NUMBER OF SEQ ID NOS: 44

<210> SEQ ID NO 1
<211> LENGTH: 318
<212> TYPE: PRT
<213> ORGANISM: Shewanella oneidensis

<400> SEQUENCE: 1

```
Met Lys Ile Glu Leu Phe Phe Ile Pro Leu Ala Glu Met Asp Ala Glu
1               5                   10                  15

Met Val Ser Arg Cys Met Ala Leu Leu Ser Glu Asp Glu Arg Ala Lys
            20                  25                  30

Val Ala Arg Tyr Leu Ala Pro Lys Ala Gln Met Asn Gly Leu Leu Val
        35                  40                  45

Arg Ala Ala Leu Arg Cys Val Leu Ser Gln Gly Leu Gln Ser Pro Asn
    50                  55                  60

Glu Ser Ser Leu Asn Ala Phe Ser Ser Asn Thr Gly Ser Leu Pro Ile
65                  70                  75                  80

Ala Pro Gln Asp Trp Cys Phe Glu Tyr Gly Ala Lys Gly Lys Pro Ser
                85                  90                  95

Leu Cys His Glu Gln Phe Leu Lys Thr Gly Ile Glu Phe Asn Leu Ser
            100                 105                 110

His Ser Gly Asp Trp Leu Leu Ile Ala Leu Ala Gln Gly Arg Ala His
        115                 120                 125

Thr Lys Phe Ile Asp Gln Ser Ala Lys Thr Arg Leu Gly Leu Gly Val
    130                 135                 140

Asp Ile Glu Arg Ala Arg Ala Ser Thr Asn Ile Tyr Pro Ile Leu Asn
145                 150                 155                 160

His Tyr Phe Ser Ala Arg Glu Thr Glu Ala Leu Leu Ala Leu Pro Gly
                165                 170                 175

Glu Thr Ala His Arg Gln Arg Phe Phe Asp Leu Trp Ala Leu Lys Glu
            180                 185                 190

Ser Tyr Ile Lys Ala Thr Gly Leu Gly Leu Ala Gln Ser Leu Lys Ser
        195                 200                 205

Phe Ala Phe Glu Leu Met Pro Asp Ala Leu Val Glu Val His Pro Asn
    210                 215                 220

Gln Val Ala Leu Arg His Glu Trp Val Glu Leu Lys Arg Arg Glu Pro
```

```
                225                 230                 235                 240
Phe Ala Leu Pro Ser Gln Leu Lys Leu Tyr Cys Glu Ile Lys Pro Thr
            245                 250                 255
Ala Ala Phe Leu Pro Asp Ser Ala His Pro Pro Glu Asn Leu His
        260                 265                 270
Val Gln Ser Tyr Phe Gly Arg Leu Asp Glu Glu Tyr Arg Phe Gly Leu
            275                 280                 285
Ser Leu Ile His Pro Asn Ala Leu Ser Asn Val Gln Ile Ser Met Thr
        290                 295                 300
Leu Ala Ser Ile Lys Ser Leu Leu Ala Ala Ser Leu Ala Asp
305                 310                 315
```

<210> SEQ ID NO 2
<211> LENGTH: 957
<212> TYPE: DNA
<213> ORGANISM: Shewanella oneidensis

<400> SEQUENCE: 2

```
atgaagattg agcttttttt tataccatta gccgagatgg atgctgaaat ggtgagccgt      60
tgtatggcgc tgttgagtga ggacgagcgt gcaaaagtgg cgcgttacct tgcgcccaag     120
gcgcaaatga atggcttatt ggtgcgagcg cgctgcgct gtgtcttatc tcaagggctg     180
caatctccaa atgaatcttc acttaacgca ttttcatcta acacaggctc actacccatt     240
gctccccaag attggtgttt tgagtatggg gcaaagggca acccagtct ctgccatgag     300
cagtttctga agacgggtat tgagtttaac ttaagccaca gtggcgactg gttattgata     360
gccttggcgc aagggcgggc tcatacaaaa ttcatcgatc aaagtgcaaa aactcgctta     420
ggtttaggtg tcgatattga gcgggcccgg gcaagcacaa atatttaccc cattctgaat     480
cattattttt ctgcgcgaga aaccgaggcg ctactggcat tgccgggcga aaccgcccac     540
cgccaacgat tttttgacct gtgggcgctt aaagagtcct acatcaaggc aacaggttta     600
ggcttagcgc agtcgttaaa atcctttgcc tttgagttga tgcctgatgc acttgtcgag     660
gtccatccca atcaagtagc gcttcgccat gaatgggttg aacttaaaag gcagaaccc      720
tttgcgttac caagccagct taaattgtat tgcgagatta gcctacggc ggcgtttctg      780
cccgattctg cgcatccgcc gccagaaaac ttgcacgtgc aaagctactt tggtcggctt     840
gatgaggaat atcgctttgg cttgagtctc attcatccta acgcgctatc gaatgtgcag     900
atttcgatga cgcttgccag catcaaatcg ttgttagcgg ctagtttggc tgactaa        957
```

<210> SEQ ID NO 3
<211> LENGTH: 282
<212> TYPE: PRT
<213> ORGANISM: Colwellia psychrerythraea

<400> SEQUENCE: 3

```
Met Thr Ser Phe Ser Gln Ser Glu Leu Ser Thr Arg Thr Lys Glu Lys
1               5                   10                  15
Leu Asp Leu Ala Ala Asn Glu Ile His Ile Trp Val Thr Lys Pro Glu
            20                  25                  30
Glu Leu Leu Gly Asn Asp Glu Leu Leu Ala Thr Tyr Ser Thr Leu Leu
        35                  40                  45
Thr Ser Thr Glu Thr Ala Lys Gln Gln Arg Tyr Lys Phe Ala Lys Asp
    50                  55                  60
Arg His Asp Ala Leu Ile Thr Arg Ala Phe Ile Arg Asp Leu Leu Ser
65                  70                  75                  80
```

Tyr Tyr Ala Asp Val Ala Pro Gln Asp Trp Gln Phe Glu Lys Gly Asn
            85                  90                  95

Lys Asp Lys Pro Glu Val Ile Asn Cys Pro Leu Pro Leu Arg Phe Asn
        100                 105                 110

Ile Ser His Thr Lys Asn Leu Ile Ile Cys Ala Val Thr Leu Glu Asp
        115                 120                 125

Asp Ile Gly Cys Asp Val Glu Asn Thr Gly Arg Asn Asn Asn Val Leu
        130                 135                 140

Ala Ile Ala Glu Arg Tyr Phe Ser Ser Lys Glu Ile Asp Glu Leu Phe
145                 150                 155                 160

Ala Leu Pro Glu Ala Gln Gln Arg Asn Arg Phe Phe Asp Tyr Trp Thr
                165                 170                 175

Leu Lys Glu Ser Tyr Ile Lys Ala Trp Gly Leu Gly Leu Ala Ile Pro
            180                 185                 190

Leu Ala Asp Phe Ser Phe Lys Ile Asn Asp Thr Glu His Asn His Asn
            195                 200                 205

Gly Leu Phe Thr Ile Lys Gln Asp Ile Asn Leu Ser Phe Ala Glu His
        210                 215                 220

Arg Val Asp Glu Pro Gln Ile Trp Arg Ser Trp Leu Val Tyr Pro Thr
225                 230                 235                 240

Ala Ala Ile Asp Glu Lys Gln Glu His Arg Ile Ala Val Ser Leu Arg
                245                 250                 255

Ala Thr Ser Asp Asn Gln Lys Thr Asp Tyr Gln Leu Arg Phe Phe Asn
            260                 265                 270

Thr Leu Pro Leu Leu Gly Tyr Gln Glu Ile
        275                 280

<210> SEQ ID NO 4
<211> LENGTH: 849
<212> TYPE: DNA
<213> ORGANISM: Colwellia psychrerythraea

<400> SEQUENCE: 4
atgacttctt tttctcaatc tgaactctcc actcgaacaa agaaaaagct cgaccttgct      60
gccaatgaaa ttcatatatg ggtaaccaaa ccggaagagt tactcggcaa tgatgagtta     120
ttagcaacct actcaacatt attaacgagt acagaaacag ccaaacagca acgatataag     180
tttgctaaag atagacacga tgccttgatt actcgcgctt tcatacgcga tttattatct     240
tattatgctg atgtagcacc gcaagattgg cagtttgaaa aggtaataa agataaacct     300 gaagttatta attgcccact gccgctgcgc tttaacatca gccatacaaa aaatcttata     360
atttgcgcgg taacgcttga ggatgatatc ggttgtgatg ttgaaaatac cggccgcaac     420
aataatgtat tagcgattgc tgaacgttat ttttcttcta agaaatagaa tgaactttt     480 gcgctgccag aagcacaaca acgcaatcgg ttttttgatt attggacatt aaaagagtct     540
tatattaaag cttggggttt aggtttagcg ataccactcg ctgattttag ttttaaaatt     600
aacgataccg aacataatca taacggttta tttactatca agcaggacat taacctaagc     660
tttgctgagc atagagtaga tgaaccacaa atttggcgta gctggttagt ttacccaacg     720
gctgccatag atgaaaaaca agaacaccgc atcgctgtat cgttaagagc aaccagcgac     780
aatcaaaaaa ctgactacca attacgtttc tttaataccc tgcccctact ggttatcag     840 gaaatctaa                                                             849

<210> SEQ ID NO 5
<211> LENGTH: 329
<212> TYPE: PRT
<213> ORGANISM: Moritella marina

<400> SEQUENCE: 5

```
Leu Val Gln Leu Lys Thr Tyr Asp Glu Thr Arg Leu Arg Ser Asp Gly
1               5                   10                  15

Val Asn Tyr Leu Gly Gly Asn Leu Ser Tyr Tyr Gln Ala Cys Asn Gly
            20                  25                  30

Lys Arg Ile Ile Leu Val Ser Ile Leu Ile Met Tyr Ser Gly Val Lys
        35                  40                  45

Asp Lys Leu Thr Leu Thr Thr Asn Glu Ile His Leu Trp Ser Val Thr
    50                  55                  60

Pro Gln Thr Ile Gln Gln Pro Glu Leu Leu Ala Tyr Ser Gln Leu
65                  70                  75                  80

Leu Ser Pro Ala Glu Thr Ile Lys Gln Gln Arg Phe Arg Phe Glu Lys
                85                  90                  95

Asp Arg His Asn Ala Leu Ile Thr Arg Ala Phe Val Arg Asp Leu Leu
            100                 105                 110

Ser His Tyr Ala Asp Val Leu Pro Ala Asp Trp Gln Phe Val Lys Gly
        115                 120                 125

Glu Lys Asp Lys Pro Glu Ile Ala Asn Pro Pro Leu Pro Leu Arg Phe
    130                 135                 140

Asn Ile Ser His Thr Asp Asn Leu Ile Ile Cys Ala Val Met Leu Asn
145                 150                 155                 160

Asp Asp Ile Gly Cys Asp Val Glu Asn Thr Leu Arg Ser Ser Asn Val
                165                 170                 175

Leu Ser Ile Ala Lys His Ser Phe Ser Asp Ser Glu Phe Asn Asp Leu
            180                 185                 190

Leu Thr Gln Pro Thr Ala Gln Gln Thr Ser Arg Phe Phe Asp Tyr Trp
        195                 200                 205

Thr Leu Lys Glu Ser Tyr Ile Lys Ala Trp Gly Leu Gly Leu Ser Ile
    210                 215                 220

Pro Leu Lys Asp Phe Ser Phe Thr Leu Pro Glu Gly Phe Gln Gln Gln
225                 230                 235                 240

Tyr Gln Gln Glu Asp Gln Gln Glu Asn Gln His Cys Ile Asp Thr Ile
                245                 250                 255

Lys Leu Ser Phe Ala Pro His Arg Ile Asp Asn Pro Asn Ile Trp Arg
            260                 265                 270

His Trp Leu Phe Tyr Pro Asn Asn Thr His Arg Val Ala Leu Ala Val
        275                 280                 285

Arg Ala Arg Ser Asn Asn Gln Gln Thr Glu Tyr Lys Met Arg Phe Phe
    290                 295                 300

Asn Ser Thr Pro Leu Ile Asn Ile Thr Glu Thr Leu Ile Phe Lys Pro
305                 310                 315                 320

Glu Thr Asn Phe Lys Pro Asp Ala Lys
                325
```

<210> SEQ ID NO 6
<211> LENGTH: 990
<212> TYPE: DNA
<213> ORGANISM: Moritella marina

<400> SEQUENCE: 6
ttggtacagc ttaaaaccta tgacgaaaca agattacgca gtgatggggt taattacctt    60

```
ggtggtaacc ttagctatta tcaagcgtgt aatggcaagc gaattattct ggtatccatt      120
ctaattatgt acagcggcgt aaaagataag ctcaccctca ctacaaatga aatccattta      180
tggtcggtta ctccgcaaac tatccaacag cctgaattat tacaggctta tagccaactg      240
ttatcacctg cagaaacaat aaaacaacaa cgctttcgat ttgaaaaga tcgtcacaat       300 gctctcatca ctcgtgcttt cgtccgtgat ttattatctc actatgcaga tgttttaccg      360
gctgattggc agtttgtgaa ggggaaaag gataaaccag agatagcgaa tcccccactc       420
ccactgcgct ttaatattag tcataccgat aacttaatca tttgtgccgt catgctcaat      480
gatgatatcg gttgtgatgt cgaaaataca ctgcgtagca gtaatgtctt gagtattgct      540
aaacattcat tctcagatag tgaattcaat gatttacttc ctcaacccac tgcacaacaa      600
accagtcgtt ttttttgatta ctggacgtta aaagaatctt atatcaaagc atggggcttg     660
ggtttatcga tcccgttgaa agatttcagc ttcacgctac ccgaaggctt caacagcag      720 tatcaacaag aagatcagca agaaaaccag cattgtattg ataccattaa attaagcttt      780
gcacctcacc gtattgataa tcccaacatt tggcgtcatt ggctgttcta tccaaataat      840
acccacagag ttgcactggc tgtgcgcgcg cgaagtaata atcagcagac tgaatataaa      900
atgcgatttt ttaattcgac accactgatt aatatcactg aaacacttat ttttaaacct      960
gagactaatt ttaaacctga cgctaaatag                                      990
```

```
<210> SEQ ID NO 7
<211> LENGTH: 287
<212> TYPE: PRT
<213> ORGANISM: Moritella marina

<400> SEQUENCE: 7

Met Tyr Ser Gly Val Lys Asp Lys Leu Thr Leu Thr Thr Asn Glu Ile
1               5                   10                  15

His Leu Trp Ser Val Thr Pro Gln Thr Ile Gln Gln Pro Glu Leu Leu
            20                  25                  30

Gln Ala Tyr Ser Gln Leu Leu Ser Pro Ala Glu Thr Ile Lys Gln Gln
        35                  40                  45

Arg Phe Arg Phe Glu Lys Asp Arg His Asn Ala Leu Ile Thr Arg Ala
    50                  55                  60

Phe Val Arg Asp Leu Leu Ser His Tyr Ala Asp Val Leu Pro Ala Asp
65                  70                  75                  80

Trp Gln Phe Val Lys Gly Glu Lys Asp Lys Pro Glu Ile Ala Asn Pro
                85                  90                  95

Pro Leu Pro Leu Arg Phe Asn Ile Ser His Thr Asp Asn Leu Ile Ile
            100                 105                 110

Cys Ala Val Met Leu Asn Asp Asp Ile Gly Cys Asp Val Glu Asn Thr
        115                 120                 125

Leu Arg Ser Ser Asn Val Leu Ser Ile Ala Lys His Ser Phe Ser Asp
    130                 135                 140

Ser Glu Phe Asn Asp Leu Leu Thr Gln Pro Thr Ala Gln Gln Thr Ser
145                 150                 155                 160

Arg Phe Phe Asp Tyr Trp Thr Leu Lys Glu Ser Tyr Ile Lys Ala Trp
                165                 170                 175

Gly Leu Gly Leu Ser Ile Pro Leu Lys Asp Phe Ser Phe Thr Leu Pro
            180                 185                 190

Glu Gly Phe Gln Gln Gln Tyr Gln Gln Glu Asp Gln Gln Glu Asn Gln
        195                 200                 205
```

```
His Cys Ile Asp Thr Ile Lys Leu Ser Phe Ala Pro His Arg Ile Asp
    210                 215                 220

Asn Pro Asn Ile Trp Arg His Trp Leu Phe Tyr Pro Asn Asn Thr His
225                 230                 235                 240

Arg Val Ala Leu Ala Val Arg Ala Arg Ser Asn Asn Gln Gln Thr Glu
                245                 250                 255

Tyr Lys Met Arg Phe Phe Asn Ser Thr Pro Leu Ile Asn Ile Thr Glu
            260                 265                 270

Thr Leu Ile Phe Lys Pro Glu Thr Asn Phe Lys Pro Asp Ala Lys
        275                 280                 285

<210> SEQ ID NO 8
<211> LENGTH: 864
<212> TYPE: DNA
<213> ORGANISM: Moritella marina

<400> SEQUENCE: 8
atgtacagcg gcgtaaaaga taagctcacc ctcactacaa atgaaatcca tttatggtcg      60
gttactccgc aaactatcca acagcctgaa ttattacagg cttatagcca actgttatca     120
cctgcagaaa caataaaaca caacgctttc gatttgaaaa agatcgtca caatgctctc      180 atcactcgtg ctttcgtccg tgatttatta tctcactatg cagatgtttt accggctgat     240
tggcagtttg tgaaggggga aaaggataaa ccagagatag cgaatccccc actcccactg     300
cgctttaata ttagtcatac cgataactta atcatttgtg ccgtcatgct caatgatgat     360
atcggttgtg atgtcgaaaa tacactgcgt agcagtaatg tcttgagtat tgctaaacat     420
tcattctcag atagtgaatt caatgattta cttactcaac ccactgcaca acaaaccagt     480 cgttttttg attactggac gttaaaagaa tcttatatca aagcatgggg cttgggttta      540
tcgatcccgt tgaaagattt cagcttcacg ctacccgaag ctttcaaca gcagtatcaa      600 caagaagatc agcaagaaaa ccagcattgt attgatacca ttaaattaag ctttgcacct     660
caccgtattg ataatcccaa catttggcgt cattggctgt tctatccaaa taatacccac     720
agagttgcac tggctgtgcg cgcgcgaagt aataatcagc agactgaata taaaatgcga     780
ttttttaatt cgacaccact gattaatatc actgaaacac ttattttaa acctgagact      840 aattttaaac ctgacgctaa atag                                           864

<210> SEQ ID NO 9
<211> LENGTH: 38
<212> TYPE: DNA
<213> ORGANISM: Artificial
<220> FEATURE:
<223> OTHER INFORMATION: Primer

<400> SEQUENCE: 9
tcgagctcgc atatgaagat tgagcttttt tttatacc                              38

<210> SEQ ID NO 10
<211> LENGTH: 31
<212> TYPE: DNA
<213> ORGANISM: Artificial
<220> FEATURE:
<223> OTHER INFORMATION: Primer

<400> SEQUENCE: 10
tcttaattaa ttagtcagcc aaactagccg c                                     31
```

```
<210> SEQ ID NO 11
<211> LENGTH: 34
<212> TYPE: DNA
<213> ORGANISM: Artificial
<220> FEATURE:
<223> OTHER INFORMATION: Primer

<400> SEQUENCE: 11
tcgagctcgc atatgacttc tttttctcaa tctg                              34

<210> SEQ ID NO 12
<211> LENGTH: 34
<212> TYPE: DNA
<213> ORGANISM: Artificial
<220> FEATURE:
<223> OTHER INFORMATION: Primer

<400> SEQUENCE: 12
tcttaattaa ttagatttcc tgataaccaa gtag                              34

<210> SEQ ID NO 13
<211> LENGTH: 21
<212> TYPE: DNA
<213> ORGANISM: Artificial
<220> FEATURE:
<223> OTHER INFORMATION: Primer

<400> SEQUENCE: 13
taggtgtcga tattgagcgg g                                            21

<210> SEQ ID NO 14
<211> LENGTH: 21
<212> TYPE: DNA
<213> ORGANISM: Artificial
<220> FEATURE:
<223> OTHER INFORMATION: Primer

<400> SEQUENCE: 14
tcaaaggcaa aggattttaa c                                            21

<210> SEQ ID NO 15
<211> LENGTH: 22
<212> TYPE: DNA
<213> ORGANISM: Artificial
<220> FEATURE:
<223> OTHER INFORMATION: Primer

<400> SEQUENCE: 15
tcggttgtga tgttgaaaat ac                                           22

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
ttaaaactaa aatcagcgag t                                            21

<210> SEQ ID NO 17
<211> LENGTH: 329
<212> TYPE: PRT
<213> ORGANISM: Shewanella sp. SCRC-2738

<400> SEQUENCE: 17
```

```
Met Leu Thr Ser Arg Leu Ile Ser Leu Tyr Phe Cys Pro Leu Thr Ile
1               5                   10                  15

Gln Glu Cys Asp Asn Gln Thr Thr Glu Leu Val Lys Ser Trp Leu Pro
            20                  25                  30

Glu Asp Glu Leu Ile Lys Val Asn Arg Tyr Ile Lys Gln Glu Ala Lys
        35                  40                  45

Thr Gln Gly Leu Met Val Arg Gly Tyr Leu Arg Ala Leu Leu Ser Gln
    50                  55                  60

His Ser Glu Ile Arg Pro Asn Glu Trp Arg Phe Glu Tyr Gly Asp Lys
65                  70                  75                  80

Gly Lys Pro Arg Leu Ser Asp Ala Gln Phe Ala Gln Thr Gly Val His
                85                  90                  95

Phe Asn Val Ser His Ser Gly Asp Trp Leu Leu Val Gly Ile Cys Thr
            100                 105                 110

Ala Asp Asn Lys Gly Ala Ser Gln Ala Ser Lys Glu Glu Thr Asp Ser
        115                 120                 125

Ala Ser Ile Glu Phe Gly Val Asp Ile Glu Arg Cys Arg Asn Ser Thr
    130                 135                 140

Asn Ile His Ser Ile Leu Ser His Tyr Phe Ser Glu Ser Glu Lys Arg
145                 150                 155                 160

Ala Leu Leu Ala Leu Pro Glu Ala Leu Gln Arg Asp Arg Phe Phe Asp
                165                 170                 175

Leu Trp Ala Leu Lys Glu Ser Tyr Ile Lys Ala Lys Gly Leu Gly Leu
            180                 185                 190

Ala Leu Ser Leu Lys Ser Phe Ala Phe Asp Phe Ser Ala Leu Ser Glu
        195                 200                 205

Thr Phe Leu Gly Val Asn Ala Pro Lys Ser Leu Ser His Cys Val Asp
    210                 215                 220

Ile Ser Asp Ala Ile Ala Asp His Lys Val Glu His Gln Leu Asn Gln
225                 230                 235                 240

Arg Gln Val Leu Leu Lys Gln Asp Ile Gly Leu Ala Leu Leu Glu Ser
                245                 250                 255

Ser Ser Asn Lys Pro Asn Ala Glu Pro Gln Lys Ser Gly Leu Gly Leu
            260                 265                 270

Ile Glu Ala Lys Glu Gln Gln Met Asn Ala Ala Asp Asn Trp His Cys
        275                 280                 285

Leu Leu Gly His Leu Asp Asp Ser Tyr Arg Phe Ala Leu Ser Ile Gly
    290                 295                 300

Gln Cys Gln Gln Ile Ser Ile Ala Ala Glu Glu Val Asn Phe Lys Ala
305                 310                 315                 320

Val Val Arg Ala Ser Ala Lys Thr Ser
                325
```

<210> SEQ ID NO 18
<211> LENGTH: 990
<212> TYPE: DNA
<213> ORGANISM: Shewanella sp. SCRC-2738

<400> SEQUENCE: 18

```
ttgctaactt ctcgattgat ttccttatac ttctgtccgt taacaataca agagtgcgat    60
aaccagacta cagagttggt taagtcatgg ctgcctgaag atgagttaat taaggttaat   120
cgctacatta acaagaagc  taaaactcaa ggtttaatgg taagaggcta tttgcgcgct   180
ttattgtcac aacatagtga aatacgcccc aatgaatggc gctttgaata tggcgacaaa   240
```

```
ggtaagccta gattgagtga tgcgcaattt gctcaaaccg gggtccactt taatgtgagt    300
catagtggag attggctatt agtaggcatt tgcactgctg ataataaagg cgccagtcag    360
gcaagcaagg aggaaactga ctctgctagt attgagtttg cgtcgacat tgagcgttgc    420 cgtaacagca ccaatatcca ctctattctt agtcattatt tctctgaatc agaaaagcga    480
gccttgttag cgttaccaga ggccttgcag cgagaccgct ttttgattt gtgggcgctc    540 aaggagtctt acattaaagc gaaaggactt gggctggcat tatcgctaaa atcttttgcg    600
tttgacttct ctgcactgag cgaaactttt cttggagtta atgcacctaa agcttgagc    660 cattgtgtta tatttccga tgctattgcg gatcacaagg ttgagcatca acttaatcag    720
cgacaggttt tgttaaaaca agatattggt cttgctttac tagagtcgag ttctaataag    780
cctaacgctg agccacaaaa gtctggttta ggtttgattg aggctaaaga acagcaaatg    840
aacgctgctg ataattggca ttgtttactg ggccatcttg atgatagtta tcgttttgca    900
ctgagtattg gtcagtgtca gcaaataagt attgcagcag aagaagtgaa ttttaaagct    960
gttgttcgag cttcagctaa gactagctag                                    990
```

<210> SEQ ID NO 19
<211> LENGTH: 2652
<212> TYPE: PRT
<213> ORGANISM: Moritella marina

<400> SEQUENCE: 19

```
Met Ala Lys Lys Asn Thr Thr Ser Ile Lys His Ala Lys Asp Val Leu
1               5                   10                  15

Ser Ser Asp Asp Gln Gln Leu Asn Ser Arg Leu Gln Glu Cys Pro Ile
                20                  25                  30

Ala Ile Ile Gly Met Ala Ser Val Phe Ala Asp Ala Lys Asn Leu Asp
            35                  40                  45

Gln Phe Trp Asp Asn Ile Val Asp Ser Val Asp Ala Ile Ile Asp Val
        50                  55                  60

Pro Ser Asp Arg Trp Asn Ile Asp Asp His Tyr Ser Ala Asp Lys Lys
65                  70                  75                  80

Ala Ala Asp Lys Thr Tyr Cys Lys Arg Gly Gly Phe Ile Pro Glu Leu
                85                  90                  95

Asp Phe Asp Pro Met Glu Phe Gly Leu Pro Pro Asn Ile Leu Glu Leu
            100                 105                 110

Thr Asp Ile Ala Gln Leu Leu Ser Leu Ile Val Ala Arg Asp Val Leu
        115                 120                 125

Ser Asp Ala Gly Ile Gly Ser Asp Tyr Asp His Asp Lys Ile Gly Ile
    130                 135                 140

Thr Leu Gly Val Gly Gly Gly Gln Lys Gln Ile Ser Pro Leu Thr Ser
145                 150                 155                 160

Arg Leu Gln Gly Pro Val Leu Glu Lys Val Leu Lys Ala Ser Gly Ile
                165                 170                 175

Asp Glu Asp Asp Arg Ala Met Ile Ile Asp Lys Phe Lys Lys Ala Tyr
            180                 185                 190

Ile Gly Trp Glu Glu Asn Ser Phe Pro Gly Met Leu Gly Asn Val Ile
        195                 200                 205

Ala Gly Arg Ile Ala Asn Arg Phe Asp Phe Gly Thr Asn Cys Val
    210                 215                 220

Val Asp Ala Ala Cys Ala Gly Ser Leu Ala Ala Val Lys Met Ala Ile
225                 230                 235                 240
```

-continued

```
Ser Asp Leu Leu Glu Tyr Arg Ser Glu Val Met Ile Ser Gly Gly Val
            245                 250                 255

Cys Cys Asp Asn Ser Pro Phe Met Tyr Met Ser Phe Ser Lys Thr Pro
        260                 265                 270

Ala Phe Thr Thr Asn Asp Asp Ile Arg Pro Phe Asp Asp Ser Lys
            275                 280                 285

Gly Met Leu Val Gly Glu Gly Ile Gly Met Met Ala Phe Lys Arg Leu
        290                 295                 300

Glu Asp Ala Glu Arg Asp Gly Asp Lys Ile Tyr Ser Val Leu Lys Gly
305                 310                 315                 320

Ile Gly Thr Ser Ser Asp Gly Arg Phe Lys Ser Ile Tyr Ala Pro Arg
            325                 330                 335

Pro Asp Gly Gln Ala Lys Ala Leu Lys Arg Ala Tyr Glu Asp Ala Gly
            340                 345                 350

Phe Ala Pro Glu Thr Cys Gly Leu Ile Glu Gly His Gly Thr Gly Thr
        355                 360                 365

Lys Ala Gly Asp Ala Ala Glu Phe Ala Gly Leu Thr Lys His Phe Gly
        370                 375                 380

Ala Ala Ser Asp Glu Lys Gln Tyr Ile Ala Leu Gly Ser Val Lys Ser
385                 390                 395                 400

Gln Ile Gly His Thr Lys Ser Ala Ala Gly Ser Ala Gly Met Ile Lys
            405                 410                 415

Ala Ala Leu Ala Leu His His Lys Ile Leu Pro Ala Thr Ile His Ile
            420                 425                 430

Asp Lys Pro Ser Glu Ala Leu Asp Ile Lys Asn Ser Pro Leu Tyr Leu
        435                 440                 445

Asn Ser Glu Thr Arg Pro Trp Met Pro Arg Glu Asp Gly Ile Pro Arg
        450                 455                 460

Arg Ala Gly Ile Ser Ser Phe Gly Phe Gly Gly Thr Asn Phe His Ile
465                 470                 475                 480

Ile Leu Glu Glu Tyr Arg Pro Gly His Asp Ser Ala Tyr Arg Leu Asn
            485                 490                 495

Ser Val Ser Gln Thr Val Leu Ile Ser Ala Asn Asp Gln Gln Gly Ile
        500                 505                 510

Val Ala Glu Leu Asn Asn Trp Arg Thr Lys Leu Ala Val Asp Ala Asp
        515                 520                 525

His Gln Gly Phe Val Phe Asn Glu Leu Val Thr Thr Trp Pro Leu Lys
        530                 535                 540

Thr Pro Ser Val Asn Gln Ala Arg Leu Gly Phe Val Ala Arg Asn Ala
545                 550                 555                 560

Asn Glu Ala Ile Ala Met Ile Asp Thr Ala Leu Lys Gln Phe Asn Ala
                565                 570                 575

Asn Ala Asp Lys Met Thr Trp Ser Val Pro Thr Gly Val Tyr Tyr Arg
            580                 585                 590

Gln Ala Gly Ile Asp Ala Thr Gly Lys Val Val Ala Leu Phe Ser Gly
        595                 600                 605

Gln Gly Ser Gln Tyr Val Asn Met Gly Arg Glu Leu Thr Cys Asn Phe
        610                 615                 620

Pro Ser Met Met His Ser Ala Ala Ala Met Asp Lys Glu Phe Ser Ala
625                 630                 635                 640

Ala Gly Leu Gly Gln Leu Ser Ala Val Thr Phe Pro Ile Pro Val Tyr
            645                 650                 655

Thr Asp Ala Glu Arg Lys Leu Gln Glu Glu Gln Leu Arg Leu Thr Gln
```

-continued

```
                660                 665                 670
His Ala Gln Pro Ala Ile Gly Ser Leu Ser Val Gly Leu Phe Lys Thr
            675                 680                 685
Phe Lys Gln Ala Gly Phe Lys Ala Asp Phe Ala Ala Gly His Ser Phe
        690                 695                 700
Gly Glu Leu Thr Ala Leu Trp Ala Ala Asp Val Leu Ser Glu Ser Asp
705                 710                 715                 720
Tyr Met Met Leu Ala Arg Ser Arg Gly Gln Ala Met Ala Ala Pro Glu
                725                 730                 735
Gln Gln Asp Phe Asp Ala Gly Lys Met Ala Ala Val Val Gly Asp Pro
            740                 745                 750
Lys Gln Val Ala Val Ile Ile Asp Thr Leu Asp Asp Val Ser Ile Ala
        755                 760                 765
Asn Phe Asn Ser Asn Asn Gln Val Val Ile Ala Gly Thr Thr Glu Gln
        770                 775                 780
Val Ala Val Ala Val Thr Thr Leu Gly Asn Ala Gly Phe Lys Val Val
785                 790                 795                 800
Pro Leu Pro Val Ser Ala Ala Phe His Thr Pro Leu Val Arg His Ala
                805                 810                 815
Gln Lys Pro Phe Ala Lys Ala Val Asp Ser Ala Lys Phe Lys Ala Pro
            820                 825                 830
Ser Ile Pro Val Phe Ala Asn Gly Thr Gly Leu Val His Ser Ser Lys
        835                 840                 845
Pro Asn Asp Ile Lys Lys Asn Leu Lys Asn His Met Leu Glu Ser Val
        850                 855                 860
His Phe Asn Gln Glu Ile Asp Asn Ile Tyr Ala Asp Gly Gly Arg Val
865                 870                 875                 880
Phe Ile Glu Phe Gly Pro Lys Asn Val Leu Thr Lys Leu Val Glu Asn
                885                 890                 895
Ile Leu Thr Glu Lys Ser Asp Val Thr Ala Ile Ala Val Asn Ala Asn
            900                 905                 910
Pro Lys Gln Pro Ala Asp Val Gln Met Arg Gln Ala Ala Leu Gln Met
        915                 920                 925
Ala Val Leu Gly Val Ala Leu Asp Asn Ile Asp Pro Tyr Asp Ala Val
        930                 935                 940
Lys Arg Pro Leu Val Ala Pro Lys Ala Ser Pro Met Leu Met Lys Leu
945                 950                 955                 960
Ser Ala Ala Ser Tyr Val Ser Pro Lys Thr Lys Ala Phe Ala Asp
                965                 970                 975
Ala Leu Thr Asp Gly Trp Thr Val Lys Gln Ala Lys Ala Val Pro Ala
            980                 985                 990
Val Val Ser Gln Pro Gln Val Ile  Glu Lys Ile Val Glu  Val Glu Lys
        995                 1000                1005
Ile Val  Glu Arg Ile Val Glu  Val Glu Arg Ile Val  Glu Val Glu
        1010                1015                1020
Lys Ile  Val Tyr Val Asn Ala  Asp Gly Ser Leu Ile  Ser Gln Asn
        1025                1030                1035
Asn Gln  Asp Val Asn Ser Ala  Val Val Ser Asn Val  Thr Asn Ser
        1040                1045                1050
Ser Val  Thr His Ser Ser Asp  Ala Asp Leu Val Ala  Ser Ile Glu
        1055                1060                1065
Arg Ser  Val Gly Gln Phe Val  Ala His Gln Gln Gln  Leu Leu Asn
        1070                1075                1080
```

-continued

```
Val His Glu Gln Phe Met Gln Gly Pro Gln Asp Tyr Ala Lys Thr
    1085            1090                1095
Val Gln Asn Val Leu Ala Ala Gln Thr Ser Asn Glu Leu Pro Glu
    1100            1105                1110
Ser Leu Asp Arg Thr Leu Ser Met Tyr Asn Glu Phe Gln Ser Glu
    1115            1120                1125
Thr Leu Arg Val His Glu Thr Tyr Leu Asn Asn Gln Thr Ser Asn
    1130            1135                1140
Met Asn Thr Met Leu Thr Gly Ala Glu Ala Asp Val Leu Ala Thr
    1145            1150                1155
Pro Ile Thr Gln Val Val Asn Thr Ala Val Ala Thr Ser His Lys
    1160            1165                1170
Val Val Ala Pro Val Ile Ala Asn Thr Val Thr Asn Val Val Ser
    1175            1180                1185
Ser Val Ser Asn Asn Ala Ala Val Ala Val Gln Thr Val Ala Leu
    1190            1195                1200
Ala Pro Thr Gln Glu Ile Ala Pro Thr Val Ala Thr Thr Pro Ala
    1205            1210                1215
Pro Ala Leu Val Ala Ile Val Ala Glu Pro Val Ile Val Ala His
    1220            1225                1230
Val Ala Thr Glu Val Ala Pro Ile Thr Pro Ser Val Thr Pro Val
    1235            1240                1245
Val Ala Thr Gln Ala Ala Ile Asp Val Ala Thr Ile Asn Lys Val
    1250            1255                1260
Met Leu Glu Val Val Ala Asp Lys Thr Gly Tyr Pro Thr Asp Met
    1265            1270                1275
Leu Glu Leu Ser Met Asp Met Glu Ala Asp Leu Gly Ile Asp Ser
    1280            1285                1290
Ile Lys Arg Val Glu Ile Leu Gly Ala Val Gln Glu Leu Ile Pro
    1295            1300                1305
Asp Leu Pro Glu Leu Asn Pro Glu Asp Leu Ala Glu Leu Arg Thr
    1310            1315                1320
Leu Gly Glu Ile Val Asp Tyr Met Asn Ser Lys Ala Gln Ala Val
    1325            1330                1335
Ala Pro Thr Thr Val Pro Val Thr Ser Ala Pro Val Ser Pro Ala
    1340            1345                1350
Ser Ala Gly Ile Asp Leu Ala His Ile Gln Asn Val Met Leu Glu
    1355            1360                1365
Val Val Ala Asp Lys Thr Gly Tyr Pro Thr Asp Met Leu Glu Leu
    1370            1375                1380
Ser Met Asp Met Glu Ala Asp Leu Gly Ile Asp Ser Ile Lys Arg
    1385            1390                1395
Val Glu Ile Leu Gly Ala Val Gln Glu Ile Ile Thr Asp Leu Pro
    1400            1405                1410
Glu Leu Asn Pro Glu Asp Leu Ala Glu Leu Arg Thr Leu Gly Glu
    1415            1420                1425
Ile Val Ser Tyr Met Gln Ser Lys Ala Pro Val Ala Glu Ser Ala
    1430            1435                1440
Pro Val Ala Thr Ala Pro Val Ala Thr Ser Ser Ala Pro Ser Ile
    1445            1450                1455
Asp Leu Asn His Ile Gln Thr Val Met Met Asp Val Val Ala Asp
    1460            1465                1470
```

-continued

```
Lys Thr Gly Tyr Pro Thr Asp Met Leu Glu Leu Gly Met Asp Met
1475                1480                1485

Glu Ala Asp Leu Gly Ile Asp Ser Ile Lys Arg Val Glu Ile Leu
1490                1495                1500

Gly Ala Val Gln Glu Ile Ile Thr Asp Leu Pro Glu Leu Asn Pro
1505                1510                1515

Glu Asp Leu Ala Glu Leu Arg Thr Leu Gly Glu Ile Val Ser Tyr
1520                1525                1530

Met Gln Ser Lys Ala Pro Val Ala Glu Ser Ala Pro Val Ala Thr
1535                1540                1545

Ala Ser Val Ala Thr Ser Ser Ala Pro Ser Ile Asp Leu Asn His
1550                1555                1560

Ile Gln Thr Val Met Met Glu Val Val Ala Asp Lys Thr Gly Tyr
1565                1570                1575

Pro Val Asp Met Leu Glu Leu Ala Met Asp Met Glu Ala Asp Leu
1580                1585                1590

Gly Ile Asp Ser Ile Lys Arg Val Glu Ile Leu Gly Ala Val Gln
1595                1600                1605

Glu Ile Ile Thr Asp Leu Pro Glu Leu Asn Pro Glu Asp Leu Ala
1610                1615                1620

Glu Leu Arg Thr Leu Gly Glu Ile Val Ser Tyr Met Gln Ser Lys
1625                1630                1635

Ala Pro Val Ala Glu Ala Pro Ala Val Pro Val Ala Val Glu Ser
1640                1645                1650

Ala Pro Thr Ser Val Thr Ser Ser Ala Pro Ser Ile Asp Leu Asp
1655                1660                1665

His Ile Gln Asn Val Met Met Asp Val Val Ala Asp Lys Thr Gly
1670                1675                1680

Tyr Pro Ala Asn Met Leu Glu Leu Ala Met Asp Met Glu Ala Asp
1685                1690                1695

Leu Gly Ile Asp Ser Ile Lys Arg Val Glu Ile Leu Gly Ala Val
1700                1705                1710

Gln Glu Ile Ile Thr Asp Leu Pro Glu Leu Asn Pro Glu Asp Leu
1715                1720                1725

Ala Glu Leu Arg Thr Leu Glu Glu Ile Val Thr Tyr Met Gln Ser
1730                1735                1740

Lys Ala Ser Gly Val Thr Val Asn Val Val Ala Ser Pro Glu Asn
1745                1750                1755

Asn Ala Val Ser Asp Ala Phe Met Gln Ser Asn Val Ala Thr Ile
1760                1765                1770

Thr Ala Ala Ala Glu His Lys Ala Glu Phe Lys Pro Ala Pro Ser
1775                1780                1785

Ala Thr Val Ala Ile Ser Arg Leu Ser Ser Ile Ser Lys Ile Ser
1790                1795                1800

Gln Asp Cys Lys Gly Ala Asn Ala Leu Ile Val Ala Asp Gly Thr
1805                1810                1815

Asp Asn Ala Val Leu Leu Ala Asp His Leu Leu Gln Thr Gly Trp
1820                1825                1830

Asn Val Thr Ala Leu Gln Pro Thr Trp Val Ala Val Thr Thr Thr
1835                1840                1845

Lys Ala Phe Asn Lys Ser Val Asn Leu Val Thr Leu Asn Gly Val
1850                1855                1860

Asp Glu Thr Glu Ile Asn Asn Ile Ile Thr Ala Asn Ala Gln Leu
```

-continued

```
            1865                1870                1875
Asp Ala Val Ile Tyr Leu His Ala Ser Ser Glu Ile Asn Ala Ile
        1880                1885                1890
Glu Tyr Pro Gln Ala Ser Lys Gln Gly Leu Met Leu Ala Phe Leu
        1895                1900                1905
Leu Ala Lys Leu Ser Lys Val Thr Gln Ala Ala Lys Val Arg Gly
        1910                1915                1920
Ala Phe Met Ile Val Thr Gln Gln Gly Gly Ser Leu Gly Phe Asp
        1925                1930                1935
Asp Ile Asp Ser Ala Thr Ser His Asp Val Lys Thr Asp Leu Val
        1940                1945                1950
Gln Ser Gly Leu Asn Gly Leu Val Lys Thr Leu Ser His Glu Trp
        1955                1960                1965
Asp Asn Val Phe Cys Arg Ala Val Asp Ile Ala Ser Ser Leu Thr
        1970                1975                1980
Ala Glu Gln Val Ala Ser Leu Val Ser Asp Glu Leu Leu Asp Ala
        1985                1990                1995
Asn Thr Val Leu Thr Glu Val Gly Tyr Gln Gln Ala Gly Lys Gly
        2000                2005                2010
Leu Glu Arg Ile Thr Leu Thr Gly Val Ala Thr Asp Ser Tyr Ala
        2015                2020                2025
Leu Thr Ala Gly Asn Asn Ile Asp Ala Asn Ser Val Phe Leu Val
        2030                2035                2040
Ser Gly Gly Ala Lys Gly Val Thr Ala His Cys Val Ala Arg Ile
        2045                2050                2055
Ala Lys Glu Tyr Gln Ser Lys Phe Ile Leu Leu Gly Arg Ser Thr
        2060                2065                2070
Phe Ser Ser Asp Glu Pro Ser Trp Ala Ser Gly Ile Thr Asp Glu
        2075                2080                2085
Ala Ala Leu Lys Lys Ala Ala Met Gln Ser Leu Ile Thr Ala Gly
        2090                2095                2100
Asp Lys Pro Thr Pro Val Lys Ile Val Gln Leu Ile Lys Pro Ile
        2105                2110                2115
Gln Ala Asn Arg Glu Ile Ala Gln Thr Leu Ser Ala Ile Thr Ala
        2120                2125                2130
Ala Gly Gly Gln Ala Glu Tyr Val Ser Ala Asp Val Thr Asn Ala
        2135                2140                2145
Ala Ser Val Gln Met Ala Val Ala Pro Ala Ile Ala Lys Phe Gly
        2150                2155                2160
Ala Ile Thr Gly Ile Ile His Gly Ala Gly Val Leu Ala Asp Gln
        2165                2170                2175
Phe Ile Glu Gln Lys Thr Leu Ser Asp Phe Glu Ser Val Tyr Ser
        2180                2185                2190
Thr Lys Ile Asp Gly Leu Leu Ser Leu Leu Ser Val Thr Glu Ala
        2195                2200                2205
Ser Asn Ile Lys Gln Leu Val Leu Phe Ser Ser Ala Ala Gly Phe
        2210                2215                2220
Tyr Gly Asn Pro Gly Gln Ser Asp Tyr Ser Ile Ala Asn Glu Ile
        2225                2230                2235
Leu Asn Lys Thr Ala Tyr Arg Phe Lys Ser Leu His Pro Gln Ala
        2240                2245                2250
Gln Val Leu Ser Phe Asn Trp Gly Pro Trp Asp Gly Gly Met Val
        2255                2260                2265
```

```
Thr Pro Glu Leu Lys Arg Met Phe Asp Gln Arg Gly Val Tyr Ile
    2270            2275            2280

Ile Pro Leu Asp Ala Gly Ala Gln Leu Leu Asn Glu Leu Ala
    2285            2290            2295

Ala Asn Asp Asn Arg Cys Pro Gln Ile Leu Val Gly Asn Asp Leu
    2300            2305            2310

Ser Lys Asp Ala Ser Ser Asp Gln Lys Ser Asp Glu Lys Ser Thr
    2315            2320            2325

Ala Val Lys Lys Pro Gln Val Ser Arg Leu Ser Asp Ala Leu Val
    2330            2335            2340

Thr Lys Ser Ile Lys Ala Thr Asn Ser Ser Ser Leu Ser Asn Lys
    2345            2350            2355

Thr Ser Ala Leu Ser Asp Ser Ser Ala Phe Gln Val Asn Glu Asn
    2360            2365            2370

His Phe Leu Ala Asp His Met Ile Lys Gly Asn Gln Val Leu Pro
    2375            2380            2385

Thr Val Cys Ala Ile Ala Trp Met Ser Asp Ala Ala Lys Ala Thr
    2390            2395            2400

Tyr Ser Asn Arg Asp Cys Ala Leu Lys Tyr Val Gly Phe Glu Asp
    2405            2410            2415

Tyr Lys Leu Phe Lys Gly Val Val Phe Asp Gly Asn Glu Ala Ala
    2420            2425            2430

Asp Tyr Gln Ile Gln Leu Ser Pro Val Thr Arg Ala Ser Glu Gln
    2435            2440            2445

Asp Ser Glu Val Arg Ile Ala Ala Lys Ile Phe Ser Leu Lys Ser
    2450            2455            2460

Asp Gly Lys Pro Val Phe His Tyr Ala Ala Thr Ile Leu Leu Ala
    2465            2470            2475

Thr Gln Pro Leu Asn Ala Val Lys Val Glu Leu Pro Thr Leu Thr
    2480            2485            2490

Glu Ser Val Asp Ser Asn Asn Lys Val Thr Asp Glu Ala Gln Ala
    2495            2500            2505

Leu Tyr Ser Asn Gly Thr Leu Phe His Gly Glu Ser Leu Gln Gly
    2510            2515            2520

Ile Lys Gln Ile Leu Ser Cys Asp Asp Lys Gly Leu Leu Leu Ala
    2525            2530            2535

Cys Gln Ile Thr Asp Val Ala Thr Ala Lys Gln Gly Ser Phe Pro
    2540            2545            2550

Leu Ala Asp Asn Asn Ile Phe Ala Asn Asp Leu Val Tyr Gln Ala
    2555            2560            2565

Met Leu Val Trp Val Arg Lys Gln Phe Gly Leu Gly Ser Leu Pro
    2570            2575            2580

Ser Val Thr Thr Ala Trp Thr Val Tyr Arg Glu Val Val Val Asp
    2585            2590            2595

Glu Val Phe Tyr Leu Gln Leu Asn Val Val Glu His Asp Leu Leu
    2600            2605            2610

Gly Ser Arg Gly Ser Lys Ala Arg Cys Asp Ile Gln Leu Ile Ala
    2615            2620            2625

Ala Asp Met Gln Leu Leu Ala Glu Val Lys Ser Ala Gln Val Ser
    2630            2635            2640

Val Ser Asp Ile Leu Asn Asp Met Ser
    2645            2650
```

<210> SEQ ID NO 20
<211> LENGTH: 7959
<212> TYPE: DNA
<213> ORGANISM: Moritella marina

<400> SEQUENCE: 20

| | | | | | | |
|---|---|---|---|---|---|---|
| atggctaaaa | agaacaccac | atcgattaag | cacgccaagg | atgtgttaag | tagtgatgat | 60 |
| caacagttaa | attctcgctt | gcaagaatgt | ccgattgcca | tcattggtat | ggcatcggtt | 120 |
| tttgcagatg | ctaaaaactt | ggatcaattc | tgggataaca | tcgttgactc | tgtggacgct | 180 |
| attattgatg | tgcctagcga | tcgctggaac | attgacgacc | attactcggc | tgataaaaaa | 240 |
| gcagctgaca | agacatactg | caaacgcggt | ggtttcattc | cagagcttga | ttttgatccg | 300 |
| atggagtttg | gtttaccgcc | aaatatcctc | gagttaactg | acatcgctca | attgttgtca | 360 |
| ttaattgttg | ctcgtgatgt | attaagtgat | gctggcattg | gtagtgatta | tgaccatgat | 420 |
| aaaattggta | tcacgctggg | tgtcggtggt | ggtcagaaac | aaatttcgcc | attaacgtcg | 480 |
| cgcctacaag | gcccggtatt | agaaaaagta | ttaaaagcct | caggcattga | tgaagatgat | 540 |
| cgcgctatga | tcatcgacaa | atttaaaaaa | gcctacatcg | gctgggaaga | gaactcattc | 600 |
| ccaggcatgc | taggtaacgt | tattgctggt | cgtatcgcca | atcgttttga | ttttggtggt | 660 |
| actaactgtg | tggttgatgc | ggcatgcgct | ggctcccttg | cagctgttaa | aatgacgatc | 720 |
| tcagacttac | ttgaatatcg | ttcagaagtc | atgatatcgg | gtggtgtatg | ttgtgataac | 780 |
| tcgccattca | tgtatatgtc | attctcgaaa | acaccagcat | ttaccaccaa | tgatgatatc | 840 |
| cgtccgtttg | atgacgattc | aaaaggcatg | ctggttggtg | aaggtattgg | catgatggcg | 900 |
| tttaaacgtc | ttgaagatgc | tgaacgtgac | ggcgacaaaa | tttattctgt | actgaaaggt | 960 |
| atcggtacat | cttcagatgg | tcgtttcaaa | tctatttacg | ctccacgccc | agatggccaa | 1020 |
| gcaaaagcgc | taaacgtgc | ttatgaagat | gccggttttg | ccctgaaaac | atgtggtcta | 1080 |
| attgaaggcc | acggtacggg | taccaaagcg | ggtgatgccg | cagaatttgc | tggcttgacc | 1140 |
| aaacactttg | cgccgccag | tgatgaaaag | caatatatcg | ccttaggctc | agttaaatcg | 1200 |
| caaattggtc | atactaaatc | tgcggctggc | tctgcgggta | tgattaaggc | ggcattagcg | 1260 |
| ctgcatcata | aaatcttacc | tgcaacgatc | catatcgata | aaccaagtga | agccttggat | 1320 |
| atcaaaaaca | gcccgttata | cctaaacagc | gaaacgcgtc | cttggatgcc | acgtgaagat | 1380 |
| ggtattccac | gtcgtgcagg | tatcagctca | tttggttttg | gcggcaccaa | cttccatatt | 1440 |
| attttagaag | agtatcgccc | aggtcacgat | agcgcatatg | gcttaaactc | agtgagccaa | 1500 |
| actgtgttga | tctcggcaaa | cgaccaacaa | ggtattgttg | ctgagttaaa | taactggcgt | 1560 |
| actaaactgg | ctgtcgatgc | tgatcatcaa | gggtttgtat | ttaatgagtt | agtgacaacg | 1620 |
| tggccattaa | aaacccccatc | cgttaaccaa | gctcgtttag | gttttgttgc | gcgtaatgca | 1680 |
| aatgaagcga | tcgcgatgat | tgatacggca | ttgaaacaat | tcaatgcgaa | cgcagataaa | 1740 |
| atgacatggt | cagtacctac | cggggtttac | tatcgtcaag | ccggtattga | tgcaacaggt | 1800 |
| aaagtggttg | cgctattctc | agggcaaggt | tcgcaatacg | tgaacatggg | tcgtgaatta | 1860 |
| acctgtaact | tcccaagcat | gatgcacagt | gctgcggcga | tggataaaga | gttcagtgcc | 1920 |
| gctggtttag | gccagttatc | tgcagttact | ttccctatcc | ctgtttatac | ggatgccgag | 1980 |
| cgtaagctac | aagaagagca | attacgttta | acgcaacatg | cgcaaccagc | gattggtagt | 2040 |
| ttgagtgttg | gtctgttcaa | aacgtttaag | caagcaggtt | ttaaagctga | ttttgctgcc | 2100 |
| ggtcatagtt | tcggtgagtt | aaccgcatta | tgggctgccg | atgtattgag | cgaaagcgat | 2160 |

```
tacatgatgt tagcgcgtag tcgtggtcaa gcaatggctg cgccagagca acaagatttt   2220
gatgcaggta agatggccgc tgttgttggt gatccaaagc aagtcgctgt gatcattgat   2280
acccttgatg atgtctctat tgctaacttc aactcgaata accaagttgt tattgctggt   2340
actacggagc aggttgctgt agcggttaca accttaggta atgctggttt caaagttgtg   2400
ccactgccgg tatctgctgc gttccataca cctttagttc gtcacgcgca aaaaccattt   2460
gctaaagcgg ttgatagcgc taaatttaaa gcgccaagca ttccagtgtt tgctaatggc   2520
acaggcttgg tgcattcaag caaaccgaat gacattaaga aaaacctgaa aaaccacatg   2580
ctggaatctg ttcatttcaa tcaagaaatt gacaacatct atgctgatgg tggccgcgta   2640
tttatcgaat ttggtccaaa gaatgtatta actaaattgg ttgaaaacat tctcactgaa   2700
aaatctgatg tgactgctat cgcggttaat gctaatccta acaacctgc ggacgtacaa    2760 atgcgccaag ctgcgctgca aatggcagtg cttggtgtcg cattagacaa tattgacccg   2820
tacgacgccg ttaagcgtcc acttgttgcg ccgaaagcat caccaatgtt gatgaagtta   2880
tctgcagcgt cttatgttag tccgaaaacg aagaaagcgt tgctgatgc attgactgat    2940 ggctggactg ttaagcaagc gaaagctgta cctgctgttg tgtcacaacc acaagtgatt   3000
gaaaagatcg ttgaagttga aaagatagtt gaacgcattg tcgaagtaga gcgtattgtc   3060
gaagtagaaa aaatcgtcta cgttaatgct gacggttcgc ttatatcgca aaataatcaa   3120
gacgttaaca gcgctgttgt tagcaacgtg actaatagct cagtgactca tagcagtgat   3180
gctgaccttg ttgcctctat tgaacgcagt gttggtcaat tgttgcaca ccaacagcaa    3240 ttattaaatg tacatgaaca gtttatgcaa ggtccacaag actacgcgaa acagtgcag    3300 aacgtacttg ctgcgcagac gagcaatgaa ttaccgaaaa gtttagaccg tacattgtct   3360
atgtataacg agttccaatc agaaacgcta cgtgtacatg aaacgtacct gaacaatcag   3420
acgagcaaca tgaacaccat gcttactggt gctgaagctg atgtgctagc aaccccaata   3480
actcaggtag tgaatacagc cgttgccact agtcacaagg tagttgctcc agttattgct   3540
aatacagtga cgaatgttgt atctagtgtc agtaataacg cggcggttgc agtgcaaact   3600
gtggcattag cgcctacgca agaaatcgct ccaacagtcg ctactacgcc agcacccgca   3660
ttggttgcta tcgtggctga acctgtgatt gttgcgcatg ttgctacaga agttgcacca   3720
attacaccat cagttacacc agttgtcgca actcaagcgg ctatcgatgt agcaactatt   3780
aacaaagtaa tgttagaagt tgttgctgat aaaaccggtt atccaacgga tatgctggaa   3840
ctgagcatgg acatggaagc tgacttaggt atcgactcaa tcaaacgtgt tgagatatta   3900
ggcgcagtac aggaattgat ccctgactta cctgaactta atcctgaaga tcttgctgag   3960
ctacgcacgc ttggtgagat tgtcgattac atgaattcaa aagcccaggc tgtagctcct   4020
acaacagtac ctgtaacaag tgcacctgtt tcgcctgcat ctgctggtat tgatttagcc   4080
cacatccaaa acgtaatgtt agaagtggtt gcagacaaaa ccggttaccc aacagacatg   4140
ctagaactga gcatggatat ggaagctgac ttaggtattg attcaatcaa gcgtgtggaa   4200
atcttaggtg cagtacagga gatcataact gatttacctg agctaaaccc tgaagatctt   4260
gctgaattac gcaccctagg tgaaatcgtt agttacatgc aaagcaaagc gccagtcgct   4320
gaaagtgcgc cagtggcgac ggctcctgta gcaacaagct cagcaccgtc tatcgatttg   4380
aaccacattc aaacagtgat gatggatgta gttgcagata agactggtta tccaactgac   4440
atgctagaac ttggcatgga catggaagct gatttaggta tcgattcaat caaacgtgtg   4500
```

```
gaaatattag gcgcagtgca ggagatcatc actgatttac ctgagctaaa cccagaagac    4560
ctcgctgaat tacgcacgct aggtgaaatc gttagttaca tgcaaagcaa agcgccagtc    4620
gctgagagtg cgccagtagc gacggcttct gtagcaacaa gctctgcacc gtctatcgat    4680
ttaaaccata tccaaacagt gatgatggaa gtggttgcag acaaaaccgg ttatccagta    4740
gacatgttag aacttgctat ggacatggaa gctgacctag gtatcgattc aatcaagcgt    4800
gtagaaattt taggtgcggt acaggaaatc attactgact tacctgagct taaccctgaa    4860
gatcttgctg aactacgtac attaggtgaa atcgttagtt acatgcaaag caaagcgccc    4920
gtagctgaag cgcctgcagt acctgttgca gtagaaagtg cacctactag tgtaacaagc    4980
tcagcaccgt ctatcgattt agaccacatc caaaatgtaa tgatggatgt tgttgctgat    5040
aagactggtt atcctgccaa tatgcttgaa ttagcaatgg acatggaagc cgaccttggt    5100
attgattcaa tcaagcgtgt tgaaattcta ggcgcggtac aggagatcat tactgattta    5160
cctgaactaa acccagaaga cttagctgaa ctacgtacgt tagaagaaat tgtaacctac    5220
atgcaaagca aggcgagtgg tgttactgta aatgtagtgg ctagccctga aaataatgct    5280
gtatcagatg catttatgca aagcaatgtg gcgactatca cagccgcggc agaacataag    5340
gcggaattta aaccggcgcc gagcgcaacc gttgctatct ctcgtctaag ctctatcagt    5400
aaaataagcc aagattgtaa aggtgctaac gccttaatcg tagctgatgg cactgataat    5460
gctgtgttac ttgcagacca cctattgcaa actggctgga atgtaactgc attgcaacca    5520
acttgggtag ctgtaacaac gacgaaagca tttaataagt cagtgaacct ggtgacttta    5580
aatggcgttg atgaaactga atcaacaac attattactg ctaacgcaca attggatgca    5640
gttatctatc tgcacgcaag tagcgaaatt aatgctatcg aatacccaca agcatctaag    5700
caaggcctga tgttagcctt cttattagcg aaattgagta agtaactca agccgctaaa    5760 gtgcgtggcg cctttatgat tgttactcag cagggtggtt cattaggttt tgatgatatc    5820
gattctgcta caagtcatga tgtgaaaaca gacctagtac aaagcggctt aaacggttta    5880
gttaagacac tgtctcacga gtgggataac gtattctgtc gtgcggttga tattgcttcg    5940
tcattaacgg ctgaacaagt tgcaagcctt gttagtgatg aactacttga tgctaacact    6000
gtattaacag aagtgggtta tcaacaagct ggtaaaggcc ttgaacgtat cacgttaact    6060
ggtgtggcta ctgacagcta tgcattaaca gctggcaata acatcgatgc taactcggta    6120
tttttagtga gtggtggcgc aaaaggtgta actgcacatt gtgttgctcg tatagctaaa    6180
gaatatcagt ctaagttcat cttattggga cgttcaacgt tctcaagtga cgaaccgagc    6240
tgggcaagtg gtattactga tgaagcggcg ttaaagaaag cagcgatgca gtctttgatt    6300
acagcaggtg ataaaccaac acccgttaag atcgtacagc taatcaaacc aatccaagct    6360
aatcgtgaaa ttgcgcaaac cttgtctgca attaccgctg ctggtggcca agctgaatat    6420
gtttctgcag atgtaactaa tgcagcaagc gtacaaatgg cagtcgctcc agctatcgct    6480
aagttcggtg caatcactgg catcattcat ggcgcgggtg tgttagctga ccaattcatt    6540
gagcaaaaaa cactgagtga tttgagtct gtttacagca ctaaaattga cggtttgtta    6600
tcgctactat cagtcactga agcaagcaac atcaagcaat tggtattgtt ctcgtcagcg    6660
gctggtttct acggtaaccc cggccagtct gattactcga ttccaatga gatcttaaat    6720 aaaaccgcat accgctttaa atcattgcac ccacaagctc aagtattgag ctttaactgg    6780
ggtccttggg acggtggcat ggtaacgcct gagcttaaac gtatgtttga ccaacgtggt    6840
gtttacatta ttccacttga tgcaggtgca cagttattgc tgaatgaact agccgctaat    6900
```

-continued

```
gataaccgtt gtccacaaat cctcgtgggt aatgacttat ctaaagatgc tagctctgat    6960
caaaagtctg atgaaaagag tactgctgta aaaaagccac aagttagtcg tttatcagat    7020
gctttagtaa ctaaaagtat caaagcgact aacagtagct ctttatcaaa caagactagt    7080
gctttatcag acagtagtgc ttttcaggtt aacgaaaacc acttttttagc tgaccacatg    7140 atcaaaggca atcaggtatt accaacggta tgcgcgattg cttggatgag tgatgcagca    7200
aaagcgactt atagtaaccg agactgtgca ttgaagtatg tcggtttcga agactataaa    7260
ttgtttaaag gtgtggtttt tgatggcaat gaggcggcgg attaccaaat ccaattgtcg    7320
cctgtgacaa gggcgtcaga acaggattct gaagtccgta ttgccgcaaa gatctttagc    7380
ctgaaaagtg acggtaaaacc tgtgtttcat tatgcagcga caatattgtt agcaactcag    7440
ccacttaatg ctgtgaaggt agaacttccg acattgacag aaagtgttga tagcaacaat    7500
aaagtaactg atgaagcaca agcgttatac agcaatggca ccttgttcca cggtgaaagt    7560
ctgcagggca ttaagcagat attaagttgt gacgacaagg gcctgctatt ggcttgtcag    7620
ataaccgatg ttgcaacagc taagcaggga tccttcccgt tagctgacaa caatatcttt    7680
gccaatgatt tggtttatca ggctatgttg gtctgggtgc gcaaacaatt tggtttaggt    7740
agcttacctt cggtgacaac ggcttggact gtgtatcgtg aagtggttgt agatgaagta    7800
ttttatctgc aacttaatgt tgttgagcat gatctattgg gttcacgcgg cagtaaagcc    7860
cgttgtgata ttcaattgat tgctgctgat atgcaattac ttgccgaagt gaaatcagcg    7920
caagtcagtg tcagtgacat tttgaacgat atgtcatga                           7959
```

<210> SEQ ID NO 21
<211> LENGTH: 883
<212> TYPE: PRT
<213> ORGANISM: Moritella marina

<400> SEQUENCE: 21

```
Met Thr Glu Leu Ala Val Ile Gly Met Asp Ala Lys Phe Ser Gly Gln
1               5                  10                  15

Asp Asn Ile Asp Arg Val Glu Arg Ala Phe Tyr Glu Gly Ala Tyr Val
            20                  25                  30

Gly Asn Val Ser Arg Val Ser Thr Glu Ser Asn Val Ile Ser Asn Gly
        35                  40                  45

Glu Glu Gln Val Ile Thr Ala Met Thr Val Leu Asn Ser Val Ser Leu
    50                  55                  60

Leu Ala Gln Thr Asn Gln Leu Asn Ile Ala Asp Ile Ala Val Leu Leu
65                  70                  75                  80

Ile Ala Asp Val Lys Ser Ala Asp Asp Gln Leu Val Val Gln Ile Ala
                85                  90                  95

Ser Ala Ile Glu Lys Gln Cys Ala Ser Cys Val Val Ile Ala Asp Leu
            100                 105                 110

Gly Gln Ala Leu Asn Gln Val Ala Asp Leu Val Asn Asn Gln Asp Cys
        115                 120                 125

Pro Val Ala Val Ile Gly Met Asn Asn Ser Val Asn Leu Ser Arg His
    130                 135                 140

Asp Leu Glu Ser Val Thr Ala Thr Ile Ser Phe Asp Glu Thr Phe Asn
145                 150                 155                 160

Gly Tyr Asn Asn Val Ala Gly Phe Ala Ser Leu Leu Ile Ala Ser Thr
                165                 170                 175

Ala Phe Ala Asn Ala Lys Gln Cys Tyr Ile Tyr Ala Asn Ile Lys Gly
```

-continued

```
              180                 185                 190
Phe Ala Gln Ser Gly Val Asn Ala Gln Phe Asn Val Gly Asn Ile Ser
            195                 200                 205

Asp Thr Ala Lys Thr Ala Leu Gln Gln Ala Ser Ile Thr Ala Glu Gln
210                 215                 220

Val Gly Leu Leu Glu Val Ser Ala Val Ala Asp Ser Ala Ile Ala Leu
225                 230                 235                 240

Ser Glu Ser Gln Gly Leu Met Ser Ala Tyr His His Thr Gln Thr Leu
                245                 250                 255

His Thr Ala Leu Ser Ser Ala Arg Ser Val Thr Gly Glu Gly Gly Cys
            260                 265                 270

Phe Ser Gln Val Ala Gly Leu Leu Lys Cys Val Ile Gly Leu His Gln
        275                 280                 285

Arg Tyr Ile Pro Ala Ile Lys Asp Trp Gln Gln Pro Ser Asp Asn Gln
290                 295                 300

Met Ser Arg Trp Arg Asn Ser Pro Phe Tyr Met Pro Val Asp Ala Arg
305                 310                 315                 320

Pro Trp Phe Pro His Ala Asp Gly Ser Ala His Ile Ala Ala Tyr Ser
                325                 330                 335

Cys Val Thr Ala Asp Ser Tyr Cys His Ile Leu Leu Gln Glu Asn Val
            340                 345                 350

Leu Gln Glu Leu Val Leu Lys Glu Thr Val Leu Gln Asp Asn Asp Leu
        355                 360                 365

Thr Glu Ser Lys Leu Gln Thr Leu Glu Gln Asn Asn Pro Val Ala Asp
370                 375                 380

Leu Arg Thr Asn Gly Tyr Phe Ala Ser Ser Glu Leu Ala Leu Ile Ile
385                 390                 395                 400

Val Gln Gly Asn Asp Glu Ala Gln Leu Arg Cys Glu Leu Glu Thr Ile
                405                 410                 415

Thr Gly Gln Leu Ser Thr Thr Gly Ile Ser Thr Ile Ser Ile Lys Gln
            420                 425                 430

Ile Ala Ala Asp Cys Tyr Ala Arg Asn Asp Thr Asn Lys Ala Tyr Ser
        435                 440                 445

Ala Val Leu Ile Ala Glu Thr Ala Glu Glu Leu Ser Lys Glu Ile Thr
450                 455                 460

Leu Ala Phe Ala Gly Ile Ala Ser Val Phe Asn Glu Asp Ala Lys Glu
465                 470                 475                 480

Trp Lys Thr Pro Lys Gly Ser Tyr Phe Thr Ala Gln Pro Ala Asn Lys
                485                 490                 495

Gln Ala Ala Asn Ser Thr Gln Asn Gly Val Thr Phe Met Tyr Pro Gly
            500                 505                 510

Ile Gly Ala Thr Tyr Val Gly Leu Gly Arg Asp Leu Phe His Leu Phe
        515                 520                 525

Pro Gln Ile Tyr Gln Pro Val Ala Leu Ala Asp Asp Ile Gly Glu
530                 535                 540

Ser Leu Lys Asp Thr Leu Leu Asn Pro Arg Ser Ile Ser Arg His Ser
545                 550                 555                 560

Phe Lys Glu Leu Lys Gln Leu Asp Leu Asp Leu Arg Gly Asn Leu Ala
                565                 570                 575

Asn Ile Ala Glu Ala Gly Val Gly Phe Ala Cys Val Phe Thr Lys Val
            580                 585                 590

Phe Glu Glu Val Phe Ala Val Lys Ala Asp Phe Ala Thr Gly Tyr Ser
        595                 600                 605
```

```
Met Gly Glu Val Ser Met Tyr Ala Ala Leu Gly Cys Trp Gln Gln Pro
610                 615                 620

Gly Leu Met Ser Ala Arg Leu Ala Gln Ser Asn Thr Phe Asn His Gln
625                 630                 635                 640

Leu Cys Gly Glu Leu Arg Thr Leu Arg Gln His Trp Gly Met Asp Asp
                645                 650                 655

Val Ala Asn Gly Thr Phe Glu Gln Ile Trp Glu Thr Tyr Thr Ile Lys
            660                 665                 670

Ala Thr Ile Glu Gln Val Glu Ile Ala Ser Ala Asp Glu Asp Arg Val
        675                 680                 685

Tyr Cys Thr Ile Ile Asn Thr Pro Asp Ser Leu Leu Leu Ala Gly Tyr
    690                 695                 700

Pro Glu Ala Cys Gln Arg Val Ile Lys Asn Leu Gly Val Arg Ala Met
705                 710                 715                 720

Ala Leu Asn Met Ala Asn Ala Ile His Ser Ala Pro Ala Tyr Ala Glu
                725                 730                 735

Tyr Asp His Met Val Glu Leu Tyr His Met Asp Val Thr Pro Arg Ile
                740                 745                 750

Asn Thr Lys Met Tyr Ser Ser Cys Tyr Leu Pro Ile Pro Gln Arg
            755                 760                 765

Ser Lys Ala Ile Ser His Ser Ile Ala Lys Cys Leu Cys Asp Val Val
        770                 775                 780

Asp Phe Pro Arg Leu Val Asn Thr Leu His Asp Lys Gly Ala Arg Val
785                 790                 795                 800

Phe Ile Glu Met Gly Pro Gly Arg Ser Leu Cys Ser Trp Val Asp Lys
                805                 810                 815

Ile Leu Val Asn Gly Asp Gly Asp Asn Lys Lys Gln Ser Gln His Val
                820                 825                 830

Ser Val Pro Val Asn Ala Lys Gly Thr Ser Asp Glu Leu Thr Tyr Ile
        835                 840                 845

Arg Ala Ile Ala Lys Leu Ile Ser His Gly Val Asn Leu Asn Leu Asp
850                 855                 860

Ser Leu Phe Asn Gly Ser Ile Leu Val Lys Ala Gly His Ile Ala Asn
865                 870                 875                 880

Thr Asn Lys

<210> SEQ ID NO 22
<211> LENGTH: 2652
<212> TYPE: DNA
<213> ORGANISM: Moritella marina

<400> SEQUENCE: 22
atgacggaat tagctgttat tggtatggat gctaaattta gcggacaaga caatattgac      60
cgtgtggaac gcgctttcta tgaaggtgct tatgtaggta atgttagccg cgttagtacc     120
gaatctaatg ttattagcaa tggcgaagaa caagttatta ctgccatgac agttcttaac     180
tctgtcagtc tactagcgca aacgaatcag ttaaatatag ctgatatcgc ggtgttgctg     240
attgctgatg taaaaagtgc tgatgatcag cttgtagtcc aaattgcatc agcaattgaa     300
aaacagtgtg cgagttgtgt tgttattgct gatttaggcc aagcattaaa tcaagtagct     360
gatttagtta ataaccaaga ctgtcctgtg ctgtaattg gcatgaataa ctcggttaat     420
ttatctcgtc atgatcttga atctgtaact gcaacaatca gctttgatga accttcaat      480
ggttataaca atgtagctgg gttcgcgagt ttacttatcg cttcaactgc gtttgccaat     540
```

```
gctaagcaat gttatatata cgccaacatt aagggcttcg ctcaatcggg cgtaaatgct    600
caatttaacg ttggaaacat tagcgatact gcaaagaccg cattgcagca agctagcata    660
actgcagagc aggttggttt gttagaagtg tcagcagtcg ctgattcggc aatcgcattg    720
tctgaaagcc aaggtttaat gtctgcttat catcatacgc aaactttgca tactgcatta    780
agcagtgccc gtagtgtgac tggtgaaggc gggtgttttt cacaggtcgc aggtttattg    840
aaatgtgtaa ttggtttaca tcaacgttat attccggcga ttaaagattg caacaaccg     900
agtgacaatc aaatgtcacg gtggcggaat tcaccattct atatgcctgt agatgctcga    960
ccttggttcc cacatgctga tggctctgca cacattgccg cttatagttg tgtgactgct   1020
gacagctatt gtcatattct tttacaagaa aacgtcttac aagaacttgt tttgaaagaa   1080
acagtcttgc aagataatga cttaactgaa agcaagcttc agactcttga acaaaacaat   1140
ccagtagctg atctgcgcac taatggttac tttgcatcga gcgagttagc attaatcata   1200
gtacaaggta atgacgaagc acaattacgc tgtgaattag aaactattac agggcagtta   1260
agtactactg gcataagtac tatcagtatt aaacagatcg cagcgagactg ttatgcccgt   1320
aatgatacta acaaagccta tagcgcagtg cttattgccg agactgctga agagttaagc   1380
aaagaaataa ccttggcgtt tgctggtatc gctagcgtgt ttaatgaaga tgctaaagaa   1440
tggaaaaccc cgaagggcag ttattttacc gcgcagcctg caaataaaca ggctgctaac   1500
agcacacaga atggtgtcac cttcatgtac ccaggtattg gtgctacata tgttggttta   1560
gggcgtgatc tatttcatct attcccacag atttatcagc ctgtagcggc tttagccgat   1620
gacattggcg aaagtctaaa agatacttta cttaatccac gcagtattag tcgtcatagc   1680
tttaagaac tcaagcagtt ggatctggac ctgcgcggta acttagccaa tatcgctgaa   1740
gccggtgtgg gttttgcttg tgtgtttacc aaggtatttg aagaagtctt tgccgttaaa   1800
gctgactttg ctacaggtta tagcatgggt gaagtaagca tgtatgcagc actaggctgc   1860
tggcagcaac cgggattgat gagtgctcgc cttgcacaat cgaataccct taatcatcaa   1920
ctttgcggcg agtaagaac actacgtcag cattggggca tggatgatgt agctaacggt   1980
acgttcgagc agatctggga aacctatacc attaaggcaa cgattgaaca ggtcgaaatt   2040
gcctctgcag atgaagatcg tgtgtattgc accattatca atacacctga tagcttgttg   2100
ttagccggtt atccagaagc ctgtcagcga gtcattaaga atttaggtgt gcgtgcaatg   2160
gcattgaata tggcgaacgc aattcacagc gcgccagctt atgccgaata cgatcatatg   2220
gttgagctat accatatgga tgttactcca cgtattaata ccaagatgta ttcaagctca   2280
tgttatttac cgattccaca acgcagcaaa gcgatttccc acagtattgc taaatgtttg   2340
tgtgatgtgg tggatttccc acgtttggtt aatacccttac atgacaaagg tgcgcgggta   2400
ttcattgaaa tgggtccagg tcgttcgtta tgtagctggg tagataagat cttagttaat   2460
ggcgatggcg ataataaaaa gcaaagccaa catgtatctg ttcctgtgaa tgccaaaggc   2520
accagtgatg aacttactta tattcgtgcg attgctaagt taattagtca tggcgtgaat   2580
ttgaatttag atagcttgtt taacgggtca atcctggtta aagcaggcca tatagcaaac   2640
acgaacaaat ag                                                       2652
```

<210> SEQ ID NO 23
<211> LENGTH: 2011
<212> TYPE: PRT
<213> ORGANISM: Moritella marina

<400> SEQUENCE: 23

```
Met Glu Asn Ile Ala Val Val Gly Ile Ala Asn Leu Phe Pro Gly Ser
1               5                   10                  15

Gln Ala Pro Asp Gln Phe Trp Gln Gln Leu Glu Gln Gln Asp Cys
            20                  25                  30

Arg Ser Lys Ala Thr Ala Val Gln Met Gly Val Asp Pro Ala Lys Tyr
            35                  40                  45

Thr Ala Asn Lys Gly Asp Thr Asp Lys Phe Tyr Cys Val His Gly Gly
        50                  55                  60

Tyr Ile Ser Asp Phe Asn Phe Asp Ala Ser Gly Tyr Gln Leu Asp Asn
65                  70                  75                  80

Asp Tyr Leu Ala Gly Leu Asp Asp Leu Asn Gln Trp Gly Leu Tyr Val
                85                  90                  95

Thr Lys Gln Ala Leu Thr Asp Ala Gly Tyr Trp Gly Ser Thr Ala Leu
            100                 105                 110

Glu Asn Cys Gly Val Ile Leu Gly Asn Leu Ser Phe Pro Thr Lys Ser
            115                 120                 125

Ser Asn Gln Leu Phe Met Pro Leu Tyr His Gln Val Val Asp Asn Ala
130                 135                 140

Leu Lys Ala Val Leu His Pro Asp Phe Gln Leu Thr His Tyr Thr Ala
145                 150                 155                 160

Pro Lys Lys Thr His Ala Asp Asn Ala Leu Val Ala Gly Tyr Pro Ala
                165                 170                 175

Ala Leu Ile Ala Gln Ala Ala Gly Leu Gly Gly Ser His Phe Ala Leu
            180                 185                 190

Asp Ala Ala Cys Ala Ser Ser Cys Tyr Ser Val Lys Leu Ala Cys Asp
            195                 200                 205

Tyr Leu His Thr Gly Lys Ala Asn Met Met Leu Ala Gly Ala Val Ser
210                 215                 220

Ala Ala Asp Pro Met Phe Val Asn Met Gly Phe Ser Ile Phe Gln Ala
225                 230                 235                 240

Tyr Pro Ala Asn Asn Val His Ala Pro Phe Asp Gln Asn Ser Gln Gly
                245                 250                 255

Leu Phe Ala Gly Glu Gly Ala Gly Met Met Val Leu Lys Arg Gln Ser
            260                 265                 270

Asp Ala Val Arg Asp Gly Asp His Ile Tyr Ala Ile Ile Lys Gly Gly
            275                 280                 285

Ala Leu Ser Asn Asp Gly Lys Gly Glu Phe Val Leu Ser Pro Asn Thr
            290                 295                 300

Lys Gly Gln Val Leu Val Tyr Glu Arg Ala Tyr Ala Asp Ala Asp Val
305                 310                 315                 320

Asp Pro Ser Thr Val Asp Tyr Ile Glu Cys His Ala Thr Gly Thr Pro
                325                 330                 335

Lys Gly Asp Asn Val Glu Leu Arg Ser Met Glu Thr Phe Phe Ser Arg
            340                 345                 350

Val Asn Asn Lys Pro Leu Leu Gly Ser Val Lys Ser Asn Leu Gly His
            355                 360                 365

Leu Leu Thr Ala Ala Gly Met Pro Gly Met Thr Lys Ala Met Leu Ala
370                 375                 380

Leu Gly Lys Gly Leu Ile Pro Ala Thr Ile Asn Leu Lys Gln Pro Leu
385                 390                 395                 400

Gln Ser Lys Asn Gly Tyr Phe Thr Gly Glu Gln Met Pro Thr Thr Thr
                405                 410                 415
```

-continued

```
Val Ser Trp Pro Thr Thr Pro Gly Ala Lys Ala Asp Lys Pro Arg Thr
            420                 425                 430

Ala Gly Val Ser Val Phe Gly Phe Gly Gly Ser Asn Ala His Leu Val
        435                 440                 445

Leu Gln Gln Pro Thr Gln Thr Leu Glu Thr Asn Phe Ser Val Ala Lys
    450                 455                 460

Pro Arg Glu Pro Leu Ala Ile Ile Gly Met Asp Ser His Phe Gly Ser
465                 470                 475                 480

Ala Ser Asn Leu Ala Gln Phe Lys Thr Leu Leu Asn Asn Gln Asn
                485                 490                 495

Thr Phe Arg Glu Leu Pro Glu Gln Arg Trp Lys Gly Met Glu Ser Asn
            500                 505                 510

Ala Asn Val Met Gln Ser Leu Gln Leu Arg Lys Ala Pro Lys Gly Ser
        515                 520                 525

Tyr Val Glu Gln Leu Asp Ile Asp Phe Leu Arg Phe Lys Val Pro Pro
    530                 535                 540

Asn Glu Lys Asp Cys Leu Ile Pro Gln Gln Leu Met Met Met Gln Val
545                 550                 555                 560

Ala Asp Asn Ala Ala Lys Asp Gly Gly Leu Val Gly Arg Asn Val
                565                 570                 575

Ala Val Leu Val Ala Met Gly Met Glu Leu Glu Leu His Gln Tyr Arg
            580                 585                 590

Gly Arg Val Asn Leu Thr Thr Gln Ile Glu Asp Ser Leu Leu Gln Gln
        595                 600                 605

Gly Ile Asn Leu Thr Val Glu Gln Arg Glu Glu Leu Thr Asn Ile Ala
    610                 615                 620

Lys Asp Gly Val Ala Ser Ala Ala Gln Leu Asn Gln Tyr Thr Ser Phe
625                 630                 635                 640

Ile Gly Asn Ile Met Ala Ser Arg Ile Ser Ala Leu Trp Asp Phe Ser
                645                 650                 655

Gly Pro Ala Ile Thr Val Ser Ala Glu Glu Asn Ser Val Tyr Arg Cys
            660                 665                 670

Val Glu Leu Ala Glu Asn Leu Phe Gln Thr Ser Asp Val Glu Ala Val
        675                 680                 685

Ile Ile Ala Ala Val Asp Leu Ser Gly Ser Ile Glu Asn Ile Thr Leu
    690                 695                 700

Arg Gln His Tyr Gly Pro Val Asn Glu Lys Gly Ser Val Ser Glu Cys
705                 710                 715                 720

Gly Pro Val Asn Glu Ser Ser Val Thr Asn Asn Ile Leu Asp Gln
                725                 730                 735

Gln Gln Trp Leu Val Gly Glu Gly Ala Ala Ile Val Val Lys Pro
            740                 745                 750

Ser Ser Gln Val Thr Ala Asp Gln Val Tyr Ala Arg Ile Asp Ala Val
        755                 760                 765

Ser Phe Ala Pro Gly Ser Asn Ala Lys Ala Ile Thr Ile Ala Ala Asp
    770                 775                 780

Lys Ala Leu Thr Leu Ala Gly Ile Ser Ala Ala Asp Val Ala Ser Val
785                 790                 795                 800

Glu Ala His Ala Ser Gly Phe Ser Ala Glu Asn Asn Ala Glu Lys Thr
                805                 810                 815

Ala Leu Pro Thr Leu Tyr Pro Ser Ala Ser Ile Ser Ser Val Lys Ala
            820                 825                 830
```

-continued

```
Asn Ile Gly His Thr Phe Asn Ala Ser Gly Met Ala Ser Ile Ile Lys
        835                 840                 845

Thr Ala Leu Leu Asp Gln Asn Thr Ser Gln Asp Gln Lys Ser Lys
850                 855                 860

His Ile Ala Ile Asn Gly Leu Gly Arg Asp Asn Ser Cys Ala His Leu
865                 870                 875                 880

Ile Leu Ser Ser Ser Ala Gln Ala His Gln Val Ala Pro Ala Pro Val
                885                 890                 895

Ser Gly Met Ala Lys Gln Arg Pro Gln Leu Val Lys Thr Ile Lys Leu
            900                 905                 910

Gly Gly Gln Leu Ile Ser Asn Ala Ile Val Asn Ser Ala Ser Ser Ser
        915                 920                 925

Leu His Ala Ile Lys Ala Gln Phe Ala Gly Lys His Leu Asn Lys Val
930                 935                 940

Asn Gln Pro Val Met Met Asp Asn Leu Lys Pro Gln Gly Ile Ser Ala
945                 950                 955                 960

His Ala Thr Asn Glu Tyr Val Val Thr Gly Ala Ala Asn Thr Gln Ala
                965                 970                 975

Ser Asn Ile Gln Ala Ser His Val Gln Ala Ser Ser His Ala Gln Glu
            980                 985                 990

Ile Ala Pro Asn Gln Val Gln Asn Met Gln Ala Thr Ala Ala Ala Val
        995                 1000                1005

Ser Ser Pro Leu Ser Gln His Gln His Thr Ala Gln Pro Val Ala
1010                1015                1020

Ala Pro Ser Val Val Gly Val Thr Val Lys His Lys Ala Ser Asn
1025                1030                1035

Gln Ile His Gln Gln Ala Ser Thr His Lys Ala Phe Leu Glu Ser
1040                1045                1050

Arg Leu Ala Ala Gln Lys Asn Leu Ser Gln Leu Val Glu Leu Gln
1055                1060                1065

Thr Lys Leu Ser Ile Gln Thr Gly Ser Asp Asn Thr Ser Asn Asn
1070                1075                1080

Thr Ala Ser Thr Ser Asn Thr Val Leu Thr Asn Pro Val Ser Ala
1085                1090                1095

Thr Pro Leu Thr Leu Val Ser Asn Ala Pro Val Val Ala Thr Asn
1100                1105                1110

Leu Thr Ser Thr Glu Ala Lys Ala Gln Ala Ala Ala Thr Gln Ala
1115                1120                1125

Gly Phe Gln Ile Lys Gly Pro Val Gly Tyr Asn Tyr Pro Pro Leu
1130                1135                1140

Gln Leu Ile Glu Arg Tyr Asn Lys Pro Glu Asn Val Ile Tyr Asp
1145                1150                1155

Gln Ala Asp Leu Val Glu Phe Ala Glu Gly Asp Ile Gly Lys Val
1160                1165                1170

Phe Gly Ala Glu Tyr Asn Ile Ile Asp Gly Tyr Ser Arg Arg Val
1175                1180                1185

Arg Leu Pro Thr Ser Asp Tyr Leu Leu Val Thr Arg Val Thr Glu
1190                1195                1200

Leu Asp Ala Lys Val His Glu Tyr Lys Lys Ser Tyr Met Cys Thr
1205                1210                1215

Glu Tyr Asp Val Pro Val Asp Ala Pro Phe Leu Ile Asp Gly Gln
1220                1225                1230

Ile Pro Trp Ser Val Ala Val Glu Ser Gly Gln Cys Asp Leu Met
```

-continued

```
          1235                1240                1245

Leu Ile Ser Tyr Ile Gly Ile Asp Phe Gln Ala Lys Gly Glu Arg
    1250                1255                1260

Val Tyr Arg Leu Leu Asp Cys Glu Leu Thr Phe Leu Glu Glu Met
    1265                1270                1275

Ala Phe Gly Gly Asp Thr Leu Arg Tyr Glu Ile His Ile Asp Ser
    1280                1285                1290

Tyr Ala Arg Asn Gly Glu Gln Leu Leu Phe Phe His Tyr Asp
    1295                1300                1305

Cys Tyr Val Gly Asp Lys Lys Val Leu Ile Met Arg Asn Gly Cys
    1310                1315                1320

Ala Gly Phe Phe Thr Asp Glu Glu Leu Ser Asp Gly Lys Gly Val
    1325                1330                1335

Ile His Asn Asp Lys Asp Lys Ala Glu Phe Ser Asn Ala Val Lys
    1340                1345                1350

Ser Ser Phe Thr Pro Leu Leu Gln His Asn Arg Gly Gln Tyr Asp
    1355                1360                1365

Tyr Asn Asp Met Met Lys Leu Val Asn Gly Asp Val Ala Ser Cys
    1370                1375                1380

Phe Gly Pro Gln Tyr Asp Gln Gly Gly Arg Asn Pro Ser Leu Lys
    1385                1390                1395

Phe Ser Ser Glu Lys Phe Leu Met Ile Glu Arg Ile Thr Lys Ile
    1400                1405                1410

Asp Pro Thr Gly Gly His Trp Gly Leu Gly Leu Leu Glu Gly Gln
    1415                1420                1425

Lys Asp Leu Asp Pro Glu His Trp Tyr Phe Pro Cys His Phe Lys
    1430                1435                1440

Gly Asp Gln Val Met Ala Gly Ser Leu Met Ser Glu Gly Cys Gly
    1445                1450                1455

Gln Met Ala Met Phe Phe Met Leu Ser Leu Gly Met His Thr Asn
    1460                1465                1470

Val Asn Asn Ala Arg Phe Gln Pro Leu Pro Gly Glu Ser Gln Thr
    1475                1480                1485

Val Arg Cys Arg Gly Gln Val Leu Pro Gln Arg Asn Thr Leu Thr
    1490                1495                1500

Tyr Arg Met Glu Val Thr Ala Met Gly Met His Pro Gln Pro Phe
    1505                1510                1515

Met Lys Ala Asn Ile Asp Ile Leu Leu Asp Gly Lys Val Val Val
    1520                1525                1530

Asp Phe Lys Asn Leu Ser Val Met Ile Ser Glu Gln Asp Glu His
    1535                1540                1545

Ser Asp Tyr Pro Val Thr Leu Pro Ser Asn Val Ala Leu Lys Ala
    1550                1555                1560

Ile Thr Ala Pro Val Ala Ser Val Ala Pro Ala Ser Ser Pro Ala
    1565                1570                1575

Asn Ser Ala Asp Leu Asp Glu Arg Gly Val Glu Pro Phe Lys Phe
    1580                1585                1590

Pro Glu Arg Pro Leu Met Arg Val Glu Ser Asp Leu Ser Ala Pro
    1595                1600                1605

Lys Ser Lys Gly Val Thr Pro Ile Lys His Phe Glu Ala Pro Ala
    1610                1615                1620

Val Ala Gly His His Arg Val Pro Asn Gln Ala Pro Phe Thr Pro
    1625                1630                1635
```

-continued

```
Trp His Met Phe Glu Phe Ala Thr Gly Asn Ile Ser Asn Cys Phe
1640                1645                1650

Gly Pro Asp Phe Asp Val Tyr Glu Gly Arg Ile Pro Pro Arg Thr
1655                1660                1665

Pro Cys Gly Asp Leu Gln Val Val Thr Gln Val Val Glu Val Gln
1670                1675                1680

Gly Glu Arg Leu Asp Leu Lys Asn Pro Ser Ser Cys Val Ala Glu
1685                1690                1695

Tyr Tyr Val Pro Glu Asp Ala Trp Tyr Phe Thr Lys Asn Ser His
1700                1705                1710

Glu Asn Trp Met Pro Tyr Ser Leu Ile Met Glu Ile Ala Leu Gln
1715                1720                1725

Pro Asn Gly Phe Ile Ser Gly Tyr Met Gly Thr Thr Leu Lys Tyr
1730                1735                1740

Pro Glu Lys Asp Leu Phe Pro Arg Asn Leu Asp Gly Ser Gly Thr
1745                1750                1755

Leu Leu Lys Gln Ile Asp Leu Arg Gly Lys Thr Ile Val Asn Lys
1760                1765                1770

Ser Val Leu Val Ser Thr Ala Ile Ala Gly Gly Ala Ile Ile Gln
1775                1780                1785

Ser Phe Thr Phe Asp Met Ser Val Asp Gly Glu Leu Phe Tyr Thr
1790                1795                1800

Gly Lys Ala Val Phe Gly Tyr Phe Ser Gly Glu Ser Leu Thr Asn
1805                1810                1815

Gln Leu Gly Ile Asp Asn Gly Lys Thr Thr Asn Ala Trp Phe Val
1820                1825                1830

Asp Asn Asn Thr Pro Ala Ala Asn Ile Asp Val Phe Asp Leu Thr
1835                1840                1845

Asn Gln Ser Leu Ala Leu Tyr Lys Ala Pro Val Asp Lys Pro His
1850                1855                1860

Tyr Lys Leu Ala Gly Gly Gln Met Asn Phe Ile Asp Thr Val Ser
1865                1870                1875

Val Val Glu Gly Gly Gly Lys Ala Gly Val Ala Tyr Val Tyr Gly
1880                1885                1890

Glu Arg Thr Ile Asp Ala Asp Trp Phe Phe Arg Tyr His Phe
1895                1900                1905

His Gln Asp Pro Val Met Pro Gly Ser Leu Gly Val Glu Ala Ile
1910                1915                1920

Ile Glu Leu Met Gln Thr Tyr Ala Leu Lys Asn Asp Leu Gly Gly
1925                1930                1935

Lys Phe Ala Asn Pro Arg Phe Ile Ala Pro Met Thr Gln Val Asp
1940                1945                1950

Trp Lys Tyr Arg Gly Gln Ile Thr Pro Leu Asn Lys Gln Met Ser
1955                1960                1965

Leu Asp Val His Ile Thr Glu Ile Val Asn Asp Ala Gly Glu Val
1970                1975                1980

Arg Ile Val Gly Asp Ala Asn Leu Ser Lys Asp Gly Leu Arg Ile
1985                1990                1995

Tyr Glu Val Lys Asn Ile Val Leu Ser Ile Val Glu Ala
2000                2005                2010

<210> SEQ ID NO 24
<211> LENGTH: 6036
```

<212> TYPE: DNA
<213> ORGANISM: Moritella marina

<400> SEQUENCE: 24

```
atggaaaata ttgcagtagt aggtattgct aatttgttcc cgggctcaca agcaccggat        60
caattttggc agcaattgct tgaacaacaa gattgccgca gtaaggcgac cgctgttcaa       120
atgggcgttg atcctgctaa atataccgcc aacaaaggtg acacagataa attttactgt       180
gtgcacggcg gttacatcag tgatttcaat tttgatgctt caggttatca actcgataat       240
gattatttag ccggtttaga tgaccttaat caatgggggc tttatgttac gaaacaagcc       300
cttaccgatg cgggttattg ggcagtact  gcactagaaa actgtggtgt gattttaggt       360
aatttgtcat tcccaactaa atcatctaat cagctgttta tgcctttgta tcatcaagtt       420
gttgataatg ccttaaaggc ggtattacat cctgattttc aattaacgca ttacacggca       480
ccgaaaaaaa cacatgctga caatgcatta gtagcaggtt atccagctgc attgatcgcg       540
caagcggcgg gtcttggtgg ttcacatttt gcactggatg cggcttgtgc ttcatcttgt       600
tatagcgtta agttagcgtg tgattacctg catacgggta aagccaacat gatgcttgct       660
ggtgcggtat ctgcagcaga tcctatgttc gtaaatatgg gtttctcgat attccaagct       720
tacccagcta acaatgtaca tgccccgttt gaccaaaatt cacaaggtct atttgccggt       780
gaaggcgcgg gcatgatggt attgaaacgt caaagtgatg cagtacgtga tggtgatcat       840
atttacgcca ttattaaagg cggcgcatta tcgaatgacg gtaaaggcga gtttgtatta       900
agcccgaaca ccaagggcca agtattagta tatgaacgtg cttatgccga tgcagatgtt       960
gacccgagta cagttgacta tattgaatgt catgcaacgg gcacacctaa gggtgacaat      1020
gttgaattgc gttcgatgga aaccttttc  agtcgcgtaa ataacaaacc attactgggc      1080
tcggttaaat ctaaccttgg tcatttgtta actgccgctg gtatgcctgg catgaccaaa      1140
gctatgttag cgctaggtaa aggtcttatt cctgcaacga ttaacttaaa gcaaccactg      1200
caatctaaaa acgttactt  tactggcgag caaatgccaa cgacgactgt gtcttggcca      1260
acaactccgg gtgccaaggc agataaaccg cgtaccgcag gtgtgagcgt atttggtttt      1320
ggtggcagca acgcccattt ggtattacaa cagccaacgc aaacactcga gactaatttt      1380
agtgttgcta aaccacgtga gcctttggct attattggta tggacagcca ttttggtagt      1440
gccagtaatt tagcgcagtt caaaaccctta ttaataata atcaaaatac cttccgtgaa      1500
ttaccagaac aacgctggaa aggcatggaa gtaacgcta  acgtcatgca gtcgttacaa      1560
ttacgcaaag cgcctaaagg cagttacgtt gaacagctag atattgattt cttgcgtttt      1620
aaagtaccgc ctaatgaaaa agattgcttg atcccgcaac agttaatgat gatgcaagtg      1680
gcagacaatg ctgcgaaaga cggaggtcta gttgaaggtc gtaatgttgc ggtattagta      1740
gcgatgggca tggaactgga attacatcag tatcgtggtc gcgttaatct aaccacccaa      1800
attgaagaca gcttattaca gcaaggtatt aacctgactg ttgagcaacg tgaagaactg      1860
accaatattg ctaaagacgg tgttgcctcg gctgcacagc taaatcagta tacgagtttc      1920
attggtaata ttatggcgtc acgtatttcg gcgttatggg attttctgg  tcctgctatt      1980
accgtatcgg ctgaagaaaa ctctgtttat cgttgtgttg aattagctga aaatctatt       2040
caaaccagtg atgttgaagc cgttattatt gctgctgttg atttgtctgg ttcaattgaa      2100
aacattactt tacgtcagca ctacggtcca gttaatgaaa agggatctgt aagtgaatgt      2160
ggtccggtta atgaaagcag ttcagtaacc aacaatattc ttgatcagca acaatggctg      2220
```

```
gtgggtgaag gcgcagcggc tattgtcgtt aaaccgtcat cgcaagtcac tgctgaccaa    2280
gtttatgcgc gtattgatgc ggtgagtttt gcccctggta gcaatgcgaa agcaattacg    2340
attgcagcgg ataaagcatt aacacttgct ggtatcagtg ctgctgatgt agctagtgtt    2400
gaagcacatg caagtggttt tagtgccgaa aataatgctg aaaaaaccgc gttaccgact    2460
ttatacccaa gcgcaagtat cagttcggtg aaagccaata ttggtcatac gtttaatgcc    2520
tcgggtatgg cgagtattat taaaacggcg ctgctgttag atcagaatac gagtcaagat    2580
cagaaaagca acatattgc  tattaacggt ctaggtcgtg ataacagctg cgcgcatctt    2640
atcttatcga gttcagcgca agcgcatcaa gttgcaccag cgcctgtatc tggtatggcc    2700
aagcaacgcc cacagttagt taaaaccatc aaactcggtg gtcagttaat tagcaacgcg    2760
attgttaaca gtgcgagttc atctttacac gctattaaag cgcagtttgc cggtaagcac    2820
ttaaacaaag ttaaccagcc agtgatgatg gataacctga agccccaagg tattagcgct    2880
catgcaacca atgagtatgt ggtgactgga gctgctaaca ctcaagcttc taacattcaa    2940
gcatctcatg ttcaagcgtc aagtcatgca caagagatag caccaaacca agttcaaaat    3000
atgcaagcta cagcagccgc tgtaagttca cccctttctc aacatcaaca cacagcgcag    3060
cccgtagcgg caccgagcgt tgttggagtg actgtgaaac ataaagcaag taaccaaatt    3120
catcagcaag cgtctacgca taaagcattt ttagaaagtc gtttagctgc acagaaaaac    3180
ctatcgcaac ttgttgaatt gcaaaccaag ctgtcaatcc aaactggtag tgacaataca    3240
tctaacaata ctgcgtcaac aagcaataca gtgctaacaa atcctgtatc agcaacgcca    3300
ttaacacttg tgtctaatgc gcctgtagta gcgacaaacc taaccagtac agaagcaaaa    3360
gcgcaagcag ctgctacaca agctggtttt cagataaaag gacctgttgg ttacaactat    3420
ccaccgctgc agttaattga acgttataat aaaccagaaa acgtgattta cgatcaagct    3480
gatttggttg aattcgctga aggtgatatt ggtaaggtat ttggtgctga atacaatatt    3540
attgatggct attcgcgtcg tgtacgtctg ccaacctcag attacttgtt agtaacacgt    3600
gttactgaac ttgatgccaa ggtgcatgaa tacaagaaat catacatgtg tactgaatat    3660
gatgtgcctg ttgatgcacc gttcttaatt gatggtcaga tcccttggtc tgttgccgtc    3720
gaatcaggcc agtgtgattt gatgttgatt tcatatatcg gtattgattt ccaagcgaaa    3780
ggcgaacgtg tttaccgttt acttgattgt gaattaactt tccttgaaga gatggctttt    3840
ggtggcgata ctttacgtta cgagatccac attgattcgt atgcacgtaa cggcgagcaa    3900
ttattattct tcttccatta cgattgttac gtaggggata agaaggtact tatcatgcgt    3960
aatggttgtg ctggtttctt tactgacgaa gaactttctg atggtaaagg cgttattcat    4020
aacgacaaag acaaagctga gtttagcaat gctgttaaat catcattcac gccgttatta    4080
caacataacc gtggtcaata cgattataac gacatgatga agttggttaa tggtgatgtt    4140
gccagttgtt ttggtccgca atatgatcaa ggtggccgta atccatcatt gaaattctcg    4200
tctgagaagt tcttgatgat tgaacgtatt accaagatag acccaaccgg tggtcattgg    4260
ggactaggcc tgttagaagg tcagaaagat ttagaccctg agcattggta tttcccttgt    4320
cactttaaag gtgatcaagt aatggctggt tcgttgatgt cggaaggttg tggccaaatg    4380
gcgatgttct tcatgctgtc tcttggtatg cataccaatg tgaacaacgc tcgtttccaa    4440
ccactaccag gtgaatcaca aacggtacgt tgtcgtgggc aagtactgcc acagcgcaat    4500
accttaactt accgtatgga agttactgcg atgggtatgc atccacagcc attcatgaaa    4560
gctaatattg atattttgct tgacggtaaa gtggttgttg atttcaaaaa cttgagcgtg    4620
```

```
atgatcagcg aacaagatga gcattcagat taccctgtaa cactgccgag taatgtggcg    4680
cttaaagcga ttactgcacc tgttgcgtca gtagcaccag catcttcacc cgctaacagc    4740
gcggatctag acgaacgtgg tgttgaaccg tttaagtttc ctgaacgtcc gttaatgcgt    4800
gttgagtcag acttgtctgc accgaaaagc aaaggtgtga caccgattaa gcattttgaa    4860
gcgcctgctg ttgctggtca tcatagagtg cctaaccaag caccgtttac accttggcat    4920
atgtttgagt ttgcgacggg taatatttct aactgtttcg gtcctgattt tgatgtttat    4980
gaaggtcgta ttccacctcg tacaccttgt ggcgatttac aagttgttac tcaggttgta    5040
gaagtgcagg gcgaacgtct tgatcttaaa aatccatcaa gctgtgtagc tgaatactat    5100
gtaccggaag acgcttggta ctttactaaa acagccatg aaaactggat gccttattca    5160
ttaatcatgg aaattgcatt gcaaccaaat ggctttattt ctggttacat gggcacgacg    5220
cttaaatacc ctgaaaaaga tctgttcttc cgtaaccttg atggtagcgg cacgttatta    5280
aagcagattg atttacgcgg caagaccatt gtgaataaat cagtcttggt tagtacggct    5340
attgctggtg gcgcgattat tcaaagtttc acgtttgata tgtctgtaga tggcgagcta    5400
ttttatactg gtaaagctgt atttggttac tttagtggtg aatcactgac taaccaactg    5460
ggcattgata acggtaaaac gactaatgcg tggtttgttg ataacaatac ccccgcagcg    5520
aatattgatg tgtttgattt aactaatcag tcattggctc tgtataaagc gcctgtggat    5580
aaaccgcatt ataaattggc tggtggtcag atgaacttta tcgatacagt gtcagtggtt    5640
gaaggcggtg gtaaagcggg cgtggcttat gtttatggcg aacgtacgat tgatgctgat    5700
gattggttct tccgttatca cttccaccaa gatccggtga tgccaggttc attaggtgtt    5760
gaagctatta ttgagttgat gcagacctat gcgcttaaaa atgatttggg tggcaagttt    5820
gctaacccac gtttcattgc gccgatgacg caagttgatt ggaaataccg tgggcaaatt    5880
acgccgctga ataaacagat gtcactggac gtgcatatca ctgagatcgt gaatgacgct    5940
ggtgaagtgc gaatcgttgg tgatgcgaat ctgtctaaag atggtctgcg tatttatgaa    6000
gttaaaaaca tcgtttttaag tattgttgaa gcgtaa                             6036
```

<210> SEQ ID NO 25
<211> LENGTH: 538
<212> TYPE: PRT
<213> ORGANISM: Moritella marina

<400> SEQUENCE: 25

```
Met Ser Ser Leu Gly Phe Asn Asn Asn Ala Ile Asn Trp Ala Trp
1               5                   10                  15

Lys Val Asp Pro Ala Ser Val His Thr Gln Asp Ala Glu Ile Lys Ala
            20                  25                  30

Ala Leu Met Asp Leu Thr Lys Pro Leu Tyr Val Ala Asn Asn Ser Gly
        35                  40                  45

Val Thr Gly Ile Ala Asn His Thr Ser Val Ala Gly Ala Ile Ser Asn
    50                  55                  60

Asn Ile Asp Val Asp Val Leu Ala Phe Ala Gln Lys Leu Asn Pro Glu
65                  70                  75                  80

Asp Leu Gly Asp Asp Ala Tyr Lys Lys Gln His Gly Val Lys Tyr Ala
                85                  90                  95

Tyr His Gly Gly Ala Met Ala Asn Gly Ile Ala Ser Val Glu Leu Val
            100                 105                 110

Val Ala Leu Gly Lys Ala Gly Leu Leu Cys Ser Phe Gly Ala Ala Gly
```

```
                115                 120                 125
Leu Val Pro Asp Ala Val Glu Asp Ala Ile Arg Arg Ile Gln Ala Glu
    130                 135                 140

Leu Pro Asn Gly Pro Tyr Ala Val Asn Leu Ile His Ala Pro Ala Glu
145                 150                 155                 160

Glu Ala Leu Glu Arg Gly Ala Val Glu Arg Phe Leu Lys Leu Gly Val
                165                 170                 175

Lys Thr Val Glu Ala Ser Ala Tyr Leu Gly Leu Thr Glu His Ile Val
            180                 185                 190

Trp Tyr Arg Ala Ala Gly Leu Thr Lys Asn Ala Asp Gly Ser Val Asn
        195                 200                 205

Ile Gly Asn Lys Val Ile Ala Lys Val Ser Arg Thr Glu Val Gly Arg
    210                 215                 220

Arg Phe Met Glu Pro Ala Pro Gln Lys Leu Leu Asp Lys Leu Leu Glu
225                 230                 235                 240

Gln Asn Lys Ile Thr Pro Glu Gln Ala Ala Leu Ala Leu Leu Val Pro
                245                 250                 255

Met Ala Asp Asp Ile Thr Gly Glu Ala Asp Ser Gly Gly His Thr Asp
            260                 265                 270

Asn Arg Pro Phe Leu Thr Leu Leu Pro Thr Ile Ile Gly Leu Arg Asp
        275                 280                 285

Glu Val Gln Ala Lys Tyr Asn Phe Ser Pro Ala Leu Arg Val Gly Ala
    290                 295                 300

Gly Gly Gly Ile Gly Thr Pro Glu Ala Ala Leu Ala Ala Phe Asn Met
305                 310                 315                 320

Gly Ala Ala Tyr Ile Val Leu Gly Ser Val Asn Gln Ala Cys Val Glu
                325                 330                 335

Ala Gly Ala Ser Glu Tyr Thr Arg Lys Leu Leu Ser Thr Val Glu Met
            340                 345                 350

Ala Asp Val Thr Met Ala Pro Ala Ala Asp Met Phe Glu Met Gly Val
        355                 360                 365

Lys Leu Gln Val Leu Lys Arg Gly Ser Met Phe Ala Met Arg Ala Lys
    370                 375                 380

Lys Leu Tyr Asp Leu Tyr Val Ala Tyr Asp Ser Ile Glu Asp Ile Pro
385                 390                 395                 400

Ala Ala Glu Arg Glu Lys Ile Glu Lys Gln Ile Phe Arg Ala Asn Leu
                405                 410                 415

Asp Glu Ile Trp Asp Gly Thr Ile Ala Phe Phe Thr Glu Arg Asp Pro
            420                 425                 430

Glu Met Leu Ala Arg Ala Thr Ser Ser Pro Lys Arg Lys Met Ala Leu
        435                 440                 445

Ile Phe Arg Trp Tyr Leu Gly Leu Ser Ser Arg Trp Ser Asn Thr Gly
    450                 455                 460

Glu Lys Gly Arg Glu Met Asp Tyr Gln Ile Trp Ala Gly Pro Ser Leu
465                 470                 475                 480

Gly Ala Phe Asn Ser Trp Val Lys Gly Ser Tyr Leu Glu Asp Tyr Thr
                485                 490                 495

Arg Arg Gly Ala Val Asp Val Ala Leu His Met Leu Lys Gly Ala Ala
            500                 505                 510

Tyr Leu Gln Arg Val Asn Gln Leu Lys Leu Gln Gly Val Ser Leu Ser
        515                 520                 525

Thr Glu Leu Ala Ser Tyr Arg Thr Ser Asp
    530                 535
```

<210> SEQ ID NO 26
<211> LENGTH: 1617
<212> TYPE: DNA
<213> ORGANISM: Moritella marina

<400> SEQUENCE: 26

| | | | | | |
|---|---|---|---|---|---|
| atgtcgagtt | taggttttaa | caataacaac | gcaattaact | gggcttggaa | agtagatcca | 60 |
| gcgtcagttc | atacacaaga | tgcagaaatt | aaagcagctt | taatggatct | aactaaacct | 120 |
| ctctatgtgg | cgaataattc | aggcgtaact | ggtatagcta | atcatacgtc | agtagcaggt | 180 |
| gcgatcagca | ataacatcga | tgttgatgta | ttggcgtttg | cgcaaaagtt | aaacccagaa | 240 |
| gatctgggtg | atgatgctta | caagaaacag | cacggcgtta | aatatgctta | tcatggcggt | 300 |
| gcgatggcaa | atggtattgc | ctcggttgaa | ttggttgttg | cgttaggtaa | agcagggctg | 360 |
| ttatgttcat | ttggtgctgc | aggtctagtg | cctgatgcgg | ttgaagatgc | aattcgtcgt | 420 |
| attcaagctg | aattaccaaa | tggcccttat | gcggttaact | tgatccatgc | accagcagaa | 480 |
| gaagcattag | agcgtggcgc | ggttgaacgt | ttcctaaaac | ttggcgtcaa | gacggtagag | 540 |
| gcttcagctt | accttggttt | aactgaacac | attgtttggt | atcgtgctgc | tggtctaact | 600 |
| aaaaacgcag | atggcagtgt | taatatcggt | aacaaggtta | tcgctaaagt | atcgcgtacc | 660 |
| gaagttggtc | gccgctttat | ggaacctgca | ccgcaaaaat | tactggataa | gttattagaa | 720 |
| caaaataaga | tcacccctga | caagctgct | ttagcgttgc | ttgtacctat | ggctgatgat | 780 |
| attactgggg | aagcggattc | tggtggtcat | acagataacc | gtccgttttt | aacattatta | 840 |
| ccgacgatta | ttggtctgcg | tgatgaagtg | caagcgaagt | ataacttctc | tcctgcatta | 900 |
| cgtgttggtg | ctggtggtgg | tatcggaacg | cctgaagcag | cactcgctgc | atttaacatg | 960 |
| ggcgcggctt | atatcgttct | gggttctgtg | aatcaggcgt | gtgttgaagc | gggtgcatct | 1020 |
| gaatatactc | gtaaactgtt | atcgacagtt | gaaatggctg | atgtgactat | ggcacctgct | 1080 |
| gcagatatgt | ttgaaatggg | tgtgaagctg | caagtattaa | aacgcggttc | tatgttcgcg | 1140 |
| atgcgtgcga | agaaactgta | tgacttgtat | gtggcttatg | actcgattga | agatatccca | 1200 |
| gctgctgaac | gtgagaagat | tgaaaaacaa | atcttccgtg | caaacctaga | cgagatttgg | 1260 |
| gatggcacta | tcgcttttctt | tactgaacgc | gatccagaaa | tgctagcccg | tgcaacgagt | 1320 |
| agtcctaaac | gtaaaatggc | acttatcttc | cgttggtatc | ttggcctttc | ttcacgctgg | 1380 |
| tcaaacacag | gcgagaaggg | acgtgaaatg | gattatcaga | tttgggcagg | cccaagttta | 1440 |
| ggtgcattca | acagctgggt | gaaaggttct | taccttgaag | actatacccg | ccgtggcgct | 1500 |
| gtagatgttg | ctttgcatat | gcttaaaggt | gctgcgtatt | tacaacgtgt | aaaccagttg | 1560 |
| aaattgcaag | gtgttagctt | aagtacagaa | ttggcaagtt | atcgtacgag | tgattaa | 1617 |

<210> SEQ ID NO 27
<211> LENGTH: 35
<212> TYPE: DNA
<213> ORGANISM: Artificial
<220> FEATURE:
<223> OTHER INFORMATION: Primer

<400> SEQUENCE: 27
ttcgagctcg catatggtac agcttaaaac ctatg        35

<210> SEQ ID NO 28
<211> LENGTH: 7959
<212> TYPE: DNA

<213> ORGANISM: Moritella marina

<400> SEQUENCE: 28

```
atggctaaga agaacactac tagtattaag cacgctaagg atgtcctttc aagtgatgac      60
caacaactca acagcagatt gcaagagtgc cctattgcta ttatcggtat ggctagtgtg     120
ttcgctgatg ctaagaacct agatcaattc tgggataaca ttgttgattc agtggatgct     180
attatcgacg ttccttcaga taggtggaat atcgacgatc actactctgc cgacaagaag     240
gccgctgata agacatactg caaacgtggt ggattcattc cagaattgga tttcgaccca     300
atggaatttg gacttccacc taacattctg gagcttacta tattgctca actactgtcc      360
ctcattgttg ctagggatgt tctctccgat gccggaatag ttctgattca gatcacgac      420
aagattggaa ttacccttgg agttggcggt ggtcagaagc aaatttcacc cttgacttct     480
aggctgcaag gaccggtgct tgagaaggtg ttgaaggcat ctggaattga tgaggatgat     540
agagcaatga taatcgacaa attcaagaag gcttacatag ggtgggagga aatagtttc      600
cctgggatgc taggaaacgt gattgccggt agaattgcca ataggttcga tttcggcgga     660
actaactgcg tcgttgatgc tgcgtgcgct ggtagtcttg ctgctgttaa gatggcaatt     720
tcagatttgc tggagtatcg ttcagaagta atgatctccg gtggagtttg ttgcgataat     780
agtcccttca tgtacatgag tttctcgaag actcccgcat tcacaactaa cgacgatatt     840
aggccattcg atgatgacag caaaggaatg ctcgtgggag aagggattgg aatgatggct     900
ttcaaacgac tggaggatgc tgaaagggat ggtgataaga tatactccgt gctgaaagga     960
attggtacta gctcagatgg cagattcaag tctatatatg cacctaggcc agatggccaa    1020
gctaaggctc ttaagagggc atacgaagac gccggattcg ctcctgagac ctgcgggtta    1080
atagagggcc acggaactgg cacgaaggct ggagacgctg ctgaatttgc tggcctaaca    1140
aagcactttg cgcagcgtc cgatgagaag cagtacatcg cactcgggtc agtcaagtcc     1200
caaattggcc atacaaagtc tgccgctggg tcagctggaa tgattaaggc tgcactcgcg    1260
cttcatcaca agatcctccc ggcgaccata cacattgata agccttctga ggcgctcgat    1320
attaagaaca gtcccttata cctgaatagt gaaactagac cgtggatgcc aagggaagac    1380
gggattccga cacgtgctgg gattagctct ttcggatttg gcgggacaaa ctttcacata    1440
atcctcgaag agtaccgtcc tgggcatgat tctgcctacc gtcttaatag tgtttctcag    1500
actgttctta tttctgctaa cgatcagcaa ggaattgttg ccgagcttaa caattggaga    1560
actaaactcg ctgttgatgc tgaccaccaa ggattcgtat tcaacgaact tgttaccaca    1620
tggcctctga agactccttc agtcaatcag gcccgcttag gtttcgttgc tagaaacgcc    1680
aacgaggcga ttgctatgat agacactgcg cttaagcagt ttaacgctaa cgctgataag    1740
atgacctgga gtgtgccaac aggagtctac tatcgtcagg ccggaattga cgcaactggg    1800
aaggtggttg ctctgttcag tggtcaaggg tcacagtatg tcaacatggg tcgtgaactg    1860
acctgtaact tcccatctat gatgcactca gcagccgcaa tggataagga gtttagtgct    1920
gccggactgg gtcaactttc tgctgtcacg tttcctatcc cagtatatac cgacgctgag    1980
agaaagctac aagaagagca gctcagactc acccaacatg cacaacctgc cattggatct    2040
ctgtctgtcg gtttgtttaa gacctttaaa caggctggtt tcaaagccga tttcgccgct    2100
ggtcattcct ttggcgagct taccgcccta tgggctgctg atgttctttc tgagtctgat    2160
tacatgatgt tggctagatc cagaggtcaa gcaatggcag cacctgagca acaggacttt    2220
gatgccggga agatggctgc ggtggttgga gacccaaagc aagtggcggt tattatcgac    2280
```

```
acattggacg atgtttccat tgcaaacttt aacagtaaca atcaagtagt aatcgctggc    2340
actaccgaac aagtggcagt tgctgtcacc actttgggaa acgctgggtt taaagttgtc    2400
cctctgccag tttcagccgc attccacact ccactggtcc gccacgcaca gaaaccattc    2460
gccaaagctg tcgattctgc taagtttaag gctcctagta tccctgtgtt tgctaacggt    2520
actggtttgg tgcacagtag caagccaaat gacatcaaga agaacctgaa gaaccacatg    2580
ctagagtccg ttcactttaa ccaggagatt gataacatct acgctgatgg agggagggtg    2640
ttcattgaat ttggcccgaa gaatgtcctt acaaagctgg tggagaatat cctcactgag    2700
aaatctgacg tgaccgccat tgctgtgaac gctaacccaa agcaaccagc cgatgtgcaa    2760
atgagacagg cagctctgca aatggctgtg ttgggtgtgg ctcttgataa catcgaccct    2820
tacgatgccg tgaaacggcc cttggttgct ccaaaggcaa gccctatgtt gatgaagctg    2880
agtgccgctt cttatgtcag ccctaagact aagaaggcgt tcgccgatgc tctgaccgat    2940
gggtggactg ttaagcaagc taaagctgtt cctgctgttg taagccaacc acaagtcatt    3000
gagaagatag ttgaggtcga gaagatcgtg gagcgtatcg tggaagttga acggattgtc    3060
gaagtcgaga agattgtcta cgtgaacgca gatggtagtc taattagtca gaataaccag    3120
gatgttaata gtgccgttgt gagtaatgtt acaaatagtt cagttacaca tagttcggat    3180
gctgacttgg tagcatctat cgagaggtca gtgggccagt tgttgcaca ccagcaacag    3240 ctcttaaatg tccatgagca gtttatgcaa ggacctcagg actacgctaa gaccgttcag    3300
aatgtactcg cagctcaaac aagtaacgag ttgccagagt cgcttgatag aactctgtct    3360
atgtacaatg aatttcaaag cgaaactctt agggtgcatg agacatactt gaataaccag    3420
acatcgaata tgaacactat gcttacggga gcagaagctg atgtgctcgc aacgccaatc    3480
acacaagtcg tgaacactgc tgttgctacc agtcataagg tcgtggcccc agttatcgca    3540
aacactgtga ctaacgttgt cagttcagtg agtaataacg ccgctgttgc ggtgcaaacc    3600
gttgcacttg ctcctactca agagatagcg ccaaccgtgg ccacaactcc ggctcctgca    3660
ttggttgcca tagttgctga acccgtgatt gttgcccatg ttgcaaccga agtggctcct    3720
attcacccca gcgtcacacc tgtcgttgca acccaggctg ctattgatgt ggctactatt    3780
aacaaggtca tgcttgaggt tgtggccgat aagactggct atcctactga catgcttgag    3840
ttatctatgg acatggaggc tgatctcggt attgatagca taaaagagt ggaaattctc    3900 ggtgctgtac aagaactcat ccctgatctg cctgagctta tccagaaga ccttgctgag    3960 ttgagaaccc taggtgagat cgtggactac atgaactcca agcacaagc cgttgcacca    4020 accacagttc ccgtgacttc ggcacccgtg agcccagcgt ctgccggaat cgacctcgcg    4080
cacatccaga acgtgatgct agaggttgtg gctgataaga cagggtatcc gacagatatg    4140
ctggaattgt ctatggatat ggaagctgat ttgggaatcg acagtattaa gcagtggag    4200 atattgggag cagttcagga gattatcacg gatctccctg agttgaatcc agaagacctt    4260
gctgagttga ggacgttggg agaaatcgtt agctatatgc aatctaaggc accagttgct    4320
gaatcagcac ccgttgccac tgcacccgtt gccacctcat ccgcaccatc tattgatttg    4380
aatcacattc aaactgtcat gatggatgtt gtggccgaca agacaggata ccctactgac    4440
atgcttgagc ttggaatgga tatggaagca gaccttggaa tagactccat aaaacgagtt    4500
gagatattgg gagctgtcca ggaaatcatt actgacctta ccgagttgaa cccagaggat    4560
ctcgccgaac tcagaaccct tggcgaaata gtttcttata tgcaatcgaa ggctcctgtc    4620
```

```
gctgagtccg caccagttgc aacagcgtcc gtggcaacct catccgcgcc ctcgatcgat    4680
ctcaatcaca tacaaactgt gatgatggag gtggttgctg ataagaccgg ttatcccgtg    4740
gacatgcttg agttggcaat ggatatggag gccgacctcg gaatcgactc tattaagagg    4800
gtggaaattc ttggcgcagt tcaggaaatt ataacagact acccgaact caacccagag    4860 gacttggccg agttgcggac tcttggtgag atcgtttcct acatgcaatc taaggcacca    4920
gtcgccgaag ctccagcagt cccagttgcc gtagagtcgg ctccaacctc tgttaccagc    4980
tctgctccta gtatcgactt agaccacatt cagaatgtta tgatggatgt tgttgctgat    5040
aagaccggtt accctgccaa tatgctggaa ttggctatgg atatggaggc agacttgggg    5100
atcgactcta taaaagagt ggagatactc ggtgctgtgc aagaaattat aactgacctt    5160
ccagaactca accctgagga ccttgccgaa ttacgcaccc tcgaagagat cgtcacttac    5220
atgcaatcca aagcaagtgg agttactgtt aatgtcgtag catctccaga gaacaatgcc    5280
gtgtcagatg ctttcatgca atctaatgtc gccaccatca ctgccgccgc agaacacaag    5340
gccgagttca aacctgcgcc tagtgccact gttgccatct cacgactatc tagcataagc    5400
aagattagcc aagattgcaa aggtgctaac gctctgattg tggcagacgg tactgacaac    5460
gctgtactcc ttgctgacca cttactgcaa acaggctgga atgttacggc ccttcaaccc    5520
acatgggtcg ctgtaactac cactaaagcc tttaacaaat ctgtaaacct tgttaccctc    5580
aatggtgtgg atgagactga aattaataac attataactg caaacgcaca actcgacgct    5640
gtcatatact acatgcttc ctctgagatt aacgccatcg aatatccgca agcctctaaa    5700
cagggtctta tgcttgcatt ccttctcgcc aaattatcca agtaactca ggcagctaaa    5760 gtgagaggtg ccttcatgat cgtgactcag caaggtggta gcttgggctt cgatgatatt    5820
gactcggcca cgtcgcatga tgttaagaca gatttggttc agtctggcct caatggactc    5880
gtcaagactc taagccatga atgggataac gtattctgtc gcgcagttga cattgcctct    5940
tcgctaactg ccgagcaagt ggcttcactt gtttccgacg agcttcttga tgccaacaca    6000
gtcttgaccg aagtgggata ccaacaggct gggaaaggat tggagaggat tacactcaca    6060
ggcgtagcaa ctgattcata cgcacttact gctgggaaca atatagatgc caatagcgta    6120
tttctagtgt ctggaggtgc taaaggagtg acagctcact gcgtagcccg aatcgcaaag    6180
gagtatcagt caaagtttat ccttctcggt agatcaacct tcagctcaga tgagccctct    6240
tgggccagcg ggattacgga tgaggccgca ttgaagaaag ccgcgatgca atctttgata    6300
accgctggag acaagcccac acctgttaag attgttcagc ttatcaagcc cattcaggcc    6360
aatagggaaa ttgcccaaac cctgagcgca attactgctg ctggaggtca ggctgagtat    6420
gtgagcgcag acgttaccaa tgctgcgtcc gtgcaaatgg cagtggctcc agctatcgcc    6480
aaattcggtg caatcacggg tattatacac ggtgcgggtg ttcttgccga tcagtttatt    6540
gagcagaaga cactgtctga ctttgagtcc gtttattcca ccaagattga tggtttactt    6600
tccttgctgt cagtgactga ggcatctaat atcaaacaac tcgttttgtt tagctccgca    6660
gcgggcttct acgggaaccc tgggcagagc gattactcaa tagcaaatga gatccttaat    6720
aagacggcct atcgctttaa atccttacat ccacaggctc aagttctcag cttcaactgg    6780
ggtccttggg atgaggcat ggtcactccc gaattgaaac gcatgtttga ccagcgtggc    6840
gtttatatta tcccattgga tgctggcgct caattgctct tgaatgagtt agctgcaaat    6900
gataatcggg gtccacagat ccttgttggc aacgacctct caaggacgc cagttctgac    6960 cagaagtcag acgagaaatc taccgctgtt aagaagcctc aagtgagccg cttgtcagac    7020
```

| | |
|---|---|
| gcattagtga ccaaatctat caaagcaaca aatagctcct cattgtccaa caagacctca | 7080 |
| gctctctccg atagctctgc tttccaagtc aatgagaatc acttcttggc agatcacatg | 7140 |
| attaagggga atcaagttct accaaccgtc tgcgctatcg cctggatgtc cgacgccgct | 7200 |
| aaagctacct attccaatag ggactgtgct ctgaaatatg ttggtttcga agactataag | 7260 |
| ttgtttaagg gtgttgtgtt tgatggaaat gaagcagcag attatcagat ccagctttca | 7320 |
| ccggttaccc gcgcctcaga acaggattcc gaagttcgca tcgctgcaaa gattttagt | 7380 |
| cttaaatctg acggaaagcc tgtctttcat tatgcggcta ccatccttct tgcaacacag | 7440 |
| cccttgaatg ccgttaaagt agaattgcca acacttaccg aaagcgttga ttcaaacaat | 7500 |
| aaggtcaccg atgaagctca agctctttat tcaaacggaa cactatttca tggcgaatca | 7560 |
| ctacaaggga tcaaacagat tctatcctgt gatgacaaag gtctcttact tgcctgtcag | 7620 |
| ataacgacg ttgccacagc caaacagggc tcctttccct tagctgataa taacatcttt | 7680 |
| gcgaatgatt tggtgtacca ggccatgctc gtctgggtga ggaaacagtt tgggctgggc | 7740 |
| tcacttcctt cagtcaccac agcttggacc gtatatcggg aagtagttgt cgatgaagtc | 7800 |
| ttctatttgc agttgaacgt tgtggaacat gatttgttag ggtcacgtgg ttcaaaggct | 7860 |
| cgttgtgaca ttcagttgat tgctgcggac atgcaactct tggcagaagt taaatctgca | 7920 |
| caagtttccg tgtccgacat cctcaatgac atgagttga | 7959 |

<210> SEQ ID NO 29
<211> LENGTH: 2652
<212> TYPE: DNA
<213> ORGANISM: Moritella marina

<400> SEQUENCE: 29

| | |
|---|---|
| atgacagagt tggcagtgat tggtatggat gctaaattca gtggtcaaga taacattgat | 60 |
| agagttgaga gagcttttcta cgagggtgct tacgttggaa acgtgagtag agtgagtacc | 120 |
| gagtctaacg tgatttctaa cggtgaggag caagtaatca ctgctatgac cgttctaaat | 180 |
| agtgttagtc tcctagctca gaccaatcag ttgaacatcg cagacatcgc agtccttctc | 240 |
| atagctgacg tcaagtccgc cgatgaccaa cttgtggtcc agatcgctag tgcaattgag | 300 |
| aaacagtgtg ctagttgtgt tgttatcgcg gaccttggtc aagccctcaa tcaagttgcc | 360 |
| gaccttgtga caatcagga ttgcccagta gctgttattg gtatgaacaa tagtgttaat | 420 |
| ttgtccaggc acgacctgga gtcagttact gctactattt cattcgacga aacttttcaac | 480 |
| ggatacaata acgtcgccgg gttcgctagt ttgcttattg cctccaccgc ctttgccaac | 540 |
| gcaaagcaat gctacatcta tgctaacatt aagggattcg cacaatcggg agtgaacgca | 600 |
| cagtttaacg tggggaacat tagtgatact gcaaagactg cactgcaaca ggcgtcaatt | 660 |
| accgctgaac aagtgggctt gctcgaagtc tctgccgtgg cggatagtgc tattgccctc | 720 |
| tcagagagcc aagggcttat gagtgcttac catcacaccc agactctcca cactgcacta | 780 |
| tcatctgcac gcagcgtgac aggagaaggt gggtgcttca gccaagtagc tgggctcttg | 840 |
| aagtgcgtta tcggcttgca tcagcgttac attcctgcca ttaaggattg gcaacagcct | 900 |
| agcgataatc agatgagcag atggcgaaat agccctttct acatgccagt tgacgctagg | 960 |
| ccctggttcc cgcacgcaga tggtagcgcc cacatcgctg cctattcatg tgtgactgcc | 1020 |
| gactcctact gccacatcct tcttcaagag aatgtgttgc aagagttggt gcttaaggag | 1080 |
| acagttctgc aagacaatga tttgaccgag agcaagttac aaactttgga acagaacaat | 1140 |

-continued

```
cctgttgccg atttgagaac aaatggatac tttgcttcct ctgagttggc tctcattatc    1200
gttcagggca acgatgaagc acaacttagg tgcgagttag aaacaatcac cggccaattg    1260
tctacaactg gcattagcac aatttctatc aaacagatcg ccgcagactg ttatgcacgg    1320
aatgatacca acaaagcata tagtgcagtc ttgattgctg aaacagcaga ggaactttct    1380
aaggagatta ccttagcgtt tgcgggtatt gcatctgtct taacgagga cgctaaagaa    1440 tggaagacac caaagggaag ctatttcact gctcagccag cgaacaagca agctgcaaac    1500
tcaacacaga atggtgtcac gttcatgtac cctggaatcg gtgccactta cgttggcctg    1560
ggtcgtgatc tctttcatct gtttccgcag atatatcaac ccgtagctgc ccttgctgat    1620
gacataggtg aatctctcaa ggataccctc cttaatccac gctctatctc gcgtcattca    1680
ttcaaggaac ttaaacagct tgacctcgat ctacgcggca atctggccaa catcgctgag    1740
gctggagtgg gatttgcatg tgtgttcact aaagtgtttg aggaagtatt tgcggttaaa    1800
gccgacttcg ctactggata ctctatggga gaggtttcca tgtacgctgc actgggatgt    1860
tggcagcaac ccggcttaat gtcagctaga ctggctcaat ccaatacgtt taatcaccaa    1920
ttgtgtggtg agcttcgcac cttaaggcag cactggggta tggatgatgt tgccaatggc    1980
accttcgaac aaatctggga acatacacc attaaggcta ctattgaaca agttgaaata    2040
gcttctgccg atgaggacag ggtttattgc acgatcatta acacaccaga ctcgctctta    2100
cttgctggtt atcctgaggc gtgccagagg gtcattaaga atcttggagt gcgtgctatg    2160
gccttgaaca tggctaacgc cattcattct gctcctgctt atgccgaata cgaccacatg    2220
gttgaactat atcacatgga tgtgacacca cgtattaaca cgaagatgta ctcttcatcc    2280
tgctatctcc ctatccctca gagatccaag gctatctccc attctattgc aaagtgcttg    2340
tgtgatgtcg ttgatttccc tcggcttgtt aatacctgc atgataaggg agcacgagtg    2400
tttattgaaa tgggacccgg aaggtcgctg tgttcttggg ttgataagat actcgttaat    2460
ggtgatggtg ataacaagaa acagtcacag catgtctccg tccctgtgaa cgcaaagggt    2520
acatcagacg aactgaccta cataagagcc atagcaaagc tcataagtca tggtgtaaat    2580
ttgaaccttg attctctctt caatggatct attcttgtca aagccgggca tatcgcaaat    2640
accaacaaat ga                                                        2652
```

<210> SEQ ID NO 30
<211> LENGTH: 6036
<212> TYPE: DNA
<213> ORGANISM: Moritella marina

<400> SEQUENCE: 30

```
atggagaaca ttgctgttgt gggaattgct aacttgttcc ctggtagtca agctcctgac     60
cagttctggc aacagttgtt ggagcaacaa gattgccgta gtaaggctac tgctgttcaa    120
atgggtgtgg atcctgctaa gtacactgct aacaaaggtg atactgataa gttctactgc    180
gttcacggag gttacattag tgactttaac ttcgatgcaa gtggttacca gttggataac    240
gattacctcg ctggtcttga tgatcttaat cagtggggat tgtacgttac aaagcaagct    300
cttaccgacg cgggttactg gggtagtacg gcattagaga actgtggtgt catacttggc    360
aatctctcat tcccaactaa atcctcaaac cagctattca tgcccttgta ccaccaagta    420
gttgacaatg ctctcaaggc tgttctccat ccagactttc agcttaccca ttacaccgcg    480
cctaagaaga ctcacgccga taacgctttg tggctggat accctgctgc cttgattgca    540
caggccgctg gtctcggagg ttctcacttt gcccttgatg ctgcatgtgc tagtagctgc    600
```

```
tattctgtaa agttggcctg tgattacttg catactggga aagctaacat gatgcttgct      660
ggagctgttt cagccgcaga ccctatgttt gtgaatatgg gtttctccat ctttcaagcc      720
tatccagcta acaatgttca tgctcccttc gaccagaact ctcaaggtct gtttgccgga      780
gaaggagctg gcatgatggt tcttaaacgc cagagcgatg ctgtcagaga tggcgatcac      840
atctacgcta ttatcaaggg aggcgcactg tcaaacgatg aaagggtga gtttgtcttg      900 agtcctaaca caaagggtca agtccttgtc tacgaaagag cgtatgctga tgctgatgtc      960
gatccctcta ctgttgacta cattgaatgt cacgccacag ggacacctaa gggagataac     1020
gttgagttac gttctatgga gaccttcttt agccgtgtta ataacaagcc acttctagga     1080
agcgttaaat ctaacctcgg acatctcttg acagccgccg gtatgcctgg catgaccaaa     1140
gcaatgttgg cgttagggaa gggcctaatc ccagccacta ttaaccttaa gcagccactt     1200
cagtcaaaga acggttactt tactggagag caaatgccaa ctactactgt ctcttggccg     1260
accacaccgg gtgcaaaggc tgacaagcca aggacggcgg gagtcagtgt gtttggcttc     1320
ggtggatcaa acgctcactt ggtcttgcaa cagccgactc agactctgga aacaaatttc     1380
agcgtggcca aacccaggga gcctttggct attattggca tggactccca ctttggatct     1440
gcatctaacc tggcgcagtt taagacgctc cttaataaca atcagaatac tttcagagag     1500
cttcccgagc agaggtggaa gggaatggaa agcaatgcta acgtgatgca atccttacaa     1560
ttgaggaagg ctccaaaggg tagttatgtt gaacagttgg acatcgactt cttgaggttc     1620
aaggtgcctc caaatgagaa ggactgtctg atccctcaac agttgatgat gatgcaagtt     1680
gccgacaatg ccgccaaaga cggagggctc gtcgagggca gaaacgtggc tgtacttgtc     1740
gcaatgggca tggaattgga acttcatcag taccgtggac gcgtaaacct tacaactcag     1800
atagaggata gtcttctaca acaggggatc aatttgactg tggagcagag agaagagttg     1860
accaacatcg ctaaggatgg agttgcctca gccgctcaac tcaaccagta cacctctttc     1920
ataggcaaca ttatggctag tcgcattagt gccctctggg atttcagtgg ccctgccatt     1980
accgtctccg ctgaggagaa ctccgtttat cgttgcgtcg agcttgctga gaatctcttt     2040
caaacaagcg atgttgaggc agttatcata gcagccgtgg accttagtgg ctccatcgag     2100
aacattaccc tccgacagca ctacgggcct gtgaacgaga agggatctgt ttcagagtgt     2160
ggacctgtta atgaatcgtc ttcagttacc aataacattc tcgatcaaca gcaatggctt     2220
gttgagagag gagccgcagc tatcgtcgtg aagcctagtt cacaagtgac agcagaacaa     2280
gtgtacgcga gaatcgacgc agtgagtttc gctcccggta gcaacgctaa ggcaataact     2340
atcgccgcag ataaggcttt gaccttagcc gggatctcag cagcagatgt cgccagcgtc     2400
gaggcacatg ctagtggttt cagtgccgag aacaatgctg agaagacagc tctcccgacc     2460 ctttacccctt cggctagtat ttcctcagtt aaagccaaca tagggcacac cttcaacgcc     2520
tcagggatgg ctagtatcat taagaccgct cttctccttg accagaatac ttctcaggac     2580
cagaaatcca agcacatcgc tatcaacgga cttggtaggg ataatagctg tgcccacctc     2640
atactttctt cgtctgctca agcacaccaa gtggctcctg ctccagtgag cgggatggcc     2700
aaacaaagac cacagctagt gaagactatt aagctgggag gtcaactaat ctccaatgcc     2760
atcgttaatt ccgccagctc cagtctgcac gctattaagg cccagttcgc tgggaaacat     2820
ctgaataagg tgaaccagcc tgttatgatg gacaacctga aacctcaagg gatctctgca     2880
catgcaacta acgagtatgt ggtcactgga gctgctaaca ctcaagctag taacatacaa     2940
```

```
gcctcacacg tccaggctag ttctcacgca caggagattg caccaaatca agtgcagaac    3000
atgcaagcta ccgctgctgc agtaagctcg ccattgtcac agcaccaaca cacagctcaa    3060
cctgtggccg caccatcagt tgtcggtgtg actgtcaagc acaaggcaag caatcagatt    3120
catcaacagg catcaaccca caaggcattc ctggaatcac gtcttgcggc ccagaagaat    3180
ctgtctcagt tggttgagtt acaaactaag ttgtccattc aaaccggctc tgataatacg    3240
tccaataaca ctgcttctac ctctaacacc gttcttacta atcctgtttc ggccactccc    3300
ttgaccttgg tttctaacgc tcctgttgtg gcgaccaacc ttactagcac cgaagctaag    3360
gcacaggcca cagccacaca agcgggtttc cagatcaaag ccctgtcgg gtacaactat    3420 ccacctctgc aattgattga agatacaat aagcccgaga atgtgatata cgatcaagcg    3480
gatttggtgg agttcgcgga aggtgacatt gggaaggtct ttggtgctga gtacaacatt    3540
attgatggat actctcgcag agttagactg ccaacctctg attatctgct tgttaccagg    3600
gttaccgagt tggatgcaaa ggtgcatgag tacaagaaat cttatatgtg taccgaatac    3660
gacgtacccg tggacgcacc attcttgata gacggacaga tcccttggtc agtagccgtg    3720
gaatctggtc aatgcgatct tatgttaatc tcctacattg gaatcgactt tcaagccaag    3780
ggtgaacgcg tttatcgtct tctcgattgc gagctaacct ttctcgaaga gatggcattc    3840
ggcggtgata cacttagata cgagatccac attgatagct atgcaaggaa tggcgaacag    3900
ttgttattct tctttcatta cgattgttat gtgggcgaca agaaggtgtt gattatgagg    3960
aacgggtgcg ctggtttctt tactgatgag gaactctctg acgggaaagg cgttatccat    4020
aatgacaaag ataaggctga gtttagcaac gctgtgaaat ctagctttac acccttgctt    4080
cagcataaca gaggacagta cgattacaat gacatgatga agttagttaa tggcgatgtt    4140
gcaagttgct ttgggccgca gtatgaccaa ggagggcgca atcctagctt gaagttcagc    4200
tctgagaaat tccttatgat agaaagaatc accaagattg atccaacggg aggccattgg    4260
ggtctgggtc ttctggaggg acagaaagac ctcgatccgg aacattggta tttcccttgt    4320
cactttaaag gagaccaagt catggctggg tccttgatga gcgaaggctg cggtcagatg    4380
gcaatgttct tcatgctctc tctcggtatg cacaccaatg tgaacaatgc tagatttcaa    4440
ccactgcccg gcgaatccca aacagtccgg tgccgtggtc aagtgctccc tcagcgaaat    4500
actctgacgt atcgtatgga ggttactgca atggggatgc accctcaacc attcatgaag    4560
gcaaacatag acatcctctt ggatggcaaa gtggtagtag atttcaagaa tctttcagtt    4620
atgatttcag aacaagatga acactctgat tatccggtca ctctcccatc taatgtggca    4680
ttgaaagcca tcaccgcgcc agttgcctcc gtggcaccag cctcaagtcc ggccaatagc    4740
gcggatcttg atgagagagg agtggaaccc tttaaattcc cagagcgccc tctgatgagg    4800
gttgaatcag acctatctgc tcccaaatcc aagggcgtta ctcccatcaa gcacttcgag    4860
gctcctgccg ttgccgggca tcataggggtt ccaaaccagg caccccttcac tccttggcat    4920 atgtttgagt tcgctactgg gaacattagt aattgctttg gtccagattt cgacgtttat    4980
gaaggtcgca tacctccacg aacaccatgc ggcgacttac aagttgtgac tcaagtggtt    5040
gaagttcagg gagaaaggct tgatcttaag aatccatcct catgtgttgc tgaatactat    5100
gtacccgagg atgcttggta tttcacaaag aatagtcacg agaattggat gccctattcg    5160
ctaattatgg aaatagcact gcaacccaat ggctttattt ctggttacat gggcactact    5220
ctcaaatacc ctgagaagga tctattcttt aggaatcttg atggctccgg aactttactt    5280
aaacagatcg acctcagagg gaagacaata gttaataagt ctgtactcgt ttctaccgca    5340
```

```
atcgctggtg gagctattat ccaatccttt acattcgaca tgagtgttga tggagaattg    5400
ttctacaccg ggaaagcagt gtttggctat ttctccggag aatctttgac taaccagcta    5460
gggattgaca atggcaagac gacaaacgct tggttcgtcg ataataacac acccgcagct    5520
aacattgacg tgtttgacct cacaaatcag tccctagcac tctacaaagc gccagttgat    5580
aagccacatt acaaattggc tggagggcag atgaacttta ttgatacggt ttctgttgtt    5640
gaaggaggcg gaaaggccgg tgttgcatac gtgtacggtg aaaggacaat tgatgctgac    5700
gattggttct ttcggtatca ctttcatcag gaccctgtca tgcccggatc gctgggtgtg    5760
gaagcaatta tcgagcttat gcaaacctat gctctgaaga acgatctcgg aggcaaattt    5820
gcaaatccac ggtttattgc accaatgacc caagttgatt ggaaataccg aggtcagatt    5880
acacccttga caaacagat gtcactcgat gttcacatta ctgaaatagt caatgatgcg    5940
ggtgaagtca ggattgtggg agacgcaaat ctctcaaagg acggacttag gatctatgaa    6000
gtaaagaaca tcgtgctctc catagttgag gcatga                              6036

<210> SEQ ID NO 31
<211> LENGTH: 1617
<212> TYPE: DNA
<213> ORGANISM: Moritella marina

<400> SEQUENCE: 31
atgagttctt tgggtttcaa caacaacaac gctattaact gggcttggaa ggttgatcct      60
gctagtgttc acactcaaga tgctgagatt aaggcagctt tgatggattt gactaagcct     120
ttgtacgttg ctaacaactc tggagtgact gggatcgcca atcataccag cgttgcggga     180
gccatctcaa ataacataga cgtggatgtt cttgctttcg cccagaaact gaatcctgag     240
gaccttggtg atgatgctta caagaaacaa catggcgtta aatacgccta tcatggaggc     300
gcaatggcaa acgtattgc aagtgttgaa ctggtcgtgg ccttaggaaa ggcgggtttg     360 cttttgttctt tcggagcggc cggactcgtg cctgatgccg tcgaagacgc gatcagacgt     420
atccaagctg agcttccaaa tgggccatac gcagtaaacc ttattcacgc accagccgag     480
gaagctcttg agagggcgc tgtcgagagg tttcttaagt tgggtgtcaa gaccgtagag     540
gctagtgcct acctcggtct caccgaacac attgtttggt atcgagccgc tggactcacc     600
aagaacgccg acggtagtgt taacattggc aataaggtca ttgctaaagt ttcgaggacg     660
gaagttggga ggcgcttcat ggaaccagct ccacagaagt tgctcgataa gttgcttgag     720
cagaataaga tcacacccga acaagccgca ttggctctct tagtgcctat ggcagatgac     780
attactggtg aggctgattc aggaggccat actgataatc gcccttttcct cacacttctt     840 ccaacaatca tagggctccg cgacgaagtt caagctaagt acaactttag ccctgcccta     900
agagtgggtg ctggaggtgg aatagggacg ccagaagcag ccctggccgc attcaacatg     960
ggagctgcct acattgtgct cggcagcgtg aatcaggctt gcgtcgaggc tggagcctct    1020
gagtacacaa gaaagctgtt gtccaccgta gaaatggctg atgtcacaat ggctcccgct    1080
gccgatatgt ttgagatggg agttaaatta caagtgctta acgcgggtc tatgtttgct    1140 atgagggcta agaaactata tgacttgtac gttgcatacg atagcatcga agacataccg    1200
gcagcggaga gggagaagat agagaaacag attttcaggg caaacctgga tgagatttgg    1260
gatggcacta tcgctttctt tactgagcgt gatcccgaaa tgttggcacg tgccacctcg    1320
tctccgaagc gtaagatggc gcttatccttt agatggtatc taggtctctc atccagatgg    1380
```

```
tctaataccg gagagaaggg acgggaaatg gactatcaga tttgggccgg gccttcattg    1440
ggagcattca atagctgggt taaagggtca tacttagaag actacactag acgaggcgca    1500
gtggacgtgg cacttcacat gctgaaaggt gctgcttatt tgcaacgggt taatcagttg    1560
aaactgcaag gcgtgtcact ttccacagaa ctcgcatcct atcgtacctc cgactga      1617

<210> SEQ ID NO 32
<211> LENGTH: 48
<212> TYPE: DNA
<213> ORGANISM: Artificial
<220> FEATURE:
<223> OTHER INFORMATION: Primer

<400> SEQUENCE: 32
agctgcggcc gcatttaaat ggcgcgcccg tacgggccgg ccaagctt                 48

<210> SEQ ID NO 33
<211> LENGTH: 48
<212> TYPE: DNA
<213> ORGANISM: Artificial
<220> FEATURE:
<223> OTHER INFORMATION: Primer

<400> SEQUENCE: 33
ggccaagctt ggccggcccg tacgggcgcg ccatttaaat gcggccgc                 48

<210> SEQ ID NO 34
<211> LENGTH: 864
<212> TYPE: DNA
<213> ORGANISM: Moritella marina

<400> SEQUENCE: 34
atgtacagcg gcgttaagga caagctcacc ctcaccacaa acgagatcca cctctggagc    60
gtgacacctc agaccatcca gcagcccgag ctgctccagg cctactccca gctcctgtct    120
ccagccgaga ccatcaagca gcagaggttc cgcttcgaga aggaccgcca caacgccctc    180
atcacccgcg ccttcgtgcg cgacctcctg tcccactacg ccgacgtcct cccagccgac    240
tggcagttcg tcaagggaga gaaggacaag cctgagatcg ccaaccctcc actccctctg    300
aggttcaaca tctcccacac cgacaacctg attatttgcg ctgtcatgct gaacgacgac    360
atcgggtgcg atgtcgagaa cacactgagg tcctctaacg ttctttccat cgctaagcac    420
tctttctcag attcagagtt caacgatctt cttacacagc ctacagctca gcagacttca    480
agattcttcg attactggac tcttaaggaa agctatatca aggcatgggg attgggtttg    540
tcaataccat tgaaagattt cagtttcacc cttcccgaag gtttccaaca gcagtatcaa    600
caagaggatc aacaagagaa tcaacattgc atagatacta taaagttgtc ctttgctcct    660
catagaattg ataatccaaa tatttggcgt cattggttgt tttatccaaa caatactcat    720
cgtgtggcac tcgctgttag agcaaggtcc aacaatcaac aaaccgaata taaaatgcgc    780
ttctttaata gtactcctct catcaatata accgaaaccc ttatcttcaa gcccgaaaca    840
aattttaaac ccgatgctaa atga                                          864

<210> SEQ ID NO 35
<211> LENGTH: 748
<212> TYPE: DNA
<213> ORGANISM: Brassica napus

<400> SEQUENCE: 35
ctgatacaca cttaagcatc atgtggaaag ccaaagacaa ttggagcgag actcagggtc    60
```

-continued

```
gtcataatac caatcaaaga cgtaaaacca gacgcaacct ctttggttga atgtaatgaa      120
agggatgtgt cttggtatgt atgtacgaat aacaaaagag aagatggaat tagtagtaga      180
aatatttggg agcttttaa gcccttcaag tgtgcttttt atcttattga tatcatccat       240
ttgcgttgtt taatgcgtct ctagatatgt tcctatatct ttctcagtgt ctgataagtg      300
aaatgtgaga aaaccatacc aaaccaaaat attcaaatct tatttttaat aatgttgaat      360
cactcggagt tgccaccttc tgtgccaatt gtgctgaatc tatcacacta gaaaaaaaca      420
tttcttcaag gtaatgactt gtggactatg ttctgaattc tcattaagtt tttattttct      480
gaagtttaag tttttacctt ctgttttgaa atatatcgtt cataagatgt cacgccagga      540
catgagctac acatcgcaca tagcatgcag atcaggacga tttgtcactc acttcaaaca      600
cctaagagct ctctctctcac agcgcacaca catatgcatg caatatttac acgtgatcgc     660
catgcaaatc tccattctca cctataaatt agagcctcgg cttcactctt tactcaaacc      720
aaaactcatc actacagaac atacacaa                                          748

<210> SEQ ID NO 36
<211> LENGTH: 313
<212> TYPE: DNA
<213> ORGANISM: Brassica napus

<400> SEQUENCE: 36
gagtgtgtat accacggtga tatgagtgtg gttgttgatg tatgttaaca ctacatagtc      60
atggtgtgtg ttccataaat aatgtactaa tgtaataaga actactccgt agacggtaat      120
aaaagagaag ttttttttt tactcttgct actttcctat aaagtgatga ttaacaacag       180
atacaccaaa aagaaaacaa ttaatctata ttcacaatga agcagtacta gtctattgaa      240
catgtcagat tttctttttc taaatgtcta attaagcctt caaggctagt gatgataaaa      300
gatcatccaa tgg                                                          313

<210> SEQ ID NO 37
<211> LENGTH: 7596
<212> TYPE: DNA
<213> ORGANISM: Shewanella oneidensis

<400> SEQUENCE: 37
atgagccata cccttcaca gcctcaacct tcaaccgata aaaagccga taaaaggcta        60 aataaacgct tgaaagatat gcccattgcc atcgttggta tggcgagtat ctttgcaaac      120
tcacgctatt taaataagtt ttgggattta atttgcgaca agattgatgc cattaccgac      180
gtgccagcca gccattgggc gattgatgac tattacgacg tggataaatc caaggccgat      240
aaaagttact gcaagcgcgg tggctttatg ccagaggtcg acttcaatcc tatggagttt      300
ggtctgccgc caatatttt ggaactcacc gacagctcac aattgctttc cctcgtcgta      360
gccaaagaag tgctgcagga tgccaatctg ccagacgatt acgaccgtga ccgcatcggt      420 atcaccctttg ggattggcgg cgggcaaaag ctaagccata gcctcaacgc gcgcctgcaa      480
tatcctgtgc ttaaaaaagt atttaaaagc agtggcctga gcgatgaaga tagcgagctg      540
ctgatcaaaa aattccaaga ccaatatgtc cactgggaag aaaactcctt ccccggctcc      600
cttggcaacg tgattgccgg acgcatcgcc aaccgtttcg atttaggtgg aatgaactgc      660
gtcgtcgatg ccgcctgcgc aggatcgctt gccgccatgc gtatggcgct caccgaactg      720
accgaaggtc gcagcgacat gatgatcacc ggcggtgtct gtaccgacaa ctcgcccttac      780
```

```
atgtatatga gtttctcaaa gacacccgcc tttaccacca acgagcaaat ccaacccttc   840
gatatcgact ctaagggcat gatgattggc gaaggcatcg gcatggtcgc cttaaaacgc   900
ctcgacgatg ccgagcgcga tggcgaccgt atttatgcgg taatcaaagg cgtaggcgcc   960
tcatcggacg gtaaatttaa gagcatttat gcgccgcgcc ccgaaggcca agccaaggca  1020
ctagagcgcg cctatgatga cgcgggcttt gcgccgcaca ctgttggctt gattgaggcc  1080
cacggcacag gcacagccgc aggcgatgta gcggaattta ctggtttaag ctcagtgttt  1140
tctcaggata acgcgcagtt acagcatatc gccttaggct cagtcaaatc tcaggtgggc  1200
cacactaaat ccaccgcggg cacggcgggt gtgattaagg ccgcgctggc actgcaccat  1260
aaagtattgc cacccacgat taacgtcagc aagcccaatc ctaagcttga gattgatcgc  1320
tcgccctttt atctcaatac cgaggcgcgc ccttggatcc aacgcagtga tgatacgccg  1380
cgccgcgctg ggataagctc cttcggtttt ggtggcacaa acttccattt agtactcgaa  1440
gaataccgcc cagatcacac gcgcgatgac gcctatcgtc aacgcagcgt ggcacaaatc  1500
ctactgtttg cggctaacga taaaaccttg ctactgaacg agttaaaagc tgttttacaa  1560
caagcaagct cagctaaggc ggagcttttct gaggcgcatt ttattcagtt tgctaaaccc  1620
tacgccctgc gagaaattac gccgcaatcg gcccgtcttg gctttatcgc caaagactat  1680
gcccagttac agactctgtt aacccaagcg atagcgcagc ttgaagccaa taacgctgag  1740
agctggcaat taccttctgg gatcagctac cgcgccaagg ccttagtcaa tgagcaaacc  1800
aagatcgccg cgctatttgc tggtcaaggc gcgcagtacc tgaatatggg actggagctt  1860
gccaataact tccccgagct tcgccgccat atccacgcca gcgataaagt gtttagtacc  1920
catggtaagc ctgcgctttc aagcgtgctc tatcctattc cagcctttga tgatgagtcg  1980
ataaaagcgc aggaaacggc attaaccaac actctgtatg cccaaagcgc catcggcgcg  2040
ctctcaatgg cgcagtacgc cctgtttact caggcaggtt tcgccccaga tatgctggct  2100
ggtcatagct tcggtgagct ttcggccctg tgcgccgcag gggttatctc aatggatgac  2160
tacatcaaac ttgccttttga gcgtggacag gcgatggcgc agtcatccca agataccgat  2220
gcgggtgtta tgtatgcagt gatccttaag caaaaacaag atattgaggt aatcaacggt  2280
tgccttgcgc agtttgaagg cgtcaaagtt gccaactaca actcacccac tcagctggtg  2340
attgcaggcg ctagtgccgc cacccaacag gcggctaagg ccattagcga gttaggcttt  2400
aaggcgattg ccctgcccgt ttctggcgcc tttcacacgc cattggttgc ccatgcacaa  2460
aagccctta gtgcagccat cgataaggct cagttcaaca cgccaaagat tgccttatat  2520
gccaatggca caggccagct gcatcctatc gatgccaacg ccatcaaagc tgccttgaaa  2580
gatcatatgt tgcaatcggt gcactttagc gagcagctag aagccatgta gccgcaggc  2640
gcacgggtgt tgtcgagtt cggcccaaaa acattctgc aaaagttaac tgaaaatacc  2700
ctcgcggcgc agttaaacga gctgtgtatt atcagcatta accctaatcc caagggcgat  2760
agtgacagcc aactgcgcag cgccgcagtg caactggcgg tggcgggggt aaaactccgc  2820
gagattgatc cgtatcaagc agagttaatt gccccagcag caacatcggc catgaatata  2880
aaactcaatg ccaccaacta catcagccca gcgacccgca gcaaaatggt cgattcgctg  2940
caatcggca aaattaccag ccaagtgcag tatgtggatc gcatcgttga aaagtggtt  3000
gagaaagttg ttgaaaaacc agtgattgtc gaaaaaattc tagaaaaggt tgtcgaagtg  3060
gaaaagcccg tggcacaaaa tagcaataat attcaacagc aaacgcctgc acagccagcc  3120
agctttaccg ctggacagac gaatcaagat gccctgagcg ccttttttgc cgcccaaacc  3180
```

```
caggcagcgc aattacatca acaattttg gccattccgc agcaatacgg cgatacagtc   3240
agcgcactga tggcagagca agccaaaatg gcaagccttg ggatcgctat tccagagagc   3300
ctacaacgct caatggaact gttccatcag caccaagcgc aaaccctaaa aagtcatagt   3360
gactttatgc aattgcaaac cagcagtagc caagcagtac tggcattatt aggtcaaatg   3420
ccagcgtctc aggttcaagc ccccattcaa gccgctgcac cagtggcagt agcagtgaca   3480
aaacctgtcg ttccagcaca ggcccccgtg gttcaagggt tggccgcaga gcctaaagtg   3540
actgctgtgc ctgtgagcga gcccacagtt cagcaacctc aagtagcact ggcacaagta   3600
gcacagacaa aagtaactca gccaccatta gcgcaaccac aagtacaaac tgtggccgca   3660
caaaccagtg cgcttcaagt aaagcctgcc ttgcagcaaa tcgagcacgc tatgctctca   3720
gtggtggcag acaagaccgg ctatccggtt gaaatgttag aacttagcat ggatatggaa   3780
gcggacttag ggatcgactc cattaagcgc gtagaaattc taggcacagt gcaggatgaa   3840
ttaccgaacc tgccagaact cagcccagaa gatttagccg agtgccgcac cctagggaa    3900
attgtggcgc tatttagcca agcagctcct gtaacatctg cgaccactgt tagccatgct   3960
acacaaagtg ccgtagccgc aagcgcggcg gtttccaatg atgagattga gcgcactatg   4020
atggcggtcg tggccgacaa gactggctat cccgttgaaa tgctggaact cagcatggat   4080
atggaagccg accttggcat tgactccatt aagcgcgtgg aaattctagg cacagtgcag   4140
gacgaattac ccaacctgcc agaactgagc ccagaagatt tagccgagtg ccgtacccta   4200
ggggaaattg tggcgctatt tagccaagcc gtcccagtgg cagcacaaac ctttgcagcc   4260
atggcagcaa cgaatcctca ggttgtcgcc tctgccgtca cgccaattgc ggccgtatcc   4320
gatggcgaga ttgagcacac tatgatggcg gttgtggccg ataaaaccgg ttatcccgtt   4380
gaaatgctgg aactcagcat ggacatggaa gccgaccttg gaattgactc cattaaacgg   4440
gtggagattt taggcacggt gcaagataag ctgccaaatc tgccggaact cagcccagaa   4500
gatttagccg agtgccgaac cttagggaa attgcggcgc tctttagcca agcggctcct   4560
gtaacagctg cggccacagt tagccatgcg acacaaagtg caatagctgc aagggcggcg   4620
gtttctaatg atgaaattga gcgcactatg atggcggttg tggccgataa aaccggttat   4680
cccgttgaaa tgcttgagct aagcatggac atggaagccg accttggtat cgattccatt   4740
aagcgcgtgg aaattctagg cacagtacaa gaccaactgc caaacttgcc agaactcagc   4800
ccagaagatt tagccgagtg tcgtaccttg ggtgaaattg tcgccctcta tgctggttcg   4860
caatcatcaa gtgaggcgct acaacaaaac catgctgcga caattcaaga gactcaagag   4920
gctattgcaa aaaccgtcga ggaaaccatc gacctgccgc cccatagtga ggtgatgcta   4980
aaaaagttgc cagcggcggc tgagttagcg cgcatcatcg caactagcga tgttcaactg   5040
acggcaaaca gttacgtcgt tatcggcgac gatggccaca acgcgggggt gattgccgaa   5100
aagcttcacg cccaaggtgt taaggtcgcg gttgtacgct cacctaaaac ggttgtgacc   5160
agcgcatcgc cactcgatag ccatattgcc agcttcacgc tggaggctat tgatgatgaa   5220
agcatttgtg aggtcatcaa tcagattgaa gcgcttggcc aaatcgccgg tttattcat    5280
ctgcagccac agcataaatc cgttgccgat aaaggtgctg gcttagtgct ggtagatgaa   5340
gccaaagctt cggtcgagca agccttcttg ttcgccaaat tcttacaacc gcttttaact   5400
gaacgtgact attgccgctt tgtcaccgtc agctgtatag acggtggctt tggctatatc   5460
ggcatggacg agtcggtagg tgccctcatc agccagagtg aactcaaacca agcggcgctc   5520
```

-continued

```
tttggactca ctaaaacctt aaatcacgag tggccgggag tggtctgccg cgcgctggat      5580
atcgcgccaa acttggacgc taaaacggtc gccaatgcgg tggtgcagga atactacctt      5640
caagatgcgc cggtcgaagt cggtattgat agcaactttg atcgcgtgac attagttgca      5700
ggcaccgctg cacttcgcca tccacccgcc gtccttagca atgcagataa aatactggtc      5760
acgggcggtg ctaaaggtgt cactttgaa tgcgccttaa gcttagcaaa acgctgtcag       5820
gcacattttt tcctcgctgg ccgtagcgcc caccaagtga tccctgcatg gcagaggga      5880 aaaaagagca acgaactcaa agccgcagcc attgcgcacc tgcaaagcct tggtgataaa      5940
cccacaccaa acaagtgga cgccttagta tggcccgtgc agagcagcct tgagatcagc      6000
catgctttag ccgcctttga tgccattggc gccagcgctg agtacttaag tgtggatgtc      6060
aacgaccctg cggccattgc cagcaccatt gcgcccatta acgcactatc gcctatcact      6120
gggattattc acggtgcggg agttctagcc gataaacata ttcaagacaa gaccttaaat      6180
gaatttgaac gtgtctatgg tactaaggtc accgggctta ataatctgct gtcaacgctg      6240
gatcttagcc aagtaaaact gattgcactg ttctcttcgg cggcgggttt ttacggcaat      6300
accggccaga gcgactacgc catgtctaac gacattctca ataaagccgc gctgcaactt      6360
gcgcagcaat taccacaagc caaggtgatg agcttcgact ggggtccttg ggatggcggc      6420
atggtcaatc cagcgctgaa aaaaatgttt attgaccgcg gggtttatgt cattccactc      6480
aaagcgggtg ccgagttatt tgccagccaa ttattgagtg atacaggcgc acagctgttg      6540
gtcggaaccg atatgcaggg caataccgcc aatgccgttg aagttgcatc agcaaaaaag      6600
cctgaagcgg atctagccac agcgttagat ccgcagccta tggcccaaac ggtgccgcag      6660
agcattcgcg tcatgcgcag cctcgaccct aaacgcatga gctttattga ggatcattgc      6720
atcaatggtc atgcggtgtt gccaacggta tgcgccatcg attggatgcg tgaggccgcc      6780
aaggcccatt taggtacggc ggtgagtgtc agcgattatc gactgctcaa gggagtaatc      6840
ttcgatgagg cgctgcttgc acgcaatgcg cctattgagc tcgaattgat gctcacgccg      6900
cttgctgacg ctgcacaaca atcgactgag gcgttagccg cgctgataag ctttgaaggt      6960
cgcccgcagt atcaggcggt gttagtggcg cagacggatg atatgccaga cgcgcagcgt      7020
ttcgaggttg gcgagttgca ttctctgata caggagatgg cacagcaacc cgctatcgcg      7080
aaccgcgagt cgctctacag cgatggcacc ttgttccatg gcccgagact gcaaggcata      7140
agcgaagtgc tcacctttga tgaccaacat cttatggcca agtagaact gccacaggtg      7200 gccttagacg actgcggcaa gtttgcgcca aagcttgagg ataagggtac acaacccttt      7260
gccgaagatc tgttattgca ggccatgctc gtgtgggctc gccttaaata tcaagcggca      7320
agcttaccca gcacgattgg cgagtttgtt tcctatgcgc ccttgagctt tggtgaaaag      7380
gcagtattag tgctggatgt gcttaagcac tcgtcccgct cgcttgaggc gaatattgcc      7440
ctctaccatc aggatggccg tttaagctgc gagatgaaac gagcaaaagt cacgatcagt      7500
aagacgctta accaagcatt tttggctaat aaacctcaac aactggcgca agtgcaggca      7560
tcaatccaaa acatggccga ggtaagtgtt aagtga                                7596
```

<210> SEQ ID NO 38
<211> LENGTH: 2205
<212> TYPE: DNA
<213> ORGANISM: Shewanella oneidensis

<400> SEQUENCE: 38

```
atggcttgtc gcattcagct caatgttgaa gataagctac tgattgatga gccatctgat      60
```

```
gagccatctg atgagtcaac cttagtcgcc ttactcagcg agcagctcgc ccatattgcg    120
caaaaacaac tcgttgaaat ccgctttgaa tatcaacagc aagttcgtag tctgtttctg    180
ctcgatggac tacttgccgc gcaattacac ctgcatgccg aggcttatat ttcagccttg    240
gcacagactc aagccgaagc gaatgaagca ctctgcgata tagaaatcga aaactgtaca    300
aatcgcgctt tgccctcgc caaacgcgat tgtgctcagg cggttaattg ctactcggat     360
gcaggcaatc ttgccagtca gctaaagctt ttatatcaag ctattgaggc gttaagtcat    420
cgaacgctag caggtattac gccaatgctt gcccacctca atacagaaaa acagagcga    480 tgttattggt tctccaagcc ccatcaagca agggtgttaa gcctaaatct cttcgataaa    540
gcccctcaag ctcagacagc ccaaagcctt atcttgactc aaggtacagg gcttatcgct    600
caaccgttgc tcaatgccaa caggctgttt attcccatca gcggcaatga gtttgagtcg    660
ttaacgctta agttgttgca actgattgat tcattgacct tatcgttaaa ccaacctgat    720
acggattggc tcagcagcca aggcagtgat tggtttaagc gctatcaagc aaaggatgaa    780
ttagccttag tgctgatggc aggctcccctt gaagagttaa tgcaagaagc caaagcgatg    840 cagacttta ttgaaaaggc acgactgact attgagtcca gcgcatccaa gcacagtgca     900
tccaagccta gtgcatcgac aagtttggta tttaaaaccc cagcgggcag ttattttgcg    960
gcctcgcccc ttggtgataa gggcttaacc ttcgtctatc ccggcgtagg cactgtttac   1020
ccgaatatgt tcagcgactt acatagctat ttccctgagc tttatcgcga gcttgaacgc   1080 gaagggatt tagccgccat gttgcaggcc gagacgattt accaagacgc ggcttatgcg   1140
aaaaccgcag ttaatgtaag cgtaaaagac accgcagaaa tgagcttaag ccagctcgcc   1200
attagcggcg ttggtgcgag ttaccttttt agcaagttat tgactggcgt ctttactatc   1260
caaccacggc tcgcactggg ctattccatg ggtgaagcag ccatgtgggc aagtttagct   1320
atctggcaaa caccccacag cctgattgat gccacccaag gcagcgcaat tttcaaccac   1380
gaaatctccg gtaaacttca agccgttcgc cgcgactggc aattgaatga agatgctccg   1440
ctggcgtgga atagcttttt agtgcgcgca accagtaccg aaattaatcc actgctggct   1500
gattttccgc gggtttatct ggccatcgaa cagggcgata cctgtattct cgcgggctgc   1560
gaagcaagct gcttacagct ccttgcaagg ctgaataagc gtggcattgc cagcaataaa   1620
gtgacggcca tgcatactgc gccttcgcag tcacagcgca atgcaatcca agggttttat   1680
accttaggct taaaggccac agcctgcgag actcaggttc gttttattag cgcggcgcag   1740
catagccccg tcaatattga tagcatgagt attgccaaaa gcattgccga tacctttgc    1800 gcgccgctga atttaccgc gctgattaac accgcgtata accaaggtgc gcgcttattt    1860
gttgaggtgg gcgccgatcg tcaaaccagc acccttatcg ataaaatcag ccgccaactt   1920
gagttgggcg ccgatggtgt tcaagaaccg atattagcca tggcatgcaa tgccaagggc   1980
agcgatacga tcgtcagttt gctcaaatgc ttagctcaac ttatcagcca tagagtgcca   2040 ctctcccctgg cggcacttat gcctcaatcg gcagctcaat cagcaacgca ctcagcaact   2100
atccatgcgg ataagactgc ggctaaaacg atagcgtcac actctgccaa cgcctgcgca   2160
ttaggccatt attcaaacgt attccaagaa ggagaacccc tttga                   2205
```

<210> SEQ ID NO 39
<211> LENGTH: 5892
<212> TYPE: DNA
<213> ORGANISM: Shewanella oneidensis

```
<400> SEQUENCE: 39
atgagttctc aaatgcatac tcacccgact ctgcaagaca gcgccgctgt gccaaacgac      60
cagcgccaaa cgttaaaggc gatgccaaag attgccattg tcggccttgc tgtccagtat     120
cccgatgccg acacaccgga gcagttttgg caaaatctgc tggataaaaa agattcccgc     180
agccaaatcg acgcggccaa actcaatgcc aatcctgctg attaccaagg gattcaaggc     240
caagccgacc gttttttactg cgacaagggc ggctatatcc gcaactttcg ttttgatcca     300
cagggttatc agttactgcc agccactttt gcagggctgg atgaaagctt tttatgggca     360
ttagattgca gtaaaaaggc cctactgaat gcgggcgtgg atttaacggc gccattactt     420
gagcgcacag ggattgtgat gggcacgctc tccttcccga cggctcgctc caatgaatta     480
tttttaccga tttaccatca gcggttgaa aaggcattaa aaaccaagct taatcaacca     540
caatttgcct tagcgccctt cgccaatgct tcaattgcgg gctcgcaact ggcagccaat     600
ggtgtcattg ctcatacggc gtctaagttg ttaagcgatg ccctcggcct tggcggcgca     660
cagctcagtc tcgacgccgc ctgcgccagc tcagtctatg ccctcaaatt ggcctgcgat     720
tatttaacca cgggcaaggc cgatatgatg ctcgcgggcg ctgtatcggg cgccgatccc     780
ttctttatca atatgggatt ctcgattttc cacgcctatc cagaccatgg gatttcggcg     840
cctttcgata gcaatagcaa aggcttattc gcgggcgaag gcgctggcgt attagtgctt     900
aagcgtttag aggatgccga gcgcgatggc gataatatct atgctgtggt cagtggcatt     960
ggttatcgaa cgatggcaa aggccaattt gtcttaagcc caacagtaa gggccaagtg    1020
caagccttcg agcgcgccta tgccgccgct aacacgcacc cgagcaatat cgaagtgatt    1080
gaatgccatg ccaccggcac gccgctgggg gataaagttg agctcacttc gatggagcgt    1140
tttttcgagg ataaactcga cggcactaaa gcgccgctga taggttcggc caaatccaat    1200
cttgggcatt tgctcaccgc agccggcatg cctgggataa tgaagatgat ttttgccatg    1260
cgctcaggcc atctaccgcc aagtatcaat ttaacggcgc cgatttcatc acctaaaggg    1320
ttgtttagcg tcaataatct tcccacacag cgtcaggctt ggcccgataa agcgggcaac    1380
gatcgtcgcc atgcaggggt gtctgtattt ggttttggcg gctgtaacgc ccatctgttg    1440
ttggaatcct atcaaccgac agcgcacagc gccgagaagc aagccaacaa acctgtttat    1500
cagcagcaag cattaaccgt tataggcatg gcgtcgcatt ttgggccttt ggcctccatc    1560
aatgcgctgg ataaggcgct aatagcccaa acgatgcct ttatcccgct gccccctaaa    1620
cgatggaaag gcttagataa acaccccgat atcttgcagc aatttggcct aaatcgcgcg    1680
cccaaaggcg cctatatcga gcagtttgac ttcgactttt tgcgctttaa agtgccgccc    1740
aatgaggatg acaggcttat ctcccagcaa ttgttgctga tcaaagtcgc cgacgaagcg    1800
attcgcgatg ccaagttaac cgcaggcagc aaggtcgcgg tgttagtggc gatggaaacc    1860
gagcttgagc tgcaccaatt ccgtggccgg gtgaatttgc acacccaact ggcggatagc    1920
ttaaagaaac aaggtgttca cctctccaat gatgaatacc tcgccctcga agccatcgcc    1980
atggacagcg tgctcgatgc cgccaagctc aatcaataca ccagctttat tggcaatatt    2040
atggcgtcgc gcatcgcctc gctgtgggac tttaacggcc cagcgtttac catttcagcc    2100
gccgagcaat cggttgcccg ttgtatcgat gtggcgcaaa acttactgtc caaagaggcc    2160
ctagatggcg tagtgattgc cgccgtggat ttaagcggca gtgttgaaca ggtcatattg    2220
aaaaacgctc aagtcgccgt tgatctcgat gccaacagcg caaatccaca gtggaaggtg    2280
ggtgaaggcg ccggcgctat cgtgcttaca aaccagcaag cgagcaacag tcaacaagcg    2340
```

```
ggttacggcc aaattcgtgg tcaagcattt ggcacaaacc atcagctgcc taagctgctt      2400
gattcgctga taaccgaaac ggctatcgcc aatccttcaa tgccaacggc catccatatg      2460
attgagcaat gtattgcccc agaagaacaa ctgccagcag agcatttatt agcgcagctt      2520
aatcttttgg ggacgtcatg caatcgagtc gccaataccc ttggacataa ctttgccgct      2580
gcaggtatgg ccagtcttct gagtgccctg ttaagcctaa agaacaggtc agcaaattcg      2640
gataaaaacg ccgaaaaaca ggcattagtg tctacccaaa gccaaggggt gagctcgctg      2700
ctgctgttaa gccaaacggc aacgcaggcg gcacaactag aactgcgcct tgcgcaggac      2760
ttaaccttaa gtgagcaaaa acatttaatc aaaccagtga cgctcggtgg tcgcgatatc      2820
tatcaacata ttgtagatac gccgctgcct gcacttgccg ccatccaagg caaaatgcgc      2880
cagttgcagc ctttagcctc acaggcgaca caaactaagc ccgcagtggg cgcagcactt      2940
gatatcacgg ctgaaaacgc cacaccatta gcagcagaga gcggtatgtc atctaacgca      3000
ccacttcaat ttgagacaac agcatcggcg caggatagcg cggcattgtt gcaaaaccag      3060
caactcgccc gcgaggcgca cttagccttt ttacagagcc gtgagcaagg gctcaaactg      3120
gcagatgcgt tgttaaaggc acaattatcc cagacgacac aaatgggtgc tgttgcagcc      3180
catgttgcca ccagcgcaaa tgtcgctgaa acgaaggcgc agcaagcggt gtcaatccca      3240
gaactcatgc ctaatcatgc gcctaatcat gcaagagtcc cgccctatac gcccccccatt      3300 cctgccgcta agccctgcat ttggaactat caggatctgg tggaatacgc cgaaggcgac      3360
attgccaagg tctttggcgc cgattatgcc attatcgaca gctacgcacg gcgcgtgcgc      3420
ctgccgacct cggattatct gctggtctcg cgggtaacga agctcaacgc gcaaatgaac      3480
cgctatcaac cgagcagtat gaccacagaa tacgatattc ccgtggatgc gcccttcttg      3540
gtcgatggcc aaattccttg ggcagtggcg gtcgaatcgg gccagtgcga tttaatgctg      3600
atcagctact taggtatcga ttttgaaaac aagggcgagc gcgtctatcg tttgctcgac      3660 tgcacccctca ccttccttgg ggatctgccc cgcggcggtg ataccctgcg ctacgatatc      3720
tccatcaacc actttgcccg caatggcgat accctgctat ttttcttctc ctacgaatgc      3780
tttgtgggcg ataagctgat cctcaagatg gacggcggct gcgcgggatt ctttaccgat      3840
aaagaactgg ccgatggcaa aggggtgatt cgcaccgagg tcgaaattaa ggtgcgcgag      3900
caagcacaaa ttgcactggc caatgaatat acccgaaacg gcaataagcc acgcttcacg      3960
ccgctactta actgcgcgca aactgccttt agctacggcc aaatccatcg tctactgagc      4020
gccgacattg gtggctgttt cggcggtgaa catgcggccc atcaagcaaa gtttggtctc      4080
cagccttcac tctgcttcgc ctcggaaaaa ttcctgatga tcgagcaagt cagtaagctc      4140
gaagtgcatg gcggcgcctg gggcttaggc ttgattgaag gtcacaagca attagcccccc      4200 gaccattggt atttcccctg ccatttcaag ggcgaccaag tgatggcagg ctccctcatg      4260
gccgaaggtt gtggccagtt actgcaattt tttatgctgc atattggtat gcatgctaat      4320
acacaagcag gtggcgttac taaccggccgt ttccaacccc ttgaaaacgc atcgcaaaaa      4380
gtgcgctgcc gcggtcaggt attgccacaa tctggcaccc tcacctatcg catggaagtc      4440
accgaaatcg gcatgagccc tcgcccctat gccaaggcga atattgatat tctgctcaat      4500
ggcaaagtgg tggtggattt ccaaaatctc ggggtgatga ttaaagaaga agcggattgc      4560
acccgctatt cgcaaagcca ttcttcacag ggtaatcata cgcaagcagc aaatatcgaa      4620
agtctcgcgg aacaagcgcc gctaatggcg caaatcccag atgttgcagc tccggtcaat      4680
```

```
aaaggcgttg tgccgcttaa gcatgtgagc gcgccgattg cgccagcagg ctctaagtac    4740
gccaaccgcg tgcccgacac cctgccgttt actccttatc atttatttga gtttgccacc    4800
ggcgatattg aaaactgctt cggccccgat tttagtattt accgtggctt aatcccgccg    4860
cgtacgccct gtggcgatct gcaactcact acccgagtgg tggctattga aggcaaacgt    4920
ggcgagctga aaaagccatc cacctgtatt gccgagtatg aagtgccag caacgcgtgg    4980 tattaccgta aaaccagcca cccgagtgta atgccctact ctgtgctgat ggaaatatca    5040
ttgcagccaa atggctttat ctcgggttat atgggcacga ccttaggctt ccagggcag    5100 gagttattct tccgcaatct cgacggcagt ggcaagttac tgcgcgaagt ggatttacgc    5160
ggtaagacca tagtcaatga ttcgcgcctg ctgtctaccg tgattgctgg cagcaatatc    5220
attcaaaact ttagctttga gctgagctgc gatggcgagc ccttctaccg tggtaatgcg    5280
gttttcggtt actttaaggc cgatgcgctt aaaaaccagt gggtatcga caatggtaaa    5340 attacccaag cgtggcacct tgagcgcggt atcaaagccg actgccaaat caatctgtta    5400
gataaaaatg gccgcagttt cgtggcgccg ctgggcaagc cacactaccg cctagcgggt    5460
gggcagctga actttatcga caaggccgaa attgtaaaaa ctggcggtaa gaaggggctc    5520
ggatacttat acgccgagcg caccattgac ccgagcgatt ggttcttcca gttccatttc    5580
catcaggacc ctgtaatgcc aggctccctc ggtgtcgagg cgattatcga attactgcaa    5640
acctatgcca tagaccaaga cctaggcgca ggtttcaata atccgaaatt tggccaaatt    5700
ctgtcagaaa ttaaatggaa gtatcgcggt caaattaatc cattaaacaa acagatgtcg    5760
ctggatgtgc atatcaccag cattgaagat aaagacggta acgcatcat caagggcgat    5820 gccaacctga gtaaggatgg cctgcgcatt tatgaggtga ccgatattgc catctgcatc    5880
gaagaggcat ag                                                        5892

<210> SEQ ID NO 40
<211> LENGTH: 1644
<212> TYPE: DNA
<213> ORGANISM: Shewanella oneidensis

<400> SEQUENCE: 40
atgacgaata ccacactcga taataacgct ctcgataata caagctcag tccttggccg      60 tggcaggttg atgaagccgc catcagtttc gatatcgaat cccttggcaa aaaactcaaa    120
gatctcaatc aagcctgtta cttaatcaac catgctgaga aaggcttagg catagcccaa    180
agcgccgaag tggtcggtct tgcagaaccc aataatggtt gcatcctgt aagcgccttc     240 gcccccgccc ttggcaccca gagcttgggt gacagtaatt tcgccgcgt gcatggggtg     300 aaatacgctt actacgcggg cgccatggcc aacggtatcg cctcggaaga gttagttatc    360
gccttaggtc aggcgggcat tttgtgctcc tttggcgcgg cagggttaat tccgtcgcgc    420
gtggaagccg cgattaaacg cattcaagcg gcattgccca atggtcccta cgcctttaac    480
ttgatccata gcccgagcga gcaagcgctg agcgtggca gtgtcgaact cttccttaaa    540
catcaagtgc gtacggttga ggcctcggct ttcttgggct taacgccgca aatcgtctat    600
taccgcgccg caggcctgag tcgcgacgcc agcggcgaga ttgtgattgg caataaagtg    660
attgctaaaa tcagccgtac tgaggtggct accaagtttta tggagcccgc cccgttaag    720 atactgcaac aattagtgaa cgaagggctt atcagcgaag atcaaatgct gatggcgcaa    780
tctgtgccca tggccgatga cattaccgcc gaagcagact caggcggcca caccgacaat    840
cgccctctgg tcacgctatt gccaaccatt ttggcgctca agataccat tcaagccaag    900
```

| | |
|---|---:|
| taccagtata aaacgccgat ccgagtgggc gcaggtgggg ggatcggcac ccccgatgcg | 960 |
| gcgctggcga ccttcaatat gggcgcggcc tatattgtca ccggctcaat caaccaagcc | 1020 |
| tgcgtggaag cgggtgccag cgaacatacc cgtaagttac tcgccaccac tgaaatggcc | 1080 |
| gatgtgacta tggcgcccgc cgccgatatg tttgaaatgg gcgttaagtt acaagtggtt | 1140 |
| aagcgcggca ccctattccc gatgcgcgcc aataagctct acgagattta cacccgctac | 1200 |
| gactcgatag aggcgattcc agcagaggaa aggcaaaagc tggaagagca agtatttcgc | 1260 |
| gcctcattag atgagatttg ggcaggtact gtggcgcact taatgagcg cgatcctaag | 1320 |
| caaattgagc gcgcgctgga taaccctaaa cgcaaaatgg cactgatttt ccgctggtat | 1380 |
| ttaggtttat cgagccgctg gtcaaacact ggtgaagtcg gccgcgaaat ggattaccag | 1440 |
| atttgggcag gccccgccct cggcgccttt aatgcttggg ctaaaggcag ttatttagat | 1500 |
| gattaccgcg agcgcaatgc ggtcgacttg gcgaaacatt taatgcaagg cgccgcctac | 1560 |
| caagcacgga ttaacctgtt gttatcccaa ggggtaagta ttccagtcag cctgcaacgt | 1620 |
| tggaaacctc tgcaacgctg ctaa | 1644 |

<210> SEQ ID NO 41
<211> LENGTH: 8316
<212> TYPE: DNA
<213> ORGANISM: Colwellia psychrerythraea

<400> SEQUENCE: 41

| | |
|---|---:|
| atggctaaaa agcaaagcac atctaataac cctgtaacga atgaagcaga cgaaaaagcg | 60 |
| tttaattctc gtcttcaaga atgtcctatt gccattgttg gcatggcgtc tatctttgct | 120 |
| gatgcaaaga acttagaaaa ctactgggac aacattttg aatcagtcga tgcaattaaa | 180 |
| gatgtaccca gtgatcgttg ggcaaaggat gattattact cgagcgatcc aaaagaggct | 240 |
| gataaaacct attgtaaacg tggtggtttc ttaccagaaa tagacttcga cccaatggaa | 300 |
| tttggtttgc caccaaacat tttagagtta actgatatcg ctcagttatt gtctttagta | 360 |
| gttgcacgtg aagtattaaa cgatgcaggt attggtgatg gtctggtta cgatcgtgac | 420 |
| aaagttggta ttacgttagg tgtaggtggt ggacagaaac aaatttcgcc attaacgtct | 480 |
| cgcttgcaag gcccagtatt agagaaagta ttaaaagcgt caggtgttga agaagctgat | 540 |
| cgcgccatga tcattgaaaa gttcaaaaag gcctatatcg gttgggaaga aaactcattc | 600 |
| ccaggcatgt taggcaatgt tatttctggt cgtattgcta accgttttga ttttggtggt | 660 |
| actaactgtg ttgttgatgc ggcttgtgca ggttctttag cggcgattaa gctagctatc | 720 |
| tcagacttac ttgagcacag atctgaagta atgatctctg gtggtgtttg ttgtgacaat | 780 |
| tcaccattta tgtatatgtc atttcaaaa actcctgctt ttacaacagg tgaagacatc | 840 |
| cgcccatttg ataatgattc aaaaggtatg atgattggtg aaggcatcgg tatgatggct | 900 |
| ttcaagcgtt tggaagatgc tgaacgtgat ggtgataaag tttacgccgt acttaaaggt | 960 |
| attggtactt caagcgatgg tcgctttaag tcgatttacg caccacgccc agatggtcaa | 1020 |
| gctaaagcgt taaacgtgc ttatgaagat gcagggtttg atccaaaaag ctgtggcatg | 1080 |
| attgaagcgc atggtacggg cacgaaagcg ggtgacgcag cagaatttgg cggcttagtt | 1140 |
| aaacacttct cacaagataa tgatcaaaaa caacatatcg ccttaggctc tgttaagtct | 1200 |
| caaattggtc acgctaaagc ggccgctggc gcagcaggta tgataaaagc ggtattagcg | 1260 |
| cttcatcata aagtgctacc agcaacacta catatcgacc aacctaatac ctcgttagac | 1320 |

```
attgaaaaca gtccaatgta tttaaacagc gaaacacgtc cttggatggc acgtgaagat    1380
ggtttaccac gccgcgcagg tatcagttcg tttggttttg gtggtactaa ctaccacatg    1440
gtattagaag aatactcgcc aaaagcacaa ggccagtatc gcttaaatgc agtgccacaa    1500
acactgttag ttacagcggc taacgaaaaa gcattagtga gttcattaac agattggaaa    1560
aataaattaa gtgtaaaagc agatgatcaa ccatacgctt ttaacgcctt agttgttgaa    1620
aacacgttaa caacaccagc ggttgctcta gcccgctgtg gttttgttgc aaaaaatgct    1680
gatgaagcaa tcaaaatgat tgaaggtgct ttgacgcaat ccaagccaa atcaggtggt    1740
gacattcctt gtgaagagtg gtcagtacca acgggtattt attaccgtaa gtctggcttg    1800
tcagtgagcg gaaaggttgt cgctctcttt tcaggtcaag gctcacaata cgttaatatg    1860
ggccgcgagc ttgcttgtaa cttcccaagc gtaatgcaag ctgctgcaga tatggacagt    1920
gagtttacac aagcaggttt aggtcaatta accccgacaa cgtatccaat tcctgtatt    1980
aatgatgatg cacgtaaagc acaagatgaa gctttacgtt taactcaaca cgcacaacct    2040
gcaattggta ccttaagtgt tggtctatat aaagcgttta ctaatgctgg tttcaaagcc    2100
gactttactg cgggacatag ctttggtgaa ttaaccgcgc tttgggctgc aggcgtagta    2160
agtgatagtg actatatgat gttagcacgt agtcgtggtc aagcaatggc agcacctaca    2220
ggtgaggctg cgataggatt tgatgcgggc actatgattg ccgttgttgg aagtccaact    2280
gatattgcta atgatattaa agacatcaaa gatatctcta ttgcaaacta caactctaat    2340
aaccaagtag ttgttgcggg tgtaagcact caaatagcaa tcgctatcga tgagttaaaa    2400
ggcaaaggtt ataaagttgt accattaccc gtttctgccg cgttccatac gccacttgtg    2460
ggccacgctc aaaaaccatt tagcgatgct attgataatg ctaaatttaa taagccgctt    2520
gtacctgttt attcaaatgg cacagccaaa gcgcattcaa ataaagcggc tgatattaaa    2580
aagtcactga aaaatcatat tttagaatca gtacacttta acgaagaaat tgacaacatt    2640
tacgctgatg gcggacgagt atttgttgaa tttggcccta aaaatgtatt aaccaaactt    2700
gttgaaaata tcttaaaaga taagaagac gttgtagcta tagcggttaa tgctaatcca    2760
aagaaatcgg ccgatatgca aatgcgtcaa gcggcagtgc aaatggcggt acttggttta    2820
gagttaacag aaattgaccc gtattcagcg gttaaacgtc cattatctgc acctaaaatg    2880
tcaccactag cgatgaagct aactggcgca tcttatgtga gtcctaaaac taaaaaggca    2940
tttgatgatg cactaaatga cggttggaca attaaacaag caacgtcagt tcctgttgct    3000
gtgcctgagc cacaagtggt tgaaaaaatt gttgagaaga tcgttgaagt agagcgcatt    3060
gtagaagttg agagaattgt ttacctgact gcagacggga aagtcttcga tggtagtgtc    3120
gcagatggaa ctgttgctaa tggtcaagca gctaacagtt ttgcagtaaa cgtaaacact    3180
gcggatatag caaatagtat tgaacgtagc gttagtcagt ttgttgatca ccaacaacag    3240
ttattaaacg tacatgagca atatatgcaa ggtccaaaag actatgcaaa aacgtttgat    3300
acggtcctat ctaaccaaga agcaggcgag ttacctgaaa gcctagaccg tacgttaggt    3360
atgtatcatg acttccaatc agaaacattg cgtgttcatg agcaatattt gaataaccaa    3420
actgataata tggcaacgat gttgtctgct tctgaaagta atacagaggt gagttctaac    3480
atagttaaaa catcaccaat cgcgactcaa gcacctgtta ttaaaagtgt agtgacacaa    3540
gcgcctgttg ttaaaccaac aatttcagtg gcacctgcaa cacaaacgtt acctgccgcc    3600
gtatctcctc cagtagtatc tgctccagta gtaaatgcgc ccgcacaatc agtagcaaca    3660
gccgttgcga tggcgccggt agctgaagtt tctattgctg ttcctgttca ggaatcatca    3720
```

```
cttgaccttg aacgcattca aacagtgatg atggaagtag ttgctgagaa gaccggttat    3780
ccaacagaaa tgttagaact tgaaatggat atggaagctg atttaggtat tgattcaatc    3840
aagcgagttg agattttagg ctcagtacaa gaaattattg ctgatttacc agagcttaac    3900
cctgaagact tagctgaatt acgtacctta ggcgaaatcg ttgactacat gaagtcgaaa    3960
gcacaagctg cggctcctag tgcgtcagcg aatgacagtg caccagcact acatttagtc    4020
gatagctcag ttgtgccaag catcgattta caacacatcc agaatgtgat gatggaagtg    4080
gttgctgaga agaccggtta cccaaccgaa atgcttgagc ttgaaatgga catggaagct    4140
gacttaggta ttgattcaat aaaacgtgtt gaaatcttag gttcagtaca agaaatcatt    4200
aacgatttac cagagcttaa ccctgaagat ttagctgaac tgcgcacctt aggtgaaatc    4260
gttaactaca tgcaatctaa agtatcagcg gctcctgtag cgagtgcccc agttaatacg    4320
actgtaagca gcacgcctgc aatcgattta attcacatcc aaaatgtgat gatggaagtg    4380
gttgcagaaa aaactggcta cccaactgaa atgcttgagc ttgaaatgga catggaagct    4440
gacttgggaa ttgactcaat caaacgtgtt gaaatactgg gtgctgttca ggaaactatc    4500
cctgatttac cagagcttaa cccagaagat ttagctgagt tacgtacatt aggtgaaatc    4560
gtaagttaca tgcaaagtaa agtatcagta gcgcctgcag cagttgcagc aattgtgcca    4620
aatgcgacag ctaatgcaag tgctcctgca attgacttag attacattca gagcgttatg    4680
atgacagtag tagcggagaa aactggctac ccgactgaaa tgcttgaact tgaaatggac    4740
atggaagctg atcttggtat cgactcaatc aaacgtgttg aaatacttgg tgctgttcag    4800
gaaactatcc ctgacttacc agagcttaac ccagaagatt tagctgagtt acgtacctta    4860
ggcgaaatcg taagttacat gcaaagtaaa gtatctgtag cgccaatagc agttgttgat    4920
aatgctcaag ctgcgtcagc cattgtgcca actaaggtaa gcagcgctcc tgcaatagat    4980
ttagattaca ttcaatccgt aatgatgaca gtagtggcgg agaaaactgg ctacccaact    5040
gaaatgcttg agttagccat ggatatggaa gcagacttag gtattgactc aatcaaacgc    5100
gttgaaattt aggtgctgt tcaggaaacc atccctgact taccagagct taacccagaa    5160
gatttagctg agttacgtac cttaggtgaa atcgtaagtt atatgcaatc taaggtaaca    5220
cccgttgcag atgttactgc tgaaacaagt acgctagcga atgaaagcgc tccagcaatt    5280
gacttagatt acatccaatc tgtaatgatg acagtagtgg cagagaaaac tggctaccca    5340
actgaaatgc ttgagcttgc catggatatg gaagcagact taggtatcga ctcaatcaaa    5400
cgtgttgaaa ttctcggtgc tgttcaggaa actattcctg acttaccaga gcttaatcca    5460
gaagatttag ctgagttacg taccttaggt gaaatcgtaa gttacatgca aagtaaagta    5520
tcgccaacgg atccgactga ccctaaagga acaggtgtta aaaccactgt ccctgctgct    5580
gttcttgcaa atggtaggtc agtagaaaca gcggttaact ttcaaggcgc acctagtgca    5640
actgttgaac taacagcatt atcttcagtg aacaaaattg ttcaagatgt tactggtgaa    5700
ggcaaacaat caggcgctaa cgcgttagtt gttgatgatg gcagtggcgc agccgtggcg    5760
ttaagtgctc aactgatcaa agcaggttgg caagttacgg cattaaaacc taattgggtg    5820
gtcagccatt cgaaaaaagc gtttgctaca gcagtaaatg ttgttgaaat tggtactcat    5880
gataaaacac ttgatgaagc tcaagtaaaa gacatcattg agaaaacagc acaattagac    5940
gcagttattt acttacaagc agcaaatact gttgatgcta tcgaatacccc agaagcggca    6000 aaacaaggct taatgttagc cttcgtatta gctaagttgt cgaatgtaaa gttagcgact    6060
```

```
aatgcacgtg cttcttttgt tgtggtaact cgccaaggtg gcgctttagg cttttctaat    6120
ggtgatgctg atagtggtac gcaacaagtt aaagccaatg tgaaagccga cttagtgcaa    6180
gcaggtttag cgggcttagt taaaaccatc aaccatgaat ggaacgctgg cgaaggcagt    6240
gttttctgtc gaattatcga tttatcaagt aaattagcag cagataaagc agcaactatc    6300
atcaatgatg agttacttga tattgacggc agtattgttg aagtagcaca tgataccgat    6360
aacctgagta ataacattgg ctcacgtcta acgctatctg gtgtggttac cgatagttat    6420
gcactaacac caattgctaa agggtcaaac acagcaatta acagtgactc ggtattttg     6480 gtaagcggtg gcgcaaaggg ggttacagca cattgcgtta tcgaaattgc caaacagtac    6540
caagctaagt ttattttatt aggtcgttca tcctttgatg caacgagcc aagctgggca     6600 caaggcatta gtgatgaagt tgctttgaaa aagcagcga tgcaagcatt gattgcaagc     6660
ggcgaaaaac caacaccagt taaagtgact cagtttgtac gtccggtatt agctaatcgt    6720
gaaattgcgc aaaccttagc ggcaattaaa gcggcaggcg gcaagcaca ttacgctgct     6780 gccgacgtga cgaatagtgt aagtgttagc gctgcggttc agcctttact aaaaacctta    6840
ggtcaaggtt ccttcaagt tacgggcatc attcatggtg cgggtgtctt agcggacaag     6900
tttattgagc aaaaaacgct tgaagaattt aacgcggtat acacaacgaa aatagatggt    6960
ttattgtctt tattagcagc aaccaatgcc gaaaatatta aacacttagt gttatttca    7020 tcagcggctg gttttatgg taacccaggg caatctgatt actccatcgc taatgatatt     7080
ttaaataaaa cggcttaccg ttttaaagca ttaaatccaa gtgctcaagt actaagcttc    7140
aactggggac cttgggatgg tggcatggta acaccagagc ttaaacgtat gtttaacgac    7200
cgtggtgttt atattattcc acttgatgca ggcgctaaat tattggtaag tgaactcgct    7260
gcagatacta accgttgtgc acaaatcctt gttggtaatg atttgtcgaa ggatacagct    7320
aaggatgcat ctgtaaaaaa gccacaagtt agtcgcttaa ctagccgtgt taataaaaca    7380
cttttagcga ctaacaatac ctttttagct gaccacacca ttggtgatga caaagtatta    7440
ccaaccgtgt gcgccatagc atggatgagt gaagccgcaa tggttgctta cccagcattt    7500
cattatcaag gactagcaaa ctataagttg tttaaaggca tcatctttga tggcagtgaa    7560
gcaacagaat attcaatcga tatgattgct caagttgagg gtgaaagctt agtagtagac    7620
actaaaattt caagtactaa tgagcagggt aaaccagtat ttcattatgg cgctcagctg    7680
acattagtcg ctaaagcgga aagaaaagaa gcgccaacgg ttgaacttat attacctgaa    7740
gctttaccag aattacttcc ggaaacagta ctttcgagca ctgaagaagc aggcgcttta    7800
tatactaatg gtactttatt ccacggtgaa agcctgcaag gaattaaggc aatacttgcg    7860
tgtaatgagc aaggtctatt attgaaatgc caagtaccag cagtggcaag tcttaagcaa    7920
ggcgagttcc cgattagccc gttgaatagt gcaagcgaac actcgaacat ttttgccaat    7980
gatatcgctt atcaagccat gttagtttgg gctaaaaagc aattaggttt aggtagctta    8040
ccgtcaagta cgcaaagttg gacggtatac cgtgacgtca gtcttggtga aaacttctac    8100
cttaaattaa cggtagtgaa aagctcaggc aaaggaaagc aacgtggttc tttagtggct    8160
gacattgaaa tgattgatga aaacaatcga ttactcagtg agataaaatc tgccaaagtg    8220
acggctagtc taaacttaaa tgacttattc ctacctaaaa aggcaccgaa aactacaccg    8280
aaagctaagc aaagtgaaag tgaggcaagt gcgtaa                              8316
```

<210> SEQ ID NO 42
<211> LENGTH: 2703

<212> TYPE: DNA
<213> ORGANISM: Colwellia psychrerythraea

<400> SEQUENCE: 42

```
atggttaaca atcattataa aacggccatt attggtttag atgctcagtt tgaaaatgaa      60
cagagcgttc aaaccgatat tgatcgggtt gaacgtgcgc tatacctcgg caaactttca     120
gggaatatct caggtaagag cctagatcaa gctgaaatat cagacaagga aaatacaaca     180
ctcaagctaa gctgttcagc aacggttgag cgtatggcac ttgctaatca agtcagtagc     240
gctgatatca aagttgttgt gctaatgcac gacagtgaaa atatagtcat tgatattgaa     300
aatgttattg ttgttacttc gttagctagc gcactacaac aaatagatac gttgattgag     360
caaaatttct tggtagcctt gcttggtatt aatttactta gtttaagcga taagcaaaat     420
ggcagtgatg tttgccaaga gctggcgacc atctcatatg atcaaaactt tagcgcttat     480
caagcgtgtc gcgtattgc tgcattatta tttgcacctg caacgtttgc acaaactcat      540
cactgttatg tctattcgcg gataaaaggt tttgccacgg ggagcgatat aactagtgtt     600
actgctgcag cgttagataa agcgcaagtc aatgcaacag atattggttt gcttgaagtt     660
tctgcgttat caaataaaga tgcttcgctt gctgaaacaa aaggtttatt gagccattat     720
ttaatagatg gtgccaataa agcagtaatg agtgaagatg ccaatgaagc attaaatacg     780
gctatctctt gtgcacgtag tgttaccgga gaaggggctg ctttctga agtgttaggt       840
ttgttacgta ccgttattgc actgcaacaa cgttatattc ctgccattac tgattggcaa     900
caaccacaag ccagtgaact tgaaaaatgg caaagctcaa gctgttactt tccaacagag     960
gctcgtccat ggtatccaca gcctaatggt aatgcccact tggcgcgta cagttgttta     1020
accgtttcag acaataatca tgattattgt catattatcc tgcaagaaga gcaggttggt    1080
cttattgatg gtaaacatgc tgcaagcgat attcgcagta atggttttat tgcctgtagt    1140
gatttacagc tagtattaat tggcgcagag gatttaccta atttattaac tcagttaatt    1200
gatcttgaag atgagcttga agctactttt aaaggtaacc ttgaagagaa ggctgaacag    1260
agtagaacat cacttaaaga tattgcttta acgcgttttg aacagtctaa aggcaatagc    1320
agtcgttata cgattgcctt attgtctgaa tcgatagaag aactaagcaa agaaatataaa   1380
ctcgctaaag ccggtgttcc tgcagcattt tctgatgtta ttctgataaa gaataatcag    1440
caagaatggc gaacgccaaa aggcagctat tttagtgcta gccctgttaa taatagtgaa    1500
tcagcgacta ataatgtttc attttatat ccgggcattg gtgcaacgta tgtcggttta     1560
ggacgtgatt tattccacct ttttcctgaa atacaccaag atgttgctaa cttagccgac    1620
gatattggcg caagtttaaa agataaaatta ttaaatcccc ggtccataat tcgtcctgat   1680
tttaaagcat taaaacagct tgatttaaac ctccgtggta agttggctga tattgcagaa    1740
gcaggcgttg gttttgcgtg tgtattcact aaagtatttg aaaacgtctt taaggtaaag    1800
gcagactttg ctacaggtta cagcatgggt gaagtcagta tgtacgctgc attgggtgca    1860
tggcaacaac caggattgat gagcgcacgt ttagctaatt cagataccctt caatcaacgt    1920
ttatgtggtg acttgctaac tttacgtgag cattgggggc ttcctagttc gacaagtagt    1980
cctactaata gccctagcaa tgaccaagct gaaagtctag atgagttgat ttgggaaacc    2040
tacaccatta aagcaacgtt agatgaagtt atcgctgcca gtgaagatga agaacgtgtt    2100
tattgcacca tagttaatac gccagacagt ttattattag gtggttatcc agccgattgt    2160
ctacgcgtta ttaaaaaact tggtgtacgt gctatgccac ttaacatggc aaatgcaatt    2220
```

-continued

```
cacagtgcac cagcaaaaat tgaatatgac gacatggttg aactttatac catggacgtt    2280
actgcgcgct taaaaactaa aatgtattca agctcttgtt acttacccgt accacaaatg    2340
agcaaagcga ttgctcacag tgttgctaag tgtttatgcg accgagtaga tttcccccgt    2400
ttaattaaca ccatgcacga taaaggtgcg cgggtattta ttgaaatggg accagggcgc    2460
tcgttgtgca gctgggtaga taaaatttta gattttgacg atagcagtaa aaatggcctc    2520
tctaataaag aacctaatca agttgctcat aaagcacgag tatcagtgcc agtgaatgca    2580
aagggcacaa gtgacgagtt aacgtatgtg agagccgttg caaaattggt tagtcacggg    2640
gtgaaactag atcttcaccg cttatttaat ggctcaatta ttgtgaaaaa gccacaagct    2700
taa                                                                  2703
```

<210> SEQ ID NO 43
<211> LENGTH: 6051
<212> TYPE: DNA
<213> ORGANISM: Colwellia psychrerythraea

<400> SEQUENCE: 43

```
atggaaaata ttgccgtagt aggtattgct aatttattcc caggatcttc tgcaccagaa      60
gaattttggc agcaattgct gaagaaacag gattgtcgca gtaaagcaac caagaacaa     120 atgggtgttg accctgaaaa atacaccgga aaaaaggcg acacagataa atttactgt      180 gtgcacggtg gttatattcg agatttcaat tttgatgcaa catcatttat tcagaacact     240
gctggtttaa ccgcaccgct gagtgaagag tacctaaatc aactagatga tctaaataag     300
tgggctttgt atgttaccca acaagcatta accgacgcag gttattgggg cagtgataag     360
cttgagcaat gtggcgttat tttaggaaac ttatcgtttc caaccaagtc gtctaatcac     420
ttatttatgc cgttgtatca ccaagttgtc gataacgcat aaaagccgg tatcgataaa     480 gattttcagt taagtcattt ttctgatact gatatttcga ccaataatat tcatgcagat    540
aatgcgctgg ttgcgggtta ccctgcggcg cttttagcga agctgcgggt cttggtggt     600 acacactttg cgcttgacgc agcctgtgca tcaagctgtt attcggtaaa attggcttgc    660
gattacttgc atactggtaa agctgacatg atgctagcag gtgcggtatc aggctctgat    720
cctatgtttg ttaatatggg gttctcaatc tttcaagcct acccagctaa caatattcat    780
gccccgtttg ataaaaactc tcaaggctta tttgccggtg aaggtgcagg catgatggta    840
ttaaaacgcc atagtgatgc ggtacgtgac ggtgataaaa ttcatgcgat tatcaaaggt    900
ggtgctttat caaatgacgg taaaggtgaa tttgttctta gcccaaatac taaagggcaa    960
gtgcttgttt atgaacgtgc ctatgaagat gcagcggttg acccacgtga tgtagattac   1020
attgaatgtc atgctactgg cacaccaaaa ggcgataacg tagaacttgg ctctatggat   1080
accttcttca gccgtttccc aagagaaaat ggcaataagc ctttgcttgg ctcagtcaaa   1140
tctaacttag gtcacttact taccgcggca ggtatgccgg tatgactaa agcgatttgg    1200 gcacttaatg aagcaaaaat ccccgcaacc attaacttaa cgagccatt aagctctaaa   1260 aaaggttatt taggcggcgc acaaatgcca acagatacta tcgattggcc agttcctgct   1320
aacagtgcaa acaagccaag aaccgctggt gtcagtgtat tggttttgg tggctctaat    1380 gctcatttag ttttacaaca acccacacag caacttgagc ctattacggt aaaagccaaa   1440
ccacgtgagc cgctcgccat tattggtatg gatgctcatt ttggtggtgc tgaagatctt   1500
gctagtttta aaacacttat cgaaactaat gataatactt tcagagaatt accgacgaat   1560
cgttggaaag gcattgataa cgatactgat gtgatgaatg ccttgcagct tagtaaagca   1620
```

```
cctcagggcg gctatgttga aaactttgat attgattttt tacgtttcaa agtgccacct    1680
aacgagcaag actgtttaat tccccagcaa ctgatgatga tgaaagttgc tgataatgca    1740
gcgaaagatg caggacttaa agaaggtagc aacgttgcgg tacttgtagc tatgggtatc    1800
gaactcgagc tgcatcaata ccgaggtcgc gttaacttaa gcacacaaat tgaagaaagt    1860
ttattacagc aaggcgttac gcttaactca gagcaacgtg aaacattaac caatatcgct    1920
aaaaatggcg ttgctcacgc ggcgcagctt aatcaatata cctcgtttat tggtaatatt    1980
atggcgtcac gtatttcagc attatgggat tttaccggtc ctgcgataac gctttctgcg    2040
gaagaaaact cagtttatcg ttgcgtagaa ttggctgaga acttattcca aacatcagac    2100
attgatgccg tgattatagc ctcggttgat ttagctggct cagtagaaaa atattacctta   2160
agacaacact tcggtccggt agaaaagggg caggtagaaa caggctcagt ctcaacaaat    2220
tctgcaacct cagcaaatgt ccttgaacaa atacatggc gagtaggtga aggggcaggt     2280
gcgtttgtcg ttaaacccct gtctaaagtc atccaagttg cagagcaaag tatttacgcc    2340
accatagacg gtattagttt tgccaatggt aaagatgctg cggccatcac taaggccgca    2400
agcgcttcac tgaacattgc agggcttaac agcgcagata ttacgagtgt tgaagcacat    2460
gccagtggtt ttagtgctga aaatatagca gaagctcaag cactaccagc attgtatgca    2520
ggcaaagtga ttagcagtgt taaaagcaat attggtcata cgtttaatgc cagtggtgtt    2580
gccagtatta ttaaaacagc actcttgtta gatgataaag tgttaatga agagcgctta     2640
acctctcatg tcgcgtctca tatagccgtg aatggcttag gtaaagatga aagctgtgcg    2700
caccttattt tgtcatcgag caagctagcc catcaagcag cgcctcctcc aacaggcaaa    2760
caacgtccta aactaattaa aaatattagt ttaggtggca aggccatttt tgcagacatc    2820
attgctaacg ttaaagcacc ggcaatgacg gcgattaagc aagcttttac taagcaacct    2880
ttacgtcagg ttaaacaggc ggttaatgtc atgaacatta aacctaagct aactgaagca    2940
aaagtagctg aagttaagtt atcccaagct gctcagccaa ctaatttatc tagtcaagct    3000
cacacacgat caacggtcgt taccggagta aaagtgaaga aagttactaa tactgctatt    3060
gcaaataacc aaagcaagag gcaagtacct gcagatgtta acatcaagc aagtaaagaa     3120
attttccaag aatcagctac acatcaagcc ttttttaaata ctcgccaaat ggcaggtcag   3180
cagatttcga aattgattga aatgcaagct aatgtcagtg cagggttgcc gacttatgtt    3240
tcaacaacaa gcgcagctga gccggtaaat gaacgtcagc atgcacctga gctttcggtt   3300
gtttcttcaa atgtacaagc ggaaaaccag cagtgggcaa atgaatctgg ttttaaaatc    3360
aaaggcccag caggatacag ctacccacca ttacaacttg aagagcgctt taataaaccc    3420
gaagaaatta tttgggatac tgccgattta gttgaatttg ctgaaggtga tatcgcgaaa    3480
gttttttggtg atgagtttaa aatcatcgac agttattcac gtcgtgtacg tttaccgacc    3540
acagattatt tattagtttc acgtgttacc gagcttgaag ctacggtaaa tgaatataaa    3600
aaatcataca tgtgcactga gtatgatatt cccgttgatg cgccgttcct tatcgatggt    3660
caaattcctt ggtcagtatc ggttgaatca ggacaatgtg atttattatt aatttcttat    3720
attggtattg attttcaagc caaggcgaa cgtgtttatc gttacttga ttgtgaatta      3780
accttcttag aagaaatggc ctttggtggt gaaacactgc gttatgaaat tcatatcgac    3840
tcatatgcac gaaacggcga gcaattatta ttcttctttc actacgattg ttatgttggt    3900
gataaaaaag tattaatcat gcgtaatggt tgtgctggtt tcttcactga tgaagaactt    3960
```

```
gctgatggca aaggcgttat cttaaatgat aaagataaag cagaattagc taatgccgtt      4020
aaaagtgatt ttgcaccatt aataactaat attgatgcag cgaaacaagc caaacagcat      4080
ttcgattacg ttgacatgat gaaattggtt gatggtgatg ttgcaggttg ttttggtgaa      4140
gaatataacc aacaaggtcg taatccgtca ttaaagttct cgtctaagaa attcttaatg      4200
atagagcgca ttactaagat tgatgcaaaa ggcggtcatt ggggcttagg cttactagaa      4260
ggtcaaaaag acttagaccc acagcattgg tatttcccat gtcactttaa aggtgaccaa      4320
gtgatggccg gctcattaat gagtgaaggt tgtggtcaaa tggcgatgtt cttaatgctt      4380
aaattaggca tgcacgctaa tgtaaataac gcacgctttc agcctatgcc aggtgagtcg      4440
caaaccgtac gttgtcgtgg ccaagtactt ccgcagcaca atacgttaac gtatcgcatg      4500
gaagtaaccg caatgggcat gactccttac ccattcttaa aagcgaatat cgaaattatt      4560
cttgatggta aagcggttgt tgattttaaa aacttatcag tgatgatcac tgaacaagat      4620
gataactcgc catatccggt aactttacct gacaatgttc agcttcaaca aagcaaggtg      4680
caaccagtaa caaatgccga agttaaaagt gcagacacca atcttgaact agatgaacgt      4740
ggtgtagcgc catttaaaca ccctgaacgt gctttaatga agttgtgtc tgatttgatc      4800 gcgccaaaag agaagggcgt aacaccaatt caacattttg aagcgccaat ggtagctggt      4860
caaaaccgcg tacctaacca agcaccgttt acaccttggc atatgtttga atttgctacc      4920
ggtaatatct ctaaatgttt tggtcctgat tttgacgtgt ataaaggtcg tattcctcca      4980
cgtacaccct gtggtgattt acaagtcgta acacaagttg tcgaagtgca aggtgagcgt      5040
ttagatctta aaaagacttc tagctgtatc gcagaatact atgtgccgag tgatgcatgg      5100
tatttcacta aaaacagcgt taataactgg atgccttatt cattaatcat ggaaattgcc      5160
ttacaaccga atggctttat ttcaggttac atgggcacca cacttaaata cccagaaaaa      5220
gatttattct tccgcaacct tgatggcagc ggtgacttaa tcaaacaggt agatttacgt      5280
gataaaacca ttgttaataa atcggtatta ttaagcacta ccatggctgg cggtatgata      5340
gtacaaagct tcacttttga gctgtatgtg aaaaatgaaa gtgctgctgc tcagtcatta      5400
gaaagtcatg acttgttcta caaggtacg gccgttttg gttactttgg tgcagatgcg      5460
ttaacgaacc aattaggtat tgataacggt aaagtaacgc acccttggtt tgttgataac      5520
aatactccta atcagacat aaggtgatc gatcttagta attctaatct gcctttatac      5580
caagcgccat cgaacaaacc gcattacaaa ttagcgggtg gtcaaatgaa ctttattgat      5640
accgtttcaa tcgttgaagg cggcggtaaa gcgagtattg cttatgtaca cggcgaacga      5700
actattgatg caacagactg gttcttccgt tatcacttcc accaagatcc ggtaatgcct      5760
ggctcattgg gtgttgaagc ggttatcgaa ttaatgcaaa cctacgcatt agaaaatgat      5820
ttaggtaagc aatttactaa cccaagattt attgcaccgg caaccctagt taaatggaaa      5880
tatcgtggtc aaattacgcc attaaacaaa cagatgtctc ttgatgtgca tattacagac      5940
atcattaaag aagacggtga agtgagatta gtcggcgatg ctaacttatc gaaagatggc      6000
ttacgtatat acgaagtaaa agatattgtc ctgtcgcttg ttgaagcata a              6051
```

<210> SEQ ID NO 44
<211> LENGTH: 1599
<212> TYPE: DNA
<213> ORGANISM: Colwellia psychrerythraea

<400> SEQUENCE: 44

```
atgtcaaatt taagttatag caatgccaat ccaattgatt gggcatggaa agttgatagc       60
```

-continued

```
agcgctgtta aagccaatga tgtagaaata aagtcagcgt taatggattt aacaaagccg    120
gtttatgtcg caaaatctgc taatagtttt ggtgtagtaa acgctactgc agctaccggt    180
gatacggatg ttgtcgcttt tgctcaaaag ctaactccgc aagatttagg tgatgatgct    240
tataaaaagc agcatggcgt taaatacgct tatcatggcg gcgctatggc taatggcatt    300
gcctcagttg agctcgttgt cgctttaggc aaagccggtt ttttatgttc attcggcgct    360
gctggattag taccagatgc tgttgaagat gcgattaaac gtatccaagc agaattacct    420
aatggtcctt atgcggtaaa tttaatacat gcaccagcgg aagaagcatt agagcgtggc    480
gctgttgaac gctttttaaa gcttggcgtt aaaacagtag aagcttcagc ttatttaggg    540
ttaaccgaac atatcgtttg gtatcgttta gcgggtttat ctaaaaatag cgatggcagc    600
gtaaagatcg gcaataaagt tattgcaaag gtatcgcgaa ctgaagttgg tcgtcgcttt    660
atggagcctg cgccacaaaa actaattgat aagctactgg ctcaaggtaa agtcacccaa    720
gagcaagctg agctttcaaa gcttgtacct atggctgatg atataaccgc tgaagcagac    780
tctggtggcc ataccgataa tcgaccttc ttaaccttat tgccgacgat tatagcgctt    840
cgtgatgaag ttcaagcaca gtacaacttc tctccagcgc tacgtgttgg tgctggtggt    900
ggtattggta cccctgaagc tgcattagct gcctttaata tgggctcagc ttatattgtt    960
ttaggctcgg taaccaagc atgtgttgaa gctggcgctt ctgaatacac tcgtaagtta   1020
ctggctcagg ttgaaatggc cgatgttact atggcaccag cggcagatat gtttgaaatg   1080
ggcgtgaagt tgcaagttgt taagcgtggt tcaatgttcg ctatgcgcgc gaagaaactt   1140
tacgagctgt acattaacta tgactcaatt gaagctattc cagccgacga acgtcttaag   1200
attgaaaagc agatatttcg ctctaatctt gatgatgttt gggcaggtac tgaagccttt   1260
ttcactgaac gtgatcctga aatgttggcg cgagcacaat ctagccctaa acgtaaaatg   1320
gcgctaattt tccgttggta tttaggatta agctctcgct ggtcaaatac cggcgagaaa   1380
ggccgtgaaa tggattatca aatttgggca ggcccaagtc ttggcgcatt taacagctgg   1440
gtaaaaggca cttacttaga agattatact cgccgtggcg ccgtagacgt tgctttgcat   1500
atgttaaaag gtgcagccta cttacaacga gttaatcagc taaaactaca aggtgttagc   1560
ttaagcactg aactggctgg ctatcgtagc gaagattag                          1599
```